United States Patent [19]
Anderson et al.

[11] Patent Number: 5,599,907
[45] Date of Patent: Feb. 4, 1997

[54] PRODUCTION AND USE OF MULTIMERIC HEMOGLOBINS

[75] Inventors: David C. Anderson, San Bruno, Calif.; Antony J. Mathews, Louisville; Gary L. Stetler, Boulder, both of Colo.

[73] Assignee: Somatogen, Inc., Boulder, Colo.

[21] Appl. No.: 240,712

[22] PCT Filed: Nov. 6, 1992

[86] PCT No.: PCT/US92/09752

§ 371 Date: May 9, 1994

§ 102(e) Date: May 9, 1994

[87] PCT Pub. No.: WO93/09143

PCT Pub. Date: May 13, 1993

Related U.S. Application Data

[63] Continuation-in-part of Ser. No. 789,179, Nov. 8, 1991, which is a continuation-in-part of Ser. No. 671,707, Apr. 1, 1991, abandoned, which is a continuation-in-part of Ser. No. 374,161, Jun. 30, 1989, abandoned, Ser. No. 379,116, Jul. 13, 1989, abandoned, and Ser. No. 349,623, May 10, 1989, abandoned.

[51] Int. Cl.$^6$ .......................... C07K 14/805; A61K 35/14; C07H 21/04; C12P 21/00
[52] U.S. Cl. .......................... 530/385; 530/829; 536/23.4; 536/23.5; 435/69.1; 435/69.6; 435/69.7; 435/71.1
[58] Field of Search .............................. 536/23.4, 23.5; 435/69.1, 69.6, 69.7, 71.1; 530/385, 829; 514/832

[56] References Cited

U.S. PATENT DOCUMENTS

| | | | |
|---|---|---|---|
| 4,001,200 | 1/1977 | Bonsen et al. | 530/385 |
| 4,001,401 | 1/1977 | Bonsen et al. | 514/6 |
| 4,053,590 | 10/1977 | Bonsen et al. | 514/6 |
| 4,336,248 | 6/1982 | Bonhard | 530/354 |
| 4,338,397 | 7/1982 | Gilbert et al. | 435/69.1 |
| 4,529,719 | 7/1985 | Tye | 514/6 |
| 4,551,433 | 11/1985 | Deboer | 435/252.33 |
| 4,584,130 | 4/1986 | Bucci et al. | 530/385 |
| 4,598,064 | 7/1986 | Walder | 514/6 |
| 4,600,531 | 7/1986 | Walder | 530/385 |
| 4,769,326 | 9/1988 | Rutter | 435/68.1 |
| 4,777,244 | 10/1988 | Bonhard | 530/385 |
| 5,028,588 | 7/1991 | Hoffman et al. | 514/6 |
| 5,173,426 | 12/1992 | Fischer et al. | 435/252.3 |

FOREIGN PATENT DOCUMENTS

| | | |
|---|---|---|
| 0161937 | 11/1985 | European Pat. Off. . |
| 8809179 | 12/1988 | WIPO . |
| 9013645 | 11/1990 | WIPO . |

OTHER PUBLICATIONS

Fermi, G. & Perutz, M. F./Atlas of Molecular Structures in Biology/2. Haemoglobin and Myoglobin/Clarendon Press/Oxford/(1981), Entire Text.
Bunn, H. F. & Forget, B. G./Hemoglobin: Molecular, Genetic and Clinical Aspects/(1986), W. B. Saunders Publishing/Philadelphia, PA/Ed. John Dyson/Entire Text.
Looker, D. et al/Expression of Recombinant Human Hemoglobin in *Escherichia coli*/ Methods in Enzymology/(In Press).
Steadman, J. H. et al/Idiopathic Heinze Body Anaemia: HB–Bristol (β67 (E11) VAL→ASP)/ British J. of Haematology/(1970), 18, 435–446.
Anderson, N. L. & Perutz, M. F./Site of the Amino–Acid Substitution in Haemoglobin Seattle ($\alpha^A 2 \beta^{70} 2^{ASP}$)/Nature New Biology/(1973), 243, 274–275.

(List continued on next page.)

Primary Examiner—Mindy Fleisher
Assistant Examiner—Nancy J. Degen
Attorney, Agent, or Firm—Iver P. Cooper

[57] ABSTRACT

Multimeric hemoglobin-like proteins are obtained by crosslinking cysteines of the component tetramers, or by genetically fusing globin-like domains of one tetramer with those of another, by means of an interdomain spacer sequence. Artificial cysteines are introduced selectively in a single globin-like domain per tetramer to control polymerization.

74 Claims, 12 Drawing Sheets

OTHER PUBLICATIONS

Cohen, C. & Parry, D. A. D./α–Helical Coiled Coils and Bundles: How to Design an β–Helical Protein/Proteins: Structure, Function, and Genetics/(1990), 7, 1–15.

Yeager, A. M. et al/Hemoglobin Cheverly: An Unstable Hemoglobin Associated with Chronic Mild Anemia/Pediatr. Res./(1983), 17, 503–507.

Yabuki, A,. et al/Characterization of a Pyridoxalated Hemoglobin–Polyoxyethylene Conjugate as a Physiologic Oxygen Carrier/Transfusion/(1990), 30 (5), 516–520.

Dimarchi, R. et al/Chemical Synthesis of Human Epidermal Growth Factor (EGF) and Human Type α Transforming Growth Factor (TGFα)/Peptides Chemistry and Biology/(1988), Ed. G. R. Marshall/ESCOM, Leiden/202–203.

Dowling, S. et al/A Clinical Study of Fluosol and Hyperbaric Oxygen as an Adjunct to Radiation Therapy/Biomat. Art. Cells. Immobil. Biotech./(1991), 19, 377.

Dickerson, R. E. & Geis, I./Evolution of the Oxygen Carriers/Hemoglobin, Structure, Function, Growth & Pathology/(1983)/Benjamin Cummings Publishing Co. CA/66–114.

Kavanaugh, M. P. et al/Affinity Labeling of Hemoglobin with 4,4'–Diisothiocyanostilbene–2, 2'–Disulfonate: Covalent Cross–Linking in the 2,3–Diphosphoglycerate Binding Site/Biochemistry (1988), 27, 1804–1808.

Hallewel, R. A. et al/Genetically Engineered Polymers of Human CuZn Superoxide Dismutase–Biochemistry and Serum Half–Lives/J. of Biol. Chem./(1989), 264(9), 5260–5268.

Zagloul, T. I. & Doi, R. H./Translational Coupling in *Escherichia coli* of a Heterologous Bacillus *Subtilis–Escherichia coli* Gene Fusion/J. of Bacteriology/(1986), 168(2), 1033–1035.

Imai, K. et al/Studies on the Function of Abnormal Hemoglobins–II. Oxygen Equilibrium of Abnormal Hemoglobins: Shimoneseki, Ube II, Hikari, Gifu, and Agenogi/Biochemimica et Biophysica Acta/(1970), 200, 197–202.

Bonaventura, J. & Riggs, A./Hemoglobin Kansas, A Human Hemoglobin with a Neutral Amino Acid Substitution and an Abnormal Oxygen Equilibrium/J. of Biol. Chem/(1968). 243(5). 980–991.

Ahern, E. et al/Haemoglobin Caribbean β91 (F7) LEU→ARG: A Mildly Unstable Haemoglobin with a Low Oxygen Affinity/FEBS Letters/(1976), 69(1), 99–102.

Tatsis, B. et al/Hemoglobin Pyrgos $\alpha_2\beta_2{}^{83(EF7)GLY \to ASP}$: A New Hemoglobin Variant in Double Heterozygosity with Hemoglobin S/Blood/(1976), 47(5), 827–832.

Sugihara, J. et al/Hemoglobin Rahere, A Human Hemoglobin Variant with Amino Acid Substitution at the 2,3–Diphosphoglycerate Binding Site/J. Clin. Invest./(1985), 76, 1169–1173.

Honig, G. R. et al/Hemoglobin Nigeria (α–81 SER→CYS): A New Variant Associated with α–Thalassemia/Blood/(1980), 55(1), 131–137.

Lewin, B./The Messenger RNA Template/Genes/(1983), Ed. Cell/Publisher–J. Wiley & Sons, NY Chapter 9, 143–162.

Nagel, R. L. et al/Hemoglobin Beth Israel, A Mutant Causing Clinically Apparent Cyanosis/ The New England J. of Med./(1976), 295(3), 125–130.

King, M. A. R./An Unstable Haemoglobin with Reduced Oxygen Affinity: Haemoglobin Peterborough, βIII ($G_{f3}$) Valine→Phenylalanine, its Interaction with Normal Haemoglobijn and with Haemoglobin Lepore/Brit. J. of Haema./(1972), 22, 125–134.

Moo–Penn, W. F. et al/Hemoglobin Presbyterian: β108 (G10) Asparagine→Lysine. A Hemoglobin Variant with Low Oxygen Affinity/FEBS Letters/(1978), 92(1), 53–56.

Konotey–Ahulu, F. I. D. et al/Haemoglobin Korle–Bu (β73 Aspartic Acid→Asparagine)/J. Med. Genet./(1968), 5, 107–111.

Merault, G. et al/Hemoglobin Roseau–Pointe a Pitre $\alpha_2\beta_2$90 (F6) GLU→GLY: A New Hemoglobin Variant with Slight Instability and Low Oxygen Affinity/FEBS Let./(1985), 184(1), 10–13.

Shih, D. T-B. et al/Hemoglobin Chico [β66(E10)LYS→THR]: A New Variant with Decreased Oxygen Affinity/Hemoglobin/(1987), 11(5), 453–464.

Stamatoyannopoulos, G. et al/Physiologic Implications of a Hemoglobin with Decreased Oxygen Affinity (Hemoglobin Seattle)/The New England J. of Med./(1969), 281(17), 915–919.

Degrado, W. F. et al/Protein Design, A Minimalist Approach/Science/(1989), 243, 622–628.

Semchuk, P. D. et al/Synthetic α–Helical Model Proteins: Contribution of Hydrophobic Residues to Protein Stability/Peptides Chemistry, Structure and Biology/Ed. J. E. Rivier & G. R. Marshall/Publisher, Escom–Leiden/(1990), 566–570.

Bennetzen, J. L. & Hall, B. D./Codon Selection in Yeast/The Journal of Biological Chemistry/ (1982), 257(6), 3026–3031.

Tam, L-T. et al/The Hemoglobins of the Bullfrog *Rana Catesbeiana*, The Structure of the β Chain of Component C and the Role of the α Chain in the Formation of Intermolecular Disulfide Bonds/The J. of Biol. Chem./(1986), 261(18), 8290–8294.

Schoner, B. E. et al/Translation of a Synthetic Two–Cistron mRNA in *Escherichia coli*/PNAS/ (1986), 83, 8506–8510.

Riggs, A./Hemoglobin Polymerization in Mice/Science/(1965), 147, 621–623.

Takenaka, O. et al/Hemoglobin Izu(Macaca): β83 (EF 7) GLY→CYS. A New Hemoglobin Variant Found in the Japanese Monkey (*Macaca fuscata*)/Biochim. et Biophys. Acta/(1977), 492, 433–444.

Bonaventura, J. & Riggs, A./Polymerization of Hemoglobins of Mouse and Man: Structural Basis/Science/(1967), 153, 800–802.

Adams, J. G. et al/HB Mississippi [β44(CD3)SER→ARG]: A New Variant with Anomalous Properties/Hemoglobin/(1987), 11(5), 435–452.

Tondo, C. V./Osmometric Study of the Subunit Dissociation of Hemoglobin Porto Alegre [β9(A6)SER→CYS] Dissulfide Polymer/An. Acad. Bras. Bras. Ci.,/(1987), 59(3), 243–251.

Tondo, C. V. et al/Functional Properties of Hemoglobin Porto Alegre ($\alpha_2{}^A\beta_2{}^{9\ SER \to CYS}$) and the Reactivity of its Extra Cysteinyl Residue/Biochim. et Biophys. Acta/(1974), 342, 15–20.

Greer, J. & Perutz, M. F./Three Dimensional Structure of Haemoglobin Rainier/Nature New Biology/(1971), 230, 261–264.

Tam, S-C. & Wong, J. T-F./Impairment of Rental Function by Stroma–Free Hemoglobin in Rats/ J. Lab. Clin. Med./(1988), 111(2), 189–193.

Lee, R. et al/Ultrapure, Stroma–Free, Polymerized Bovine Hemoglobin Solution: Evaluation of Renal Toxicity/J. of Surgical Res./(1989), 47, 407–411.

Bunn, H. F. & Jandi, J. H./The Renal Handling of Hemoglobin II. Catabolism/J. Exp. Med./(1969), 129, 925–936.

Bunn, H. F. et al/The Renal Handling of Hemoglobin I. Glomerular Filtration/J. Exp. Med./ (1969), 129, 909–923.

Holden, S. A. et al./Effect of a PFOB Emulsion (Oxygent) and Carbogen Breathing on the Tumor Cell Survival of the FSaIIC Fibrosarcoma After Treatment with Antitumor Alkylating Agents/Biomat. Art. Cells./(1991), 19(2), 399.

Herman, T. S. & Teicher, B. A./Enhancement of Radiation Therapy by an Experimental Concentrated Perfluorooctylbromide (Oxygent) Emulsion in the Lewis Lung Carcinoma/ Biomat. Art. Cells./(1991), 19(2), 395.

Liebhaber, S. A. et al/Cloning and Complete Nucleotide Sequence of Human 5'-α–Globin Gene/PNAS/(1980), 77(12), 7054–7058.

Devenuto, F. et al/Appraisal of Hemoglobin Solution as a Blood Substitute/Surgery, Gynecology & Obstetrics/(1979), 149, 417–436.

Gould, S. A./The Development of Polymerized Pyridoxylated Hemoglobin Solution as a Red Cell Substitute/Annals of Emerg. Med./(1986), 15(12), 1416/67–1419/70.

Shaanan, B./Structure of Human Oxyhaemoglobin at 2–1 a Resolution/J. Mol. Biol./(1983), 171, 31–59.

Creighton, T. E./Proteins, Structures and Molecular Principles/Figure 3–9/W. H. Freeman & Company, NY No date given.

Hui, A. & Deboer, H. A./Specialized Ribosome System: Preferential Translation of a Single mRNA Species by a Subpopulation of Mutated Ribosomes in *Escherichia coli*/ PNAS/(1987), 84, 4762–4766.

Imamura, T. et al/Hemoglobin Yoshizuka (G10(108)β Asparagine→Aspartic Acid): A New Variant with a Reduced Oxygen Affinity from a Japanese Family/The J. of Clin. Invest./(1969), 48, 2341–2348.

Ohba, Y. et al/Hemoglobin Hirosaki (α 43 [CE 1] PHE→ LEU), A New Unstable Variant/Biochim. et Biophysica Acta/(1975), 405, 155–160.

Beretta, A. et al/Haemoglobin Torino–α43 (CDI) Phenylalanine→Valine/Nature/(1968), 217, 1016–1018.

Knuth, A. et al/Hemoglobin Moabit: Alpha 86 (F7) LEU→ ARG–A New Unstable Abnormal Hemoglobin/Acta Haemat./(1979), 61, 121–124.

Schneider, R. G. et al/Haemoglobin Titusville: α94 ASP→ ASN A New Haemoglobin with a Lowered Affinity for Oxygen/Biochimica et Biophysica Acta/(1975), 400, 365–373.

Moo–Penn, W. F. et al/Hemoglobin Raleigh (β1 Valine→ Acetylalanine). Structural and Functional Characterization/ Biochemistry/(1977), 16(22), 4872–4879.

Moo–Penn, W. F. et al/Hemoglobin Connecticut (β21(B3) ASP→GLY): A Hemoglobin Variant with Low Oxygen Affinity/Am. J. of Hematology/(1981), 11, 137–145.

Gacon, G. et al/Structural and Functional Studies of HB Rothschild β 37 (C3) TRP→ARG A New Variant of the $α_1β_2$ Contact/FEBS Let./(1977), 82(2), 243–246.

Idelson, L. I. et al/New Unstable Haemoglobin (HB Moscva, β24 (B4) GLY→ASP) Found in the USSR/Nature/(1974), 249, 768–770.

Charache, S. et al/Hemoglobin Okaloosa (β48 (CD7) Leucine→Arginine) An Unstable Variant with Low Oxygen Affinity/The J. of Clin. Invest./(1973), 52, 2858–2864.

Efremov, G. D. et al/Hemoglobin Richmond, A Human Hemoglobin Which Forms Asymmetric Hybrids with Other Hemoglobins/The J. of Biological Chemistry/(1969), 244(22), 6105–6116.

Blouquit, Y. et al/Structural Study of Hemoglobin Hazebrouck, β38(C4) THR→PRO A New Abnormal Hemoglobin with Instability and Low Oxygen Affinity/FEBS Let./ (1984) 172(2), 155–158.

Dacie, J. V. et al/Haemoglobin Hammersmith (β 42 (CD1) PHE→Ser)/Nature(1967), 216, 663–665.

Keeling, M. M. et al/Hemoglobin Louisville (β42 (CD1) PHE→LEU): An Unstable Variant Causing Mild Hemolytic Anemia/The J. of Clin. Invest./(1971), 50, 2395–2402.

Bratu, V. et al/Haemoglobin Bucuresti β42 (CDI) PHE→ LEU, A Cause of Unstable Haemoglobin Haemolytic Anaemia/Biochimica et Biophysica Acta/(1971) 251, 1–6.

Arous, N. et al/Hemoglobin Saint Mande β102 (G4) ASN→ TYR: A New Oxygen Affinity Variant/FEBS Let./(1981), 126(1), 114–116.

Garel, M. C. et al/Hemoglobin J Cairo: β 65 (E9) LYS→ GLN, A New Hemoglobin Variant Discovered in an Egyptian Family/Biochim. et Biophys. Acta/(1976), 420, 97–104.

Marinucci, M. et al/Hemoglobin Bologna ($α_2β_2$ 61 (E5) LYS→MET) An Abnormal Human Hemoglobin with Low Oxygen Affinity/Biochim. et Biophys. Acta/(1981), 668, 209–215.

McAlister, L. & Holland M. J./Differential Expression of the Three Yeast Glyceraldehyde–3–Phosphate Dehydrogenase Genes/The J. of Biological Chem./(1985), 260, 15019–15027.

Holland, M. J. et al/The Primary Structures of Two Yeast Enolase Genes/The J. of Biological Chemistry/(1981), 256, 1385–1395.

Holland, J. P. et al/Homologous Nucleotide Sequences at the 5' Termini of Messenger RNAS Synthesized from the Yeast Enolase and Glyceraldehyde–3–Phosphate Dehydrogenase Gene Families/The J. of Biological Chemistry/(1983), 258(8), 5291–5299.

Edens, L. et al/Synthesis and Processing of the Plant Protein Thaumatin in Yeast/Cell/(1984), 37, 629–633.

Kozak, M./Point Mutations Define a Sequence Flanking the AUG Initiator Codon that Modulates Translation by Eukaryotic Ribosomes/Cell/(1986), 44, 283–292.

Cigan, A. M. & Donahue, T. F./Sequence and Structural Features Associated with Translational Initiator Regions in Yeast—A Review/Gene/(1987), 59, 1–18.

Ernst, J. F./Improved Secretion of Heterologous Proteins by Saccharomyces Cerevisiae: Effects of Promoter Substitution in Alpha–Factor Fusions/DNA /(1986), 5(6), 483–491.

Struhl, K. et al/High–Frequency Transformation of Yeast: Autonomous Replication of Hybrid DNA Molecules/PNAS/ (1979), 76, 1035–1039.

Scherer, G. F. E. et al/The Ribosome Binding Sites Recognized by E. Coli Ribosomes Have Regions with Signal Character in Both the Leader and Protein Coding Segments/ Nucleic Acids Research/(1980), 8(17), 3895–3907.

Kastelein, R. A. et al/Effect of the Sequences Upstream from the Ribosome–Binding Site on the Yield of Protein from the Cloned Gene for Phage MS2 Coat Protein/Gene/(1983), 23, 245–254.

Creighton, T. E./Interactions Between Cysteine Residues as Probes of Protein Conformation: The Disulphide Bond Between CYS–and CYS–38 of the Pancreatic Trypsin Inhibitor/J. Mol. Biol./(1975), 96, 767–776.

Creighton, T. E./Effects of Urea and Guanidine HCl on the Folding and Unfolding of Pancreatic Trypsin Inhibitor/J. Mol. Biol./(1977), 113, 313–328.

Ackers, G. K. & Halvorson, H. R./The Link Between Oxygenation and Subunit Dissociation in Human Hemoglobin/PNAS/(1974), 71(11), 4312–4316.

Nagai, K. et al/Trypsin–Catalyzed Synthesis of Peptide Bond in Human Hemoglobin Oxygen Binding Characteristics of GLY–NH$_2$(14$_2\alpha$) HB/The J. of Bio. Chem./(1982), 257, 1622–1625.

Cantor, C. R. & Schimmel, P. R./Biophysical Chemistry/Part 1/The Conformation of Biological Macromolecules/W. H. Freeman & Company, San Francisco/226–269 No date given.

Manning, A. M. et al/Evolution of a Polymeric Globin in the Brine Shrimp Artemia/Nature/ (1990), 348, 653–657.

Chatterjee, R. et al/Isolation and Characterization of a New Hemoglobin Derivative Cross–Linked Between the $\alpha$ Chains (Lysine 99$\alpha_1$→Lysine 99$\alpha_2$)/The J. of Biol. Chem./(1986), 261, 9929–9937.

Schulz, G. E. & Schirmer, R. H./Principles of Protein Structure/Ed. Cantor, C. R./Publisher: Springer–Verlag, NY/(1979)Table 1–2.

Chou, P. Y. & Fasman, G. D../Prediction of Protein Conformation/Biochemistry/ (1974), 13(2), 222–245.

Freedman, R. B. & Hillson, D. A./Formation of Disulphide Bonds/The Enzymology of Post–Translational Modification of Roteins/(1980), vol. 1/Ed.: Freedman, R. B. & Hawkins, H. C./Academic Press/NY 157–212.

Wrightstone, R. N./Policies of the International Hemoglobin Information Center (IHIC) Comprehensive Sickle Cell Center/(1987), 241–308.

Hui, A. et al/Mutagenesis of the Trhee Bases Preceding the Start Codon of the $\beta$–Galac–Tosidase mRNA and its Effect on Translation in *Escherichia coli*/The Embo Journal/ (1984), 3(3), 623–629.

De Boer, H. A., et al/Portable Shine–Dalgarno Regions: A System for a Systematic Study of Defined Alterations of Nucleotide Sequences within E. Coli Ribosome Binding Sites/DNA(1983), 2(3), 231–235.

Shine, J. & Dalgarno, L./Determinant of Cistron Specificity in Bacterial Ribosomes/Nature/ (1975), 254, 34–39.

Harley, C. B. & Reynolds, R. P./Analysis of E. Coli Promoter Sequences/ Nucleic Acids Research/(1987), 15(5), 2343–2361.

Konigsberg, W. & Godson, G. N./Evidence for Use of Rare Codons in the DNAG Gene and other Regulatory Genes of *Escherichia coli*/PNAS(1983), 80, 687–691.

Minnich, V. et al/Hemoglobin Hope: A Beta Chain Variant/Blood/(1965), 25(5), 830–838.

Merault, G. et al/Hemoglobin Roseau–Pointe A Pitre $\alpha_2\beta_2$ 90 (F6) GLU→GLY: A New Hemoglobin Variant with Slight Instability and Low Oxygen Affinity/FEBS Let./ (1985), 184(1), 10–13.

Tschumper, G. & Carbon, J./Sequence of a Yeast DNA Fragment Containing a Chromosomal Replicator and the TRP1 Gene/Gene/(1980), 10, 157–166.

Guthrie, C. & Abelson, J./Organization and Expression of TRNA Genes in Saccharomyces Cerevisiae/The Molecular Biology of the Yeast Saccharomytes Metabolism and Gene Expression/Ed. J. N. Strathern, E. W. Jones, J. R. Broach /Publisher: Cold Spring Harbor Laboratory, NY(1982)487–528.

Schoner, B. et al/Expression of Eukaryotic Genes in *Escherichia coli* with a Synthetic Two Cistron System/ Methods in Enzymology/vol. 153 Recombinant DNA Part D/Ed: Ray Wu & L. Grossman/Academic Press, Inc./NY/ (1987), 401–416.

McCarthy, E. G. et al/Translational Initiation Frequency of ATP Genes from *Escherichia coli*: Identification of an Intercistronic Sequence that Enhances Translation/The Embo Journal/(1985), 4(2), 519–526.

Jones, R. T. et al/Hemoglobin Vancouver [$\alpha_2\beta_2$73(E17) ASP→TYR]: Its Structure and Function/ J. Mol. Evol./ (1976), 9, 37–44.

Feola, M. et al/Nephrotoxicity of Hemoglobin Solutions/ Biomat. Art. Cells, Art. Org./(1990), 18(2), 233–249.

Ishimoto, G. et al/A Variant Hemoglobin Found in Macaca Fuscata: Another Polymerizing Hemoglobin of Macaques/J. Anthorop. Soc. Nippon/(1975), 83(3), 233–243.

Fermi, G. et al/The Crystal Structure of Human Deoxyhaemoglobin at 1–74 A Resolution/ J. Mol. Biol./(1984), 175, 159–174.

Yip, Y. K. et al/Reconstitution of Native Human Hemoglobin from Separated Globin Chains and Alloplex Intermediates/PNAS/(1977), 74(1), 64–68.

Lawn, R. M. et al/The Nucleotide Sequence of the Human $\beta$–Globin Gene/ Cell/(1980), 21, 647–651.

Marotta, C. A. et al/Human $\beta$–Globin Messenger RNA III. Nucleotide Sequences Derived from Complementary DNA/ The J. of Biological Chemistry/ (1977), 252, (14), 5040–5053.

Snyder, S. R. et al/HbXL99$\alpha$: A Hemoglobin Derivative that is Cross–Linked Between the $\alpha$ Subunits is Useful as a Blood Substitute/PNAS/ (1987), 84, 7280–7284.

Benesch, R. & Benesch, R. E./The Effect of Organic Phosphates from the Human Erythrocyte on the Allosteric Properties of Hemolgobin/Biochem. & Biophys. Res. Comm./ (1967), 26(2), 162–167.

Creighton, T. E./Experimental Studies of Protein Folding and Unfolding/Prog. Biophys. Molec. Biol./(1978), 33, 231–297.

Turner, J. W. et al/Characterization of Hemoglobin Burke [$\beta$107 (G9) GLY→ARG]/Biochem. Genetics/(1976), 14(7/8), 577–585.

Schneider, R. G. et al/Hb Mobile [$\alpha_2\beta_2$ 73 (E17) ASP→VAL]: A New Variant/Biochemical Genetics/(1975), 13(7/8), 411–415.

Roberts, T. M. et al/A General Method for Maximizing the Expression of a Cloned Gene/ PNAS(1979), 76(2), 760–764.

Ohba, Y. et al/HB Himeji or $\beta$140 (H18) ALA→ASP A Slightly Unstable Hemoglobin with Increased $\beta$N–Terminal Glycation/Hemoglobin/(1986), 10(2), 109–126.

Ogata, K. et al/Hemoglobin Sendagi ($\beta$42 PHE→VAL) A New Unstable Hemoglobin Variant Having an Amino Acid Substitution at CD1 of the $\beta$–Chain/Hemoglobin/(1986), 10(5), 469–481.

FIG. 2a

```
                    /EcoRI                            /Xmal                    A
                 A  ATT  CGA  GCT  CGG  TAC  CCG  GGC  TAC  ATG  GAG
                    GCT  CGA  GCC  ATG  GGC  CCG  ATG  TAC  CTC SD # 1                                                SD2#
ATT  AAC  TCA  ATC  TAG  AGG  GTA  TTA  ATA  ATG  TAT  CGC  TTA  AAT  AAG  GAG
TAA  TTG  AGT  TAG  ATC  TCC  CAT  AAT  TAT  TAC  ATA  GCG  AAT  TTA  TTC  CTC
                                              Met  Tyr  Arg  Leu  Asn  Lys  Glu
                                              |→       ribosomal loader    →

/NdeI                                /EagI
GAA  TAA  CAT  ATG  CTG  TCT  CCG  GCC  GAT  AAA  ACC  AAC  GTT  AAA  GCT  GCT
CTT  ATT  GTA  TAC  GAC  AGA  GGC  CGG  CTA  TTT  TGG  TTG  CAA  TTT  CGA  CGA
Glu       Met  Leu  Ser  Pro  Ala  Asp  Lys  Thr  Asn  Val  Lys  Ala  Ala
               1    2    3    4    5    6    7    8    9    10   11   12   13
→|        |des-val alpha globin /XhoI
TGG  GGT  AAA  GTT  GGC  GCG  CAC  GCT  GGT  GAA  TAC  GGT  GCT  GAA  GCT  CTC
ACC  CCA  TTT  CAA  CCG  CGC  GTG  CGA  CCA  CTT  ATG  CCA  CGA  CTT  CGA  GAG
Trp  Gly  Lys  Val  Gly  Ala  His  Ala  Gly  Glu  Tyr  Gly  Ala  Glu  Ala  Leu
14   15   16   17   18   19   20   21   22   23   24   25   26   27   28   29

GAG  CGT  ATG  TTC  CTG  TCT  TTC  CCG  ACC  ACC  AAA  ACC  TAC  TTC  CCG  CAC
CTC  GCA  TAC  AAG  GAC  AGA  AAG  GGC  TGG  TGG  TTT  TGG  ATG  AAG  GGC  GTG
Glu  Arg  Met  Phe  Leu  Ser  Phe  Pro  Thr  Thr  Lys  Thr  Tyr  Phe  Pro  His
30   31   32   33   34   35   36   37   38   39   40   41   42   43   44   45

/MstI
TTC  GAC  CTG  TCT  CAC  GGT  TCT  GCG  CAG  GTT  AAA  GGT  CAC  GGT  AAA  AAA
AAG  CTG  GAC  AGA  GTG  CCA  AGA  CGC  GTC  CAA  TTT  CCA  GTG  CCA  TTT  TTT
Phe  Asp  Leu  Ser  His  Gly  Ser  Ala  Gln  Val  Lys  Gly  His  Gly  Lys  Lys
46   47   48   49   50   51   52   53   54   55   56   57   58   59   60   61

GTT  GCT  GAT  GCT  CTG  ACC  AAC  GCT  GTT  GCT  CAC  GTT  GAT  GAT  ATG  CCG
CAA  CGA  CTA  CGA  GAC  TGG  TTG  CGA  CAA  CGA  GTG  CAA  CTA  CTA  TAC  GGC
Val  Ala  Asp  Ala  Leu  Thr  Asn  Ala  Val  Ala  His  Val  Asp  Asp  Met  Pro
62   63   64   65   66   67   68   69   70   71   72   73   74   75   76   77

/MluI
AAC  GCG  TTG  TCT  GCT  CTG  TCT  GAT  CTG  CAC  GCT  CAC  AAA  CTG  CGT  GTT
TTG  CGC  AAC  AGA  CGA  GAC  AGA  CTA  GAC  GTG  CGA  GTG  TTT  GAC  GCA  CAA
Asn  Ala  Leu  Ser  Ala  Leu  Ser  Asp  Leu  His  Ala  His  Lys  Leu  Arg  Val
78   79   80   81   82   83   84   85   86   87   88   89   90   91   92   93
```

FIG. 2b

```
     /HpaI
GAT CCG GTT AAC TTC AAA CTG CTG TCT CAC TGC CTG CTG GTT ACT CTG
CTA GGC CAA TTG AAG TTT GAC GAC AGA GTG ACG GAC GAC CAA TGA GAC
Asp Pro Val Asn Phe Lys Leu Leu Ser His Cys Leu Leu Val Thr Leu
 94  95  96  97  98  99 100 101 102 103 104 105 106 107 108 109

/NaeI
GCT GCT CAT CTG CCG GCT GAA TTT ACC CCG GCT GTT CAT GCG TCT CTG
CGA CGA GTA GAC GGC CGA CTT AAA TGG GGC CGA CAA GTA CGC AGA GAC
Ala Ala His Leu Pro Ala Glu Phe Thr Pro Ala Val His Ala Ser Leu
110 111 112 113 114 115 116 117 118 119 120 121 122 123 124 125

/BstBI
GAT AAA TTC CTG GCT TCT GTT TCT ACC GTT CTG ACT TCG AAA TAC CGT
CTA TTT AAG GAC CGA AGA CAA AGA TGG CAA GAC TGA AGC TTT ATG GCA
Asp Lys Phe Leu Ala Ser Val Ser Thr Val Leu Thr Ser Lys Tyr Arg
126 127 128 129 130 131 132 133 134 135 136 137 138 139 140 141

/EagI
    GGT GTT CTG TCT CCG GCC GAT AAA ACC AAC GTT AAA GCT GCT
    CCA CAA GAC AGA GGC CGG CTA TTT TGG TTG CAA TTT CGA CGA
    Gly Val Leu Ser Pro Ala Asp Lys Thr Asn Val Lys Ala Ala
         1'  2'  3'  4'  5'  6'  7'  8'  9' 10' 11' 12' 13'
    linker
       → second alpha globin →

/XhoI
TGG GGT AAA GTT GGC GCG CAC GCT GGT GAA TAC GGT GCT GAA GCT CTC
ACC CCA TTT CAA CCG CGC GTG CGA CCA CTT ATG CCA CGA CTT CGA GAG
Trp Gly Lys Val Gly Ala His Ala Gly Glu Tyr Gly Ala Glu Ala Leu
14' 15' 16' 17' 18' 19' 20' 21' 22' 23' 24' 25' 26' 27' 28' 29'

GAG CGT ATG TTC CTG TCT TTC CCG ACC ACC AAA ACC TAC TTC CCG CAC
CTC GCA TAC AAG GAC AGA AAG GGC TGG TGG TTT TGG ATG AAG GGC GTG
Glu Arg Met Phe Leu Ser Phe Pro Thr Thr Lys Thr Tyr Phe Pro His
30' 31' 32' 33' 34' 35' 36' 37' 38' 39' 40' 41' 42' 43' 44' 45'
                             /MstI
TTC GAC CTG TCT CAC GGT TCT GCG CAG GTT AAA GGT CAC GGT AAA AAA
AAG CTG GAC AGA GTG CCA AGA CGC GTC CAA TTT CCA GTG CCA TTT TTT
Phe Asp Leu Ser His Gly Ser Ala Gln Val Lys Gly His Gly Lys Lys
46' 47' 48' 49' 50' 51' 52' 53' 54' 55' 56' 57' 58' 59' 60' 61'
```

FIG. 2c

```
         GTT GCT GAT GCT CTG ACC AAC GCT GTT GCT CAC GTT GAT GAT ATG CCG
         CAA CGA CTA CGA GAC TGG TTG CGA CAA CGA GTG CAA CTA CTA TAC GGC
         Val Ala Asp Ala Leu Thr Asn Ala Val Ala His Val Asp Asp Met Pro
         62' 63' 64' 65' 66' 67' 68' 69' 70' 71' 72' 73' 74' 75' 76' 77'

/MluI
         AAC GCG TTG TCT GCT CTG TCT GAT CTG CAC GCT CAC AAA CTG CGT GTT
         TTG CGC AAC AGA CGA GAC AGA CTA GAC GTG CGA GTG TTT GAC GCA CAA
         Asn Ala Leu Ser Ala Leu Ser Asp Leu His Ala His Lys Leu Arg Val
         78' 79' 80' 81' 82' 83' 84' 85' 86' 87' 88' 89' 90' 91' 92' 93'

/HpaI
         GAT CCG GTT AAC TTC AAA CTG CTG TCT CAC TGC CTG CTG GTT ACT CTG
         CTA GGC CAA TTG AAG TTT GAC GAC AGA GTG ACG GAC GAC CAA TGA GAC
         Asp Pro Val Asn Phe Lys Leu Leu Ser His Cys Leu Leu Val Thr Leu
         94' 95' 96' 97' 98' 99' 100'101'102'103'104'105'106'107'108'109'

/NaeI
         GCT GCT CAT CTG CCG GCT GAA TTT ACC CCG GCT GTT CAT GCG TCT CTG
         CGA CGA GTA GAC GGC CGA CTT AAA TGG GGC CGA CAA GTA CGC AGA GAC
         Ala Ala His Leu Pro Ala Glu Phe Thr Pro Ala Val His Ala Ser Leu
         110'111'112'113'114'115'116'117'118'119'120'121'122'123'124'125'

/BstBI
         GAT AAA TTC CTG GCT TCT GTT TCT ACC GTT CTG ACT TCG AAA TAC CGT
         CTA TTT AAG GAC CGA AGA CAA AGA TGG CAA GAC TGA AGC TTT ATG GCA
         Asp Lys Phe Leu Ala Ser Val Ser Thr Val Leu Thr Ser Lys Tyr Arg
         126'127'128'129'130'131'132'133'134'135'136'137'138'139'140'141'
                                                   end of second alpha globin /PstI                                                  B
         TAA TGA    C TGC A             GC TAC ATG GAG ATT AAC TCA
         ATT ACT    G                   ACG TCG ATG TAC CTC TAA TTG AGT SD # 1                                     SD # 2       /NdeI
         ATC TAG AGG GTA TTA ATA ATG TAT CGC TTA AAT AAG GAG GAA TAA CAT
         TAG ATC TCC CAT AAT TAT TAC ATA GCG AAT TTA TTC CTC CTT ATT GTA
                                     Met Tyr Arg Leu Asn Lys Glu Glu
                                     |→      ribosomal loader       →|
```

FIG. 2d

```
                                                        /SacII
ATG  CAC  CTG ACT CCG GAA GAA AAA TCC  GCG GTT ACT GCT CTG TGG GGT
TAC  GTG  GAC TGA GGC CTT CTT TTT AGG  CGC CAA TGA CGA GAC ACC CCA
Met  His  Leu Thr Pro Glu Glu Lys Ser  Ala Val Thr Ala Leu Trp Gly
 1    2    3   4   5   6   7   8   9   10  11  12  13  14  15  16
→ beta globin →

AAA GTG AAC GTT GAC GAA GTT GGT GGT GAA GCT CTG GGA CGT CTG CTG
TTT CAC TTG CAA CTG CTT CAA CCA CCA CTT CGA GAC CCT GCA GAC GAC
Lys Val Asn Val Asp Glu Val Gly Gly Glu Ala Leu Gly Arg Leu Leu
 17  18  19  20  21  22  23  24  25  26  27  28  29  30  31  32

/BglII
GTT GTT TAC CCG TGG ACT CAG CGT  TTC TTT GAA TCT TTC GGA GAT CTG
CAA CAA ATG GGC ACC TGA GTC GCA  AAG AAA CTT AGA AAG CCT CTA GAC
Val Val Tyr Pro Trp Thr Gln Arg  Phe Phe Glu Ser Phe Gly Asp Leu
 33  34  35  36  37  38  39  40   41  42  43  44  45  46  47  48
```

FIG. 2e

```
                                                                          /NcoI
TCT ACC CCG GAC GCT GTT ATG GGT AAC CCG AAA GTT AAA GCC CAT GGT
AGA TGG GGC CTG CGA CAA TAC CCA TTG GGC TTT CAA TTT CGG GTA CCA
Ser Thr Pro Asp Ala Val Met Gly Asn Pro Lys Val Lys Ala His Gly
49  50  51  52  53  54  55  56  57  58  59  60  61  62  63  64

AAA AAA GTT CTG GGT GCT TTC TCT GAC GGT CTG GCT CAC CTG GAC AAC
TTT TTT CAA GAC CCA CGA AAG AGA CTG CCA GAC CGA GTG GAC CTG TTG
Lys Lys Val Leu Gly Ala Phe Ser Asp Gly Leu Ala His Leu Asp Asn
65  66  67  68  69  70  71  72  73  74  75  76  77  78  79  80

/KpnI                                /SacI
CTG AAA GGT ACC TTC GCT ACT CTG TCT GAG CTC CAC TGC GAC AAA CTG
GAC TTT CCA TGG AAG CGA TGA GAC AGA CTC GAG GTG ACG CTG TTT GAC
Leu Lys Gly Thr Phe Ala Thr Leu Ser Glu Leu His Cys Asp Lys Leu
81  82  83  84  85  86  87  88  89  90  91  92  93  94  95  96

/SpeI
CAC GTT GAC CCG GAA AAC TTC CGT CTG CTG GGT AAC GTA CTA GTT TGC
GTG CAA CTG GGC CTT TTG AAG GCA GAC GAC CCA TTG CAT GAT CAA ACG
His Val Asp Pro Glu Asn Phe Arg Leu Leu Gly Asn Val Leu Val Cys
97  98  99  100 101 102 103 104 105 106 107 108 109 110 111 112

/EcoRI
GTT CTG GCT CAC CAC TTC GGT AAA GAA TTC ACT CCG CCG GTT CAG GCT
CAA GAC CGA GTG GTG AAG CCA TTT CTT AAG TGA GGC GGC CAA GTC CGA
Val Leu Ala His His Phe Gly Lys Glu Phe Thr Pro Pro Val Gln Ala
113 114 115 116 117 118 119 120 121 122 123 124 125 126 127 128

GCT TAC CAG AAA GTT GTT GCT GGT GTT GCT AAC GCG CTA GCT CAC AAA
CGA ATG GTC TTT CAA CAA CGA CCA CAA CGA TTG CGC GAT CGA GTG TTT
Ala Tyr Gln Lys Val Val Ala Gly Val Ala Asn Ala Leu Ala His Lys
129 130 131 132 133 134 135 136 137 138 139 140 141 142 143 144

/HindIII
TAC CAC TAA TGA
ATG GTG ATT ACT TCG A
Tyr His
145 146
End beta globin +
```

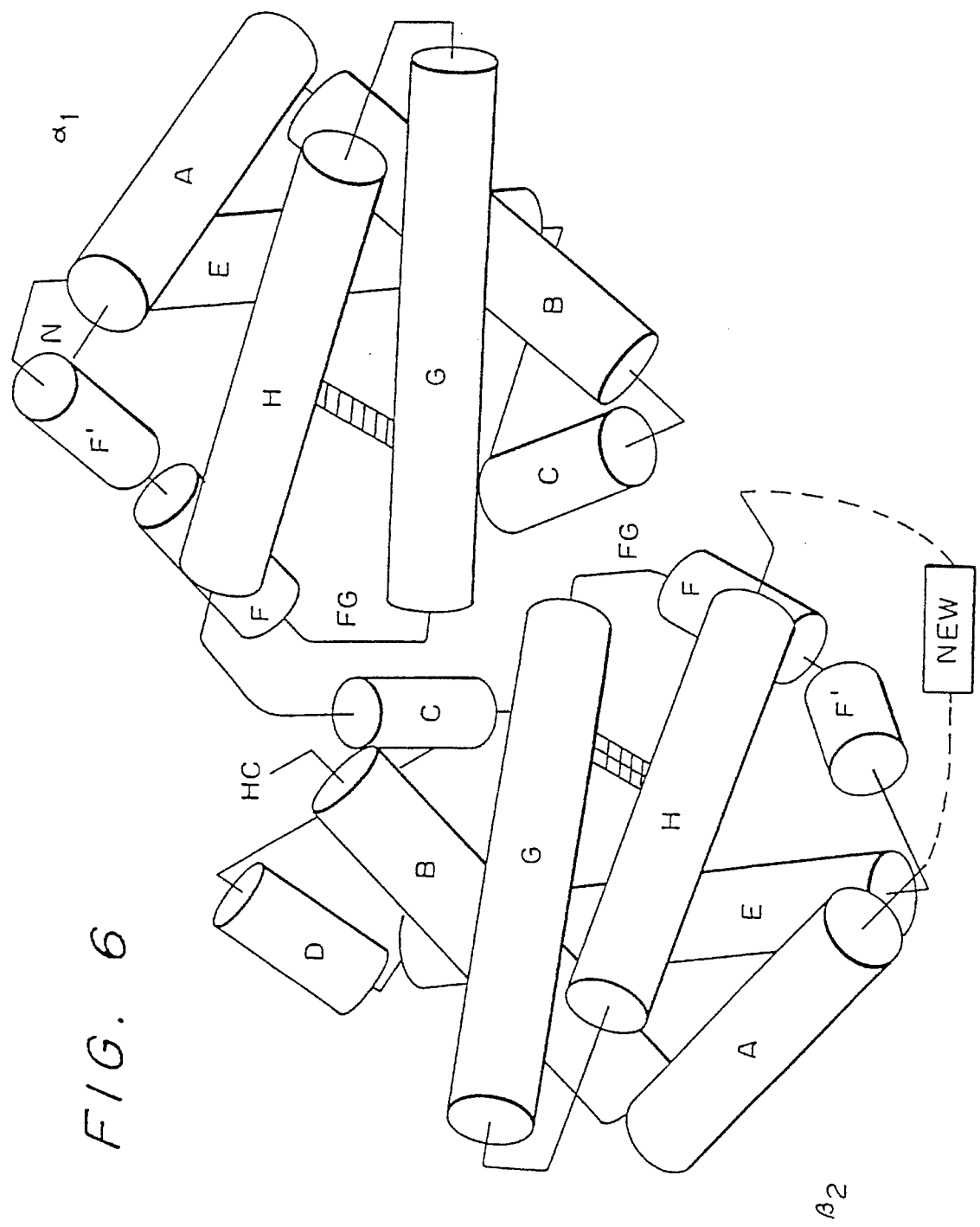

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 1464 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
AATTCGAGCT  CGGTACCCGG  GCTACATGGA  GATTAACTCA  ATCTAGAGGG  TATTAATAAT    60
GTATCGCTTA  AATAAGGAGG  AATAACATAT  GCTGTCTCCG  GCCGATAAAA  CCAACGTTAA   120
AGCTGCTTGG  GGTAAAGTTG  CGCGCACGC   TGGTGAATAC  GGTGCTGAAG  CTCTCGAGCG   180
TATGTTCCTG  TCTTTCCCGA  CCACCAAAAC  CTACTTCCCG  CACTTCGACC  TGTCTCACGG   240
TTCTGCGCAG  GTTAAAGGTC  ACGGTAAAAA  AGTTGCTGAT  GCTCTGACCA  ACGCTGTTGC   300
TCACGTTGAT  GATATGCCGA  ACGCGTTGTC  TGCTCTGTCT  GATCTGCACG  CTCACAAACT   360
GCGTGTTGAT  CCGGTTAACT  TCAAACTGCT  GTCTCACTGC  TGCTGGTTA   CTCTGGCTGC   420
TCATCTGCCG  GCTGAATTTA  CCCCGGCTGT  TCATGCGTCT  CTGGATAAAT  TCCTGGCTTC   480
TGTTTCTACC  GTTCTGACTT  CGAAATACCG  TGGTGTTCTG  TCTCCGGCCG  ATAAAACCAA   540
CGTTAAAGCT  GCTTGGGGTA  AAGTTGGCGC  GCACGCTGGT  GAATACGGTG  CTGAAGCTCT   600
CGAGCGTATG  TTCCTGTCTT  TCCCGACCAC  CAAAACCTAC  TTCCCGCACT  TCGACCTGTC   660
TCACGGTTCT  GCGCAGGTTA  AAGGTCACGG  TAAAAAAGTT  GCTGATGCTC  TGACCAACGC   720
TGTTGCTCAC  GTTGATGATA  TGCCGAACGC  GTTGTCTGCT  CTGTCTGATC  TGCACGCTCA   780
CAAACTGCGT  GTTGATCCGG  TTAACTTCAA  ACTGCTGTCT  CACTGCCTGC  TGGTTACTCT   840
GGCTGCTCAT  CTGCCGGCTG  AATTTACCCC  GGCTGTTCAT  GCGTCTCTGG  ATAAATTCCT   900
GGCTTCTGTT  TCTACCGTTC  TGACTTCGAA  ATACCGTTAA  TGACTGCAGC  TACATGGAGA   960
TTAACTCAAT  CTAGAGGGTA  TTAATAATGT  ATCGCTTAAA  TAAGGAGGAA  TAACATATGC  1020
ACCTGACTCC  GGAAGAAAAA  TCCGCGGTTA  CTGCTCTGTG  GGGTAAAGTG  AACGTTGACG  1080
AAGTTGGTGG  TGAAGCTCTG  GGACGTCTGC  TGGTTGTTTA  CCCGTGGACT  CAGCGTTTCT  1140
TTGAATCTTT  CGGAGATCTG  TCTACCCCGG  ACGCTGTTAT  GGGTAACCCG  AAAGTTAAAG  1200
CCCATGGTAA  AAAAGTTCTG  GGTGCTTTCT  CTGACGGTCT  GGCTCACCTG  GACAACCTGA  1260
AAGGTACCTT  CGCTACTCTG  TCTGAGCTCC  ACTGCGACAA  ACTGCACGTT  GACCCGGAAA  1320
ACTTCCGTCT  GCTGGGTAAA  GTACTAGTTT  GCGTTCTGGC  TCACCACTTC  GGTAAAGAAT  1380
TCACTCCGCC  GGTTCAGGCT  GCTTACCAGA  AAGTTGTTGC  TGGTGTTGCT  AACGCGCTAG  1440
CTCACAAATA  CCACTAATGA  AGCT                                            1464
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ile Glu Gly Arg
1

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Val His Leu Thr Pro
1                   5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Ser Lys Tyr Arg
1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Val Leu Ser Pro
1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

His Lys Tyr His
1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Val His Leu Thr
1

( 2 ) INFORMATION FOR SEQ ID NO:8:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Lys Cys Ala Glu Leu Glu Gly Arg Leu Glu Ala Leu Glu Gly Arg Leu
1               5                   10                  15
Glu Ala Leu Glu Gly Arg Leu Glu Ala Leu Glu Gly Arg Leu Glu Ala
                20                  25                  30
Leu Glu Gly Lys Leu
            35

( 2 ) INFORMATION FOR SEQ ID NO:9:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

Gly Glu Leu Glu Glu Leu Leu Lys Lys Leu Lys Glu Leu Leu Lys Gly
1               5                   10                  15

( 2 ) INFORMATION FOR SEQ ID NO:10:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

GAAGCCAUGG                                                                10

( 2 ) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Ile Glu Gly Arg
1

( 2 ) INFORMATION FOR SEQ ID NO:12:

( i ) SEQUENCE CHARACTERISTICS:
    ( A ) LENGTH: 31 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GCGGCCGCGG AAGAGTCAAT TCAGGAGGGT G 31

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GCCGGCCGTC ACTGCCCGCT TTCCAGTCGG GAA 33

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CCGAACGCGT TGTGCGCTCT GTCTGAT 27

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GGTGCTCACG TTGATTGCAT GCCGAACGCG 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CTGACCAACG CTGTTTGCCA CGTTGATGAT 30

( 2 ) INFORMATION FOR SEQ ID NO:17:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

| Val<br>1 | Leu | Ser | Pro | Ala<br>5 | Asp | Lys | Thr | Asn | Val<br>10 | Lys | Ala | Ala | Trp | Gly<br>15 | Lys |
|---|---|---|---|---|---|---|---|---|---|---|---|---|---|---|---|
| Val | Gly | Ala | His<br>20 | Ala | Gly | Glu | Tyr | Gly<br>25 | Ala | Glu | Ala | Leu | Glu<br>30 | Arg | Met |
| Phe | Leu | Ser<br>35 | Phe | Pro | Thr | Thr | Lys<br>40 | Thr | Tyr | Phe | Pro | His<br>45 | Phe | Asp | Leu |
| Ser | His<br>50 | Gly | Ser | Ala | Gln<br>55 | Val | Lys | Gly | His | Gly<br>60 | Lys | Lys | Val | Ala | Asp |
| Ala<br>65 | Leu | Thr | Asn | Ala | Val<br>70 | Ala | His | Val | Asp | Asp<br>75 | Met | Pro | Asn | Ala | Leu<br>80 |
| Ser | Ala | Leu | Ser | Asp<br>85 | Leu | His | Ala | His | Lys<br>90 | Leu | Arg | Val | Asp | Pro<br>95 | Val |
| Asn | Phe | Lys | Leu<br>100 | Leu | Ser | His | Cys | Leu<br>105 | Leu | Val | Thr | Leu | Ala<br>110 | Ala | His |
| Leu | Pro | Ala<br>115 | Glu | Phe | Thr | Pro | Ala<br>120 | Val | His | Ala | Ser | Leu<br>125 | Asp | Lys | Phe |
| Leu | Ala<br>130 | Ser | Val | Ser | Thr | Val<br>135 | Leu | Thr | Ser | Lys | Tyr<br>140 | Arg | | | |

( 2 ) INFORMATION FOR SEQ ID NO:18:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

| Ser<br>1 | Leu | Thr | Lys | Thr<br>5 | Glu | Arg | Thr | Ile | Ile<br>10 | Val | Ser | Met | Trp | Ala<br>15 | Lys |
|---|---|---|---|---|---|---|---|---|---|---|---|---|---|---|---|
| Ile | Ser | Thr | Gln<br>20 | Ala | Asp | Thr | Ile | Gly<br>25 | Thr | Glu | Thr | Leu | Glu<br>30 | Arg | Leu |
| Phe | Leu | Ser<br>35 | His | Pro | Gln | Thr | Lys<br>40 | Thr | Tyr | Phe | Pro | His<br>45 | Phe | Asp | Leu |
| His | Pro<br>50 | Gly | Ser | Ala | Gln<br>55 | Leu | Arg | Ala | His | Gly<br>60 | Ser | Lys | Val | Val | Ala |
| Ala<br>65 | Val | Gly | Asp | Ala | Val<br>70 | Lys | Ser | Ile | Asp | Asp<br>75 | Ile | Gly | Gly | Ala | Leu<br>80 |
| Ser | Lys | Leu | Ser | Glu<br>85 | Leu | His | Ala | Tyr | Ile<br>90 | Leu | Arg | Val | Asp | Pro<br>95 | Val |
| Asn | Phe | Lys | Leu<br>100 | Leu | Ser | His | Cys | Leu<br>105 | Leu | Val | Thr | Leu | Ala<br>110 | Ala | Arg |
| Phe | Pro | Ala<br>115 | Asp | Phe | Thr | Ala | Glu<br>120 | Ala | His | Ala | Ala | Trp<br>125 | Asp | Lys | Phe |
| Leu | Ser<br>130 | Val | Val | Ser | Ser | Val<br>135 | Leu | Thr | Glu | Lys | Tyr<br>140 | Arg | | | |

( 2 ) INFORMATION FOR SEQ ID NO:19:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

| | | | | | | | | | | | | | | | |
|---|---|---|---|---|---|---|---|---|---|---|---|---|---|---|---|
| Val 1 | His | Leu | Thr | Pro 5 | Glu | Glu | Lys | Ser | Ala 10 | Val | Thr | Ala | Leu | Trp 15 | Gly |
| Lys | Val | Asn | Val 20 | Asp | Glu | Val | Gly | Gly 25 | Glu | Ala | Leu | Gly | Arg 30 | Leu | Leu |
| Val | Val | Tyr 35 | Pro | Trp | Thr | Gln | Arg 40 | Phe | Phe | Glu | Ser | Phe 45 | Gly | Asp | Leu |
| Ser | Thr 50 | Pro | Asp | Ala | Val | Met 55 | Gly | Asn | Pro | Lys | Val 60 | Lys | Ala | His | Gly |
| Lys 65 | Lys | Val | Leu | Gly | Ala 70 | Phe | Ser | Asp | Gly | Leu 75 | Ala | His | Leu | Asp | Asn 80 |
| Leu | Lys | Gly | Thr | Phe 85 | Ala | Thr | Leu | Ser | Glu 90 | Leu | His | Cys | Asp | Lys 95 | Leu |
| His | Val | Asp | Pro 100 | Glu | Asn | Phe | Arg | Leu 105 | Leu | Gly | Asn | Val | Leu 110 | Val | Cys |
| Val | Leu | Ala 115 | His | His | Phe | Gly | Lys 120 | Glu | Phe | Thr | Pro | Pro 125 | Val | Gln | Ala |
| Ala | Tyr 130 | Gln | Lys | Val | Val | Ala 135 | Gly | Val | Ala | Asn | Ala 140 | Leu | Ala | His | Lys |
| Tyr 145 | His | | | | | | | | | | | | | | |

( 2 ) INFORMATION FOR SEQ ID NO:20:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

| | | | | | | | | | | | | | | | |
|---|---|---|---|---|---|---|---|---|---|---|---|---|---|---|---|
| Val 1 | His | Leu | Thr | Pro 5 | Glu | Glu | Lys | Thr | Ala 10 | Val | Asn | Ala | Leu | Trp 15 | Gly |
| Lys | Val | Asn | Val 20 | Asp | Ala | Val | Gly | Gly 25 | Glu | Ala | Leu | Gly | Arg 30 | Leu | Leu |
| Val | Val | Tyr 35 | Pro | Trp | Thr | Gln | Arg 40 | Phe | Phe | Glu | Ser | Phe 45 | Gly | Asp | Leu |
| Ser | Ser 50 | Pro | Asp | Ala | Val | Met 55 | Gly | Asn | Pro | Lys | Val 60 | Lys | Ala | His | Gly |
| Lys 65 | Lys | Val | Leu | Gly | Ala 70 | Phe | Ser | Asp | Gly | Leu 75 | Ala | His | Leu | Asp | Asn 80 |
| Leu | Lys | Gly | Thr | Phe 85 | Ser | Gln | Leu | Ser | Glu 90 | Leu | His | Cys | Asp | Lys 95 | Leu |
| His | Val | Asp | Pro 100 | Glu | Asn | Phe | Arg | Leu 105 | Leu | Gly | Asn | Val | Leu 110 | Val | Cys |
| Val | Leu | Ala 115 | Arg | Asn | Phe | Gly | Lys 120 | Glu | Phe | Thr | Pro | Gln 125 | Met | Gln | Ala |
| Ala | Tyr 130 | Gln | Lys | Val | Val | Ala 135 | Gly | Val | Ala | Asn | Ala 140 | Leu | Ala | His | Lys |
| Tyr 145 | His | | | | | | | | | | | | | | |

( 2 ) INFORMATION FOR SEQ ID NO:21:

( i ) SEQUENCE CHARACTERISTICS:

(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

```
Gly His Phe Thr Glu Glu Asp Lys Ala Thr Ile Thr Ser Leu Trp Gly
 1               5                  10                  15
Lys Val Asn Val Glu Asp Ala Gly Gly Glu Thr Leu Gly Arg Leu Leu
            20                  25                  30
Val Val Tyr Pro Trp Thr Gln Arg Phe Phe Asp Ser Phe Gly Asn Leu
        35                  40                  45
Ser Ser Ala Ser Ala Ile Met Gly Asn Pro Lys Val Lys Ala His Gly
    50                  55                  60
Lys Lys Val Leu Thr Ser Leu Gly Asp Ala Ile Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
            100                 105                 110
Val Leu Ala Ile His Phe Gly Lys Glu Phe Thr Pro Glu Val Gln Ala
        115                 120                 125
Ser Trp Gln Lys Met Val Thr Ala Val Ala Ser Ala Leu Ser Ser Arg
    130                 135                 140
Tyr His
145
```

(2) INFORMATION FOR SEQ ID NO:22:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

```
Gly His Phe Thr Glu Glu Asp Lys Ala Thr Ile Thr Ser Leu Trp Gly
 1               5                  10                  15
Lys Val Asn Val Glu Asp Ala Gly Gly Glu Thr Leu Gly Arg Leu Leu
            20                  25                  30
Val Val Tyr Pro Trp Thr Gln Arg Phe Phe Asp Ser Phe Gly Asn Leu
        35                  40                  45
Ser Ser Ala Ser Ala Ile Met Gly Asn Pro Lys Val Lys Ala His Gly
    50                  55                  60
Lys Lys Val Leu Thr Ser Leu Gly Asp Ala Ile Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
            100                 105                 110
Val Leu Ala Ile His Phe Gly Lys Glu Phe Thr Pro Glu Val Gln Ala
        115                 120                 125
Ser Trp Gln Lys Met Val Thr Gly Val Ala Ser Ala Leu Ser Ser Arg
    130                 135                 140
Tyr His
```

(2) INFORMATION FOR SEQ ID NO:23:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Gly His Phe Thr Glu Glu Asp Lys Ala Thr Ile Thr Ser Leu Trp Gly
 1               5                  10                  15
Lys Val Asn Val Glu Asp Ala Gly Gly Glu Thr Leu Gly Arg Leu Leu
                20                  25                  30
Val Val Tyr Pro Trp Thr Gln Arg Phe Phe Asp Ser Phe Gly Asn Leu
            35                  40                  45
Ser Ser Ala Ser Ala Ile Met Gly Asn Pro Lys Val Lys Ala His Gly
        50                  55                  60
Lys Lys Val Leu Thr Ser Leu Gly Asp Ala Thr Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
               100                 105                 110
Val Leu Ala Ile His Phe Gly Lys Glu Phe Thr Pro Glu Val Gln Ala
           115                 120                 125
Ser Trp Gln Lys Met Val Thr Ala Val Ala Ser Ala Leu Ser Ser Arg
       130                 135                 140
Tyr His
145
```

(2) INFORMATION FOR SEQ ID NO:24:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Val His Phe Thr Ala Glu Glu Lys Ala Ala Val Thr Ser Leu Trp Ser
 1               5                  10                  15
Lys Met Asn Val Glu Glu Ala Gly Gly Glu Ala Leu Gly Arg Leu Leu
                20                  25                  30
Val Val Tyr Pro Trp Thr Gln Arg Phe Phe Asp Ser Phe Gly Asn Leu
            35                  40                  45
Ser Ser Pro Ser Ala Ile Leu Gly Asn Pro Lys Val Lys Ala His Gly
        50                  55                  60
Lys Lys Val Leu Thr Ser Phe Gly Asp Ala Ile Lys Asn Met Asp Asn
65                  70                  75                  80
Leu Lys Pro Ala Phe Ala Lys Leu Ser Glu Leu His Cys Asp Lys Leu
                85                  90                  95
His Val Asp Pro Glu Asn Phe Lys Leu Leu Gly Asn Val Met Val Ile
               100                 105                 110
Ile Leu Ala Thr His Phe Gly Lys Glu Phe Thr Pro Glu Val Gln Ala
```

115                          120                              125
        Ala  Trp  Gln  Lys  Leu  Val  Ser  Ala  Val  Ala  Ile  Ala  Leu  Ala  His  Lys
             130                          135                      140

Tyr  His
        145

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Met  Tyr  Arg  Leu  Asn  Lys  Glu  Glu
        1                   5

( 2 ) INFORMATION FOR SEQ ID NO:26:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Met  Leu  Ser  Pro  Ala  Asp  Lys  Thr  Asn  Val  Lys  Ala  Ala  Trp  Gly  Lys
        1                   5                        10                           15

Val  Gly  Ala  His  Ala  Gly  Glu  Tyr  Gly  Ala  Glu  Ala  Leu  Glu  Arg  Met
                       20                        25                           30

Phe  Leu  Ser  Phe  Pro  Thr  Thr  Lys  Thr  Tyr  Phe  Pro  His  Phe  Asp  Leu
                  35                        40                       45

Ser  His  Gly  Ser  Ala  Gln  Val  Lys  Gly  His  Gly  Lys  Lys  Val  Ala  Asp
             50                        55                       60

Ala  Leu  Thr  Asn  Ala  Val  Ala  His  Val  Asp  Asp  Met  Pro  Asn  Ala  Leu
        65                       70                       75                           80

Ser  Ala  Leu  Ser  Asp  Leu  His  Ala  His  Lys  Leu  Arg  Val  Asp  Pro  Val
                            85                       90                           95

Asn  Phe  Lys  Leu  Leu  Ser  His  Cys  Leu  Leu  Val  Thr  Leu  Ala  Ala  His
                       100                      105                          110

Leu  Pro  Ala  Glu  Phe  Thr  Pro  Ala  Val  His  Ala  Ser  Leu  Asp  Lys  Phe
                       115                      120                          125

Leu  Ala  Ser  Val  Ser  Thr  Val  Leu  Thr  Ser  Lys  Tyr  Arg
                  130                      135                      140

( 2 ) INFORMATION FOR SEQ ID NO:27:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Val  Leu  Ser  Pro  Ala  Asp  Lys  Thr  Asn  Val  Lys  Ala  Ala  Trp  Gly  Lys
        1                   5                        10                           15

```
Val Gly Ala His Ala Gly Glu Tyr Gly Ala Glu Ala Leu Glu Arg Met
         20                  25                  30

Phe Leu Ser Phe Pro Thr Thr Lys Thr Tyr Phe Pro His Phe Asp Leu
         35                  40                  45

Ser His Gly Ser Ala Gln Val Lys Gly His Gly Lys Lys Val Ala Asp
         50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
             100                 105                 110

Leu Pro Ala Glu Phe Thr Pro Ala Val His Ala Ser Leu Asp Lys Phe
             115                 120                 125

Leu Ala Ser Val Ser Thr Val Leu Thr Ser Lys Tyr Arg
             130                 135                 140
```

( 2 ) INFORMATION FOR SEQ ID NO:28:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Met His Leu Thr Pro Glu Glu Lys Ser Ala Val Thr Ala Leu Trp Gly
 1                5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
             35                  40                  45

Ser Thr Pro Asp Ala Val Met Gly Asn Pro Lys Val Lys Ala His Gly
         50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Lys Val Leu Val Cys
             100                 105                 110

Val Leu Ala His His Phe Gly Lys Glu Phe Thr Pro Pro Val Gln Ala
             115                 120                 125

Ala Tyr Gln Lys Val Val Ala Gly Val Ala Asn Ala Leu Ala His Lys
             130                 135                 140

Tyr His
145
```

( 2 ) INFORMATION FOR SEQ ID NO:29:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note=one or both of Gly residues 131 and 132 can be absent; one or both
of Gly residues 147 and 148 can be absent ( x i ) SEQUENCE DESCRIPTION: SEQ ID NO:29:

| Met | Leu | Ser | Pro | Ala | Asp | Lys | Thr | Asn | Val | Lys | Ala | Ala | Trp | Gly | Gly |
| 1 | | | | 5 | | | | | 10 | | | | | | 15 |

| Gly | Tyr | Pro | Trp | Thr | Gln | Arg | Phe | Phe | Glu | Ser | Phe | Gly | Asp | Leu | Ser |
| | | | 20 | | | | | 25 | | | | | 30 | | |

| Thr | Pro | Asp | Ala | Val | Met | Gly | Asn | Pro | Lys | Val | Lys | Ala | His | Gly | Lys |
| | | 35 | | | | | 40 | | | | | 45 | | | |

| Lys | Val | Leu | Gly | Ala | Phe | Ser | Asp | Gly | Leu | Ala | His | Leu | Asp | Asn | Leu |
| | | 50 | | | | 55 | | | | | 60 | | | | |

| Lys | Gly | Thr | Phe | Ala | Thr | Leu | Ser | Glu | Leu | His | Cys | Asp | Lys | Leu | His |
| 65 | | | | | 70 | | | | | 75 | | | | | 80 |

| Val | Asp | Pro | Glu | Asn | Phe | Arg | Leu | Leu | Gly | Lys | Val | Leu | Val | Cys | Val |
| | | | | 85 | | | | | 90 | | | | | 95 | |

| Leu | Ala | His | His | Phe | Gly | Lys | Glu | Phe | Thr | Pro | Pro | Val | Gln | Ala | Ala |
| | | | 100 | | | | | 105 | | | | | 110 | | |

| Tyr | Gln | Lys | Val | Val | Ala | Gly | Val | Ala | Asn | Ala | Leu | Ala | His | Lys | Tyr |
| | | 115 | | | | | 120 | | | | | 125 | | | |

| His | Gly | Gly | Gly | Ala | Ala | Ala | Ala | Ala | Ala | Ala | Ala | Ala | Ala | Ala | Ala |
| | 130 | | | | | 135 | | | | | 140 | | | | |

| Ala | Gly | Gly | Gly | Met | His | Leu | Thr | Pro | Glu | Glu | Lys | Ser | Ala | Val | Thr |
| 145 | | | | | 150 | | | | | 155 | | | | | 160 |

| Ala | Leu | Trp | Gly | Lys | Val | Asn | Val | Asp | Glu | Val | Gly | Gly | Glu | Ala | Leu |
| | | | | 165 | | | | | 170 | | | | | 175 | |

| Gly | Arg | Leu | Leu | Val | Val |
| | | | 180 | | |

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

| Leu | Arg | Arg | Gln | Ile | Asp | Leu | Glu | Val | Thr | Gly | Leu |
| 1 | | | | 5 | | | | | 10 | | |

( 2 ) INFORMATION FOR SEQ ID NO:31:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

| Lys | Cys | Ala | Glu | Leu | Glu | Gly | Lys | Leu | Glu | Ala | Leu | Glu | Gly | Lys | Leu |
| 1 | | | | 5 | | | | | 10 | | | | | 15 | |

| Glu | Ala | Leu | Glu | Gly | Lys | Leu | Glu | Ala | Leu | Glu | Gly | Lys | Leu | Glu | Ala |
| | | | 20 | | | | | 25 | | | | | 30 | | |

| Leu | Glu | Gly |
| | | 35 |

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
Gly  Gly  Gly  Gly  Gly  Gly  Gly
 1                 5
```

( 2 ) INFORMATION FOR SEQ ID NO:33:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note=one or both of Gly
            residues 2 and 3 can be absent; one or both
            of Gly residues 17 and 18 can be absent ( x i ) SEQUENCE DESCRIPTION: SEQ ID NO:33:

```
Gly  Gly  Gly  Ala  Ala  Ala  Ala  Ala  Ala  Ala  Ala  Ala  Ala  Ala  Gly
 1                 5                          10                      15
Gly  Gly
```

( 2 ) INFORMATION FOR SEQ ID NO:34:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note=one or both of Gly
            residues 2 and 3 can be absent; any or all
            of Pro residues 16, 17, 18 and 19 can be
            absent; one or both of Gly residues 22 and
            23 can be absent ( x i ) SEQUENCE DESCRIPTION: SEQ ID NO:34:

```
Gly  Gly  Gly  Pro  Pro  Pro  Pro  Pro  Pro  Pro  Pro  Pro  Pro  Pro  Pro
 1                 5                          10                      15
Pro  Pro  Pro  Gly  Gly  Gly
                20
```

( 2 ) INFORMATION FOR SEQ ID NO:35:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i x ) FEATURE:
        ( D ) OTHER INFORMATION: /note=one or both of Gly
            residues 2 and 3 can be absent; any or all
            of Asp residues 5-33 can be absent; one
            or both of Gly residues 35 and 36 can be
            absent (ii) MOLECULE TYPE: peptide (xi) SEQUENCE DESCRIPTION: SEQ ID NO:35:

```
Gly Gly Gly Asp Asp Asp Asp Asp Asp Asp Asp Asp Asp Asp Asp
 1               5                      10                  15
Asp Asp Asp Asp Asp Asp Asp Asp Asp Asp Asp Asp Asp Asp Asp
            20                      25                  30
Asp Gly Gly Gly
        35
```

PRODUCTION AND USE OF MULTIMERIC HEMOGLOBINS

This application is a continuation-in-part of Ser. No. 07/789,179, filed Nov. 8, 1991, which is a continuation-in-part of Ser. No. 07/671,707, filed Apr. 1, 1991, now abandoned, which is the national stage of PCT/US90/02654, filed May 10, 1990, which is a continuation-in-part of a Looker and Hoffman, U.S. Ser. No. 07/374,161, DI-ALPHA AND DI-BETA GLOBIN LIKE POLYPEPTIDES AND USES THEREFOR, filed Jun. 30, 1989, now abandoned; (b) Stetler and Wagenbach, U.S. Ser. No. 07/379,116, PRODUCTION OF HUMAN HEMOGLOBIN BY TRANSFORMED YEAST CELLS, filed Jul. 13, 1989, now abandoned; and (c) Hoffman, Looker, Rosendahl and Stetler, U.S. Ser. No. 07/349,623, POLYCISTRONIC CO-EXPRESSION OF THE ALPHA- AND BETA-GLOBINS AND IN VIVO ASSEMBLY OF BIOLOGICALLY ACTIVE, TETRAMERIC HEMOGLOBIN, filed May 10, 1989, now abandoned; all owned by Somatogen, Inc.

CROSS-REFERENCE TO RELATED APPLICATIONS

Hoffman and Nagai, U.S. Ser. No. 07/194,338, filed May 10, 1988, now U.S. Pat. No. 5,028,588, presently owned by Somatogen, Inc., relates to the use of low oxygen affinity and other mutant hemoglobins as blood substitutes, and to the expression of alpha and beta globin in nonerythroid cells. Hoffman and Nagai, U.S. Ser. No. 07/443,950, filed Dec. 1, 1989, discloses certain additional dicysteine hemoglobin mutants; it is a continuation-in-part of 07/194,338. Anderson, et al., HEMOGLOBINS AS DRUG DELIVERY AGENTS, Ser. No. 07/789,177, filed Nov. 8, 1991, discloses use of conjugation of hemoglobins with drugs as a means for delivery of the drug to a patient.

BACKGROUND OF THE INVENTION

Field of the Invention

The present invention is directed to multimeric hemoglobin-like proteins composed of two or more pseudotetramers linked together either by genetic fusion or by chemical crosslinking.

Description of the Background Art
A. Structure and Function of Hemoglobin

Hemoglobin (Hgb) is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is susceptible to oxidation, but may be reduced again by one of two enzyme systems within the erythrocyte, the cytochrome $b_5$ and glutathione reduction systems.

The structure of hemoglobin is well known. We herewith incorporate by reference the entire text of Bunn and Forget, eds., *Hemoglobin: Molecular, Genetic and Clinical Aspects* (W. B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981).

About 92% of the normal adult human hemolysate is Hgb A (designated alpha2 beta2, because it comprises two alpha and two beta chains). Other recognized hemoglobin species are Hgb $A_2$ ($\alpha_2 \delta_2$), Hgb $A_{1a}$, Hgb $A_{1b}$, and Hgb $A_{1c}$, as well as the rare species Hgb F ($\alpha_2$ gamma$_2$), Hgb Gower-1 (Zeta$_2$ epsilon$_2$), Hgb Gower-2 (alpha$_2$ epsilon$_2$), Hgb Portland (Zeta$_2$ gamma$_2$), and Hgb H (beta$_4$) and Hgb Bart (gamma$_4$). They are distinguished from Hgb A by a different selection of polypeptide chains.

The primary structure of a polypeptide is defined by its amino acid sequence and by identification of any modifications of the side chains of the individual amino acids. The amino acid sequences of both the alpha and beta globin polypeptide chains of "normal" human hemoglobin is given in Table 1. Many mutant forms are also known; several mutants are identified in Table 400. The wild-type alpha chain consists of 141 amino acids. The iron atom of the heme (ferroprotoporphyrin IX) group is bound covalently to the imidazole of His 87 (the "proximal histidine"). The wild-type beta chain is 146 residues long and heme is bound to it at His 92. Apohemoglobin is the heme-free analogue of hemoglobin; it exists predominantly as the $\alpha\beta$-globin dimer.

Segments of polypeptide chains may be stabilized by folding into one of two common conformations, the alpha helix and the beta pleated sheet. In its native state, about 75% of the hemoglobin molecule is alpha-helical. Alpha-helical segments are separated by segments wherein the chain is less constrained. It is conventional to identify the alpha-helical segments of each chain by letters, e.g., the proximal histidine of the alpha chain is F8 (residue 8 of helix F). The non-helical segments are identified by letter pairs, indicating which helical segments they connect. Thus, non-helical segment BC lies between helix B and helix C. In comparing two variants of a particular hemoglobin chain, it may be enlightening to attempt to align the helical segments when seeking to find structural homologies. For the amino acid sequence and helical residue notation for normal human hemoglobin $A_o$ alpha and beta chains, see Bunn and Forget, supra, and Table 1 herein.

The tertiary structure of the hemoglobin molecule refers to the steric relationships of amino acid residues that are far apart in the linear sequence, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the very atoms of the molecule.

In its unoxygenated ("deoxy", or "T" for "tense") form, the subunits of hemoglobin A (alpha1, alpha2, beta1, and beta2) form a tetrahedron having a twofold axis of symmetry. The axis runs down a water-filled "central cavity". The subunits interact with one another by means of Van der Waals forces, hydrogen bonds and by ionic interactions (or "salt bridges"). The alpha1beta1 and alpha2beta2 interfaces remain relatively fixed during oxygenation. In contrast, there is considerable flux at the alpha1beta2 (and alpha2beta1) interface. In its oxygenated ("oxy", or "R" for "relaxed" form), the intersubunit distances are increased.

The tertiary and quaternary structures of native oxyhemoglobin and deoxyhemoglobin are sufficiently well known that almost all of the nonhydrogen atoms can be positioned with an accuracy of 0.5 Å or better. For human deoxyhemoglobin, see Fermi, et al., J. Mol. Biol., 175: 159 (1984), and for human oxyhemoglobin, see Shaanan, J. Mol. Biol., 171: 31 (1983), both incorporated by reference.

Normal hemoglobin has cysteines at beta 93 (F9), beta 112 (G14), and alpha 104 (G11). The latter two positions are deeply buried in both the oxy and deoxy states; they lie near the $\alpha_1\beta_1$ interface. Beta 93, however, in the oxy form is reactive with sulfhydryl reagents.

Native human hemoglobin has been fully reconstituted from separated heme-free alpha and beta globin and from hemin. Preferably, heme is first added to the alpha-globin subunit. The heme-bound alpha globin is then complexed to the heme-free beta subunit. Finally, heme is added to the half-filled globin dimer, and tetrameric hemoglobin is obtained. Yip, et al., PNAS (USA), 74: 64–68 (1977).

The human alpha and beta globin genes reside on chromosomes 16 and 11, respectively. Bunn and Forget, infra at 172. Both genes have been cloned and sequenced, Liebhaber, et al., PNAS 77: 7054–58 (1980) (alpha-globin genomic DNA); Marotta, et al., J. Biol. Chem., 252: 5040–51 (1977) (beta globin cDNA); Lawn, et al., Cell, 21:647 (1980) (beta globin genomic DNA).

Hemoglobin exhibits cooperative binding of oxygen by the four subunits of the hemoglobin molecule (two alpha-globins and two beta-globins in the case of Hgb A), and this cooperativity greatly facilitates efficient oxygen transport. Cooperativity, achieved by the so-called heme-heme interaction, allows hemoglobin to vary its affinity for oxygen. Hemoglobin reversibly binds up to four moles of oxygen per mole of Hgb.

Oxygen-carrying compounds are frequently compared by means of a device known as an oxygen dissociation curve. This curve is obtained when, for a given oxygen carrier, oxygen saturation or content is graphed against the partial pressure of oxygen. For Hgb, the percentage of saturation increases with partial pressure according to a sigmoid relationship. The $P_{50}$ is the partial pressure at which the oxygen-carrying solution is half saturated with oxygen. It is thus a measure of oxygen-binding affinity; the higher the $P_{50}$, the more loosely the oxygen is held.

When the oxygen dissociation curve of an oxygen-carrying solution is such that the $P_{50}$ is less than that for whole blood, it is said to be "left-shifted."

The oxygen affinity of hemoglobin is lowered by the presence of 2,3-diphosphoglycerate (2,3-DPG), chloride ions and hydrogen ions. Respiring tissue releases carbon dioxide into the blood and lowers its pH (i.e. increases the hydrogen ion concentration), thereby causing oxygen to dissociate from hemoglobin and allowing it to diffuse into individual cells.

The ability of hemoglobin to alter its oxygen affinity, increasing the efficiency of oxygen transport around the body, is dependent on the presence of the metabolite 2,3-DPG. Inside the erythrocyte 2,3-DPG is present at a concentration nearly as great as that of hemoglobin itself. In the absence of 2,3-DPG "conventional" hemoglobin binds oxygen very tightly and would release little oxygen to respiring tissue.

Aging erythrocytes release small amounts of free hemoglobin into the blood plasma where it is rapidly bound by the scavenging protein haptoglobin. The hemoglobin-haptoglobin complex is removed from the blood and degraded by the spleen and liver.

Isolated alpha globin chains are monomers; exhibit high oxygen affinity but of course lack subunit cooperativity. Isolated beta globin chains aggregate to form a $\beta_4$ tetramer (HbH). The $\beta_4$ tetramer has a high but noncooperative oxygen affinity.

B. Blood Substitutes, Generally

It is not always practical to transfuse a patient with donated blood. In these situations, use of a red blood cell substitute is desirable. The product must effectively transport $O_2$, just as do red blood cells. ("Plasma expanders", such as dextran and albumin, do not transport oxygen.) The two types of substitutes that have been studied most extensively are hemoglobin solutions and fluorocarbon emulsions.

It is clear from the above considerations that free native hemoglobin A, injected directly into the bloodstream, would not support efficient oxygen transport about the body. The essential allosteric regulator 2,3-DPG is not present in sufficient concentration in the plasma to allow hemoglobin to release much oxygen at venous oxygen tension.

Nonetheless, solutions of conventional hemoglobin have been used as RBC substitutes. The classic method of preparing hemoglobin solutions employs outdated blood. The red cells are lysed and cellular debris is removed, leaving what is hopefully "stromal-free hemoglobin" (SFH).

Several basic problems have been observed with this approach. The solution must be freed of any toxic components of the red cell membrane without resorting to cumbersome and tedious procedures which would discourage large-scale production. DeVenuto, "Appraisal of Hemoglobin Solution as a Blood Substitute", *Surgery, Gynecology and Obstetrics*, 149: 417–436 (1979).

Second, as expected, such solutions are "left-shifted" (lower $P_{50}$) as compared to whole blood. Gould, et al., "The Development of Polymerized Pyridoxylated Hemoglobin Solution as a Red Cell Substitute", *Ann. Emerg. Med.* 15: 1416–1419 (Dec. 3, 1986). As a result, the oxygen affinity is too high to unload enough oxygen into the tissues. Benesch and Benesch, Biochem. Biophys. Res. Comm., 26:162–167 (1967).

Third, SFH has only a limited half-life in the circulatory system. This is because oxy Hgb partially dissociates into a dimer ($\alpha\beta$) that is rapidly cleared from the blood by glomerular filtration and binding to circulating haptoglobulin. If large amounts of soluble hemoglobin are introduced into the circulation, glomerular filtration of the dimers may lead to a protein and iron load on the kidney capable of causing renal damage. Bunn, H. F., et al. (1969) The renal handling of hemoglobin I. Glomerular filtration. J. Exp. Med. 129:909–923; Bunn, H. F., and J. H. Jandl; (1969) The renal handling of hemoglobin II. Catabolism. J. Exp. Med. 129:925–934; Lee, R. L., et al. (1989) Ultrapure, stroma-free, polymerized bovine hemoglobin solution: Evaluation of renal toxicity (blood substitutes) J. Surgical Res. 47:407–411; Feola, M., et al. (1990) Nephrotoxicity of hemoglobin solutions. Biomat. Art. Cell Art. Org., 18(2):233–249; Tam, S. C. and J. T. F. Wong (1988) Impairment of renal function by stroma-free hemoglobin in rats. J. Lab. Clin. Med. 111:189–193.

Finally, SFH has a high colloid osmotic pressure (COD). Thus, administration of SFH in a dose that would have the same oxygen-carrying capacity as a unit of packed red blood cells is inadvisable, since the high osmotic pressure (60 mm Hg) would cause a massive influx of water from the cells into the bloodstream, thus dehydrating the patient's tissues. This consideration limits the dose of SFH to that which provide a final concentration of about 6–8 gm Hgb/dl.

In an effort to restore the desired $P_{50}$, researchers added 2,3-DPG to the hemoglobin solution. Unfortunately, 2,3-DPG was rapidly eliminated from the circulation. Scientists then turned to other organic phosphates, particularly pyridoxal phosphate. Like 2,3-DPG, these compounds stabilized the "T state" of the Hgb by forming a salt bridge between the N-termini of the two beta chains. The pyridoxylated hemoglobin had a $P_{50}$ of 20–22 torr, as compared to 10 torr for SFH and 28 torr for whole blood. While this is an improvement over SFH, the pyridoxylated Hgb remains "high affinity" relative to whole blood.

C. Naturally Occurring Cysteine Substitution Mutants of Hemoglobin (Non-Polymerizing)

There are a few known naturally occurring mutants of human hemoglobin in which a cysteine residue is substituted for another residue of normal hemoglobin Ao.

In hemoglobin Nigeria, the mutation is α 81 Ser→Cys; no disulfide is formed. Horis, et al., *Blood*, 55(1):131–137 (1980). In Hemoglobin Rainier, an intrasubunit disulfide is formed between the wild type F9(93)β Cysteine and the cysteine introduced by replacement of the Tyr at HC2(145)β. Greer, et al., *Nature [New Biology]*, 230:261–264 (1971). Hemoglobin Nunobiki (β 141 Drg→Cys) also features a non-polymerizing cysteine substitution. In both Hb Rainier and Hb Nunobiki, the new cysteine residues are on the surface of the tetramer.

D. Naturally Occurring Polymerizing or Polymeric Hemoglobins

Three other human mutants are known which polymerize as a result of formation of intermolecular (first tetramer to second tetramer) disulfide bridges. In Hemoglobin Porto Alegre, the Ser at A6(9)β is replaced by Cysteine, and since this cysteinyl residue is externally oriented, spontaneous polymerization occurs, and results in formation of a dodecamer with three Porto Alegre tetramers linked by disulfide bonds. An octamer has also been made by a 1:1 mixture of Porto Alegre hemoglobin and normal hemoglobin. Tondo, Biochem. Biophys. Acta, 342:15–20 (1974); Tondo, An. Acad. Bras. Ci, 59:243–251 (1987).

Hb Mississippi is characterized by a cysteine substitution in place of Ser CD3(44)β. Hemolysates of a patient were subjected to gel filtration column chromatography, and 48.8% eluted in the void volume. Since the molecular weight exclusion was about 600 kD, this suggested that Hb MS polymers are composed of ten or more hemoglobin tetramers. Adams, et al., Hemoglobin, 11(5):435–452 (1987).

A β83(EF7)Gly→Cys mutation characterizes Hemoglobin Ta Li. This mutant showed slow mobility in starch gel electrophoresis, indicating that it was a polymer.

Polymeric mouse hemoglobins have been reported. In BALB/cJ mice, there is a reactive cysteinyl residue near the NH$_2$-terminal of the beta chain (β-13 in the mouse). This mouse mutant has been compared to Hemoglobin Porto Alegre, which likewise has a cysteinyl residue in the A-helix of the beta chain. Octamer formation is most common. However, each tetramer has two extra cysteinyl residues, one on each β-chain, that may react with different tetramers; "this explains why aggregates larger than octamers occur". Bonaventura and Riggs, Science, 158:800–802 (1967); Riggs, Science, 147:621–623 (1965).

Macaques also exhibit a polymerizing hemoglobin variant. Takenaka, et al., Biochem. Biophys. Acta, 492:433–444 (1977); Ishimoto, et al., J. Anthrop. Soc. Nippon, 83(3):233–243 (1975). This mutant has been compared to the Ta Li variant in humans.

Both amphibians and reptiles possess polymerizing hemoglobins. For example, in the bullfrog, hemoglobin "Component C" polymerizes by disulfide bond formation between tetramers. This is said to be primarily dependent on cysteinyl residues of the alpha chain. Tam, et al., J. Biol. Chem., 261:8290–94 (1986).

The extracellular hemoglobin of the earthworm (*Lumbricus terrestris*) has a complex structure. There are twelve subunits, each being a dimer of structure (abcd): where "a", "b", "c", and "d" denote the major heme containing chains. The "a", "b", and "c" chains form a disulfide-linked trimer. The whole molecule is composed of 192 heme-containing chains and 12 non-heme chains, and has a molecular weight of 3800 kDa. Other invertebrate hemoglobins are also large multi-subunit proteins.

The brine shrimp Artemia produces three polymeric hemoglobins with nine genetically fused globin subunits. Manning, et al., Nature, 348:653 (1990). These are formed by variable association of two different subunit types, a and bβ. Of the eight intersubunit linkers, six are 12 residues long, one is 11 residues and one is 14 residues.

E. Artificially Crosslinked Hemoglobins (Non-Polymerizing)

The properties of hemoglobin have been altered by specifically chemically crosslinking the alpha chains between the Lys99 of alpha1 and the Lys99 of alpha2. Walder, U.S. Pat. No. 4,600,531 and 4,598,064; Snyder, et al., PNAS (USA) 84: 7280–84 (1987); Chaterjee, et al., J. Biol. Chem., 261:9929–37 (1986). The beta chains have also been chemically crosslinked. Kavanaugh, et al., Biochemistry, 27: 1804–8 (1988). Kavanaugh notes that the beta N-termini are 16 Å apart in the T state and 20 Å apart in the R state. Not surprisingly, the introduction of a DIDS bridge between the N-termini of T state hemoglobin hindered the shift to the R state, thereby decreasing the O$_2$ affinity of the molecule. While the Kavanaugh analogue has desirable oxygen binding and renal clearance characteristics, it too is obtained in low yield.

Hoffman and Nagai, U.S. Pat. No. 5,028,588 suggest that the T state of hemoglobin may be stabilized by intersubunit (but intratetrameric) disulfide crosslinks resulting from substitution of cysteine residues for other residues. A particularly preferred crosslink was one connecting beta Gly Cys with either alpha G17 (Ala→Cys) or G18 (Ala→Cys).

F. Artificially Crosslinked Hemoglobin (Polymerizing)

Bonsen, U.S. Pat. No. 4,001,401, U.S. Pat. No. 4,001,200, and U.S. Pat. No. 4,053,590 all relate to polymerization of red blood cell-derived hemoglobin by chemical crosslinking. The crosslinking is achieved with the aid of bifunctional or polyfunctional crosslinking agents, especially those reactive with exposed amino groups of the globin chains. The result of the crosslinking reaction is a polydisperse composition of covalently cross-linked aggregates.

Bonhard, U.S. Pat No. 4,336,248 discloses chemical crosslinking of hemoglobin molecules to each other, or to serum proteins such as albumin.

Bonhard, U.S. Pat. No. 4,777,244 sought to stabilize the dialdehyde-cross-linked hemoglobins of the prior art, which tended to polymerized further while in storage, by adding a reducing agent to stabilize the azomethine bond.

Bucci, U.S. Pat. No. 4,584,130, at col. 2, comments that "the polyhemoglobin reaction products are a heterogeneous mixture of various molecular species which differ in size and shape. The molecular weights thereof range from 64,500 to 600,000 Daltons. The separation of individual molecular species from the heterogeneous mixture is virtually impossible. In addition, although longer retention times in vivo are obtained using polyhemoglobins, the oxygen affinity thereof is higher than that of stroma-free hemoglobin."

According to Tye, U.S. Pat. No. 4,529,719, "most workers have chosen to form the random intermolecular crosslinked polymers of hemoglobin because they believed that the 65,000 Dalton tetramer was filtered by the glomerulus . . . . Usually the amino groups of lysine on the surface of the hemoglobin molecule are coupled with a bifunctional reactant such as gluteraldehyde or suberimidate. There are 42 lysines available for reaction per hemoglobin tetramer so that one can get an infinite number of different inter [or] intra molecular crosslinks making various polymers of hemoglobin . . . . The random polymerization is difficult to control and gives a range between two and ten tetramers per polymer . . . . No one has yet standardized an analytical scheme to establish lot to lot variability of structure and function . . . . [Polymerized pyridoxylated hemoglobin has] a profound chemical heterogeneity making it difficult to study as a pharmaceutical agent."

G. Fused Genes and Proteins, Generally

Genes may be fused together by removing the stop codon of the first gene, and joining it in phase to the second gene. Parts of genes may also be fused, and spacer DNAs which maintain phase may be interposed between the fused sequences. The product of a fused gene is a single polypeptide, not a plurality of polypeptides as is expressed by a polycistronic operon. Different genes have been fused together for a variety of purposes. Thus, Gilbert, U.S. Pat. No. 4,338,397 inserted a rat preproinsulin gene behind a fragment of the *E. coli* penicillinase gene. His purpose was to direct *E. coli* transformants to secrete the expression product of the fused gene. Fused genes have also been prepared so that a non-antigenic polypeptide may be expressed already conjugated to an immunogenic carrier protein.

The use of linker DNA sequences to join two different DNA sequences is known. These linkers are used to provide restriction sites for DNA cleavage, or to encode peptides having a unique character that facilitates purification of the encoded fusion protein or a fragment thereof. See, e.g., Rutter, U.S. Pat. No. 4,769,326.

Hallewell, et al., J. Biol. Chem., 264: 5260–68 (1989) prepared an analogue of CuZn superoxide dismutase. Each dismutase molecule is a dimer of two identical subunits; a copper ion and a zinc ion are liganded to the subunit. The dimer interaction in CuZn superoxide dismutase is so strong that the subunits have not been separated without inactivating the enzyme. The enzyme has considerable conformational similarity to immunoglobulins; Hallewell, et al., joined two human superoxide dismutase genes, either directly or with DNA encoding a 19-residue human immunologlobulin IgA1 hinge region and expressed the fused genes in a transformed host. In attempting to express the directly joined genes, recombination occurred to eliminate one of the tandem genes in some plasmid molecules. Hallewell, et al., postulated that the direct connection distorted the dimer, causing the exposure of hydrophobic areas which then had a toxic effect. This would have provided selection pressure favoring gene deletion. No recombination was detected with the IgA1 linker construction.

Hoffman, et al., WO88/09179 describe the production, in bacteria and yeast, of hemoglobin and analogues thereof. The disclosed analogues including hemoglobin proteins in which one of the component polypeptide chains consists of two alpha or two beta globin amino acid sequences covalently connected by peptide bonds, preferably through an intermediate linker of one or more amino acids, without branching. In normal hemoglobin, the alpha and beta globin subunits are non-covalently bound.

SUMMARY OF THE INVENTION

The present invention relates to multimeric hemoglobin-like proteins wherein two or more tetramers or pseudotetramers are covalently bonded. Between any pair of covalently linked tetramers, the covalent linkage may take the form of a crosslink between two cysteine residues of different polypeptide chains, or of a peptide linker connecting the "carboxy most" residue of a globin-like domain of one tetramer with the "amino most" residue of a similar domain of a second tetramer.

Preferably, the multimeric hemoglobin-like protein-containing composition is at least 50% monodisperse, more preferably, at least 95% monodisperse.

Although free hemoglobin purified from natural sources may be polymerized by chemical crosslinking to increase halflife via increased molecular weight, and to reduce oncotic pressure, all such preparations are heterogeneous. Monodispersability can be achieved only by laborious purification.

The present invention provides means of exerting strict control over the degree of polymerization of hemoglobin tetramers. The ability to strictly control formation of multimers will greatly facilitate purification and characterization of the final product and will reduce the chance of adverse reaction to minor components. It is also believed that a more monodisperse composition will have greater consistency of clinical effect.

Hemoglobin also may be made by expression of alpha and beta globin genes in the same or different host cells, and subsequent assembly of the expressed alpha and beta globins, with heme, to form hemoglobin. While the introduction of suitable Cys codon mutations into the globin genes facilitates the production of a crosslinked multimeric hemoglobin, the expression product in general, will not be essentially monodisperse. Hemoglobin is composed of two alpha and two beta globin subunits. Both alpha globin subunits are natively expressed from a single alpha globin gene, and both beta globin subunits, from a single beta globin gene. Thus, if an alpha globin gene is expressed which contains a single Cys codon substitution, the assembled tetramer will contain two alpha globin subunits, each with a crosslinkable Cys. One Cys could crosslink to a second tetramer, and the other to a third, thus resulting in formation of a higher order oligomer.

In one embodiment, the multimeric protein is an octamer consisting essentially of two tetramers which are covalently crosslinked. To avoid unwanted polymerization, each tetramer has only a single participating cysteinyl residue, whose thiol groups are reacted either with each other (under oxidizing conditions, forming a disulfide bond) or with a thiol-reactive crosslinking agent, to form the crosslink.

A fused gene which encodes a single polypeptide comprising two globin-like domains may be mutated so as to provide an externally crosslinkable Cys in only one of the two otherwise substantially identical domains of the resulting pseudodimeric polypeptides. This pseudodimer may then be assembled with the complementary subunits to form a tetramer with only the single cysteine. Two such tetramers, finally, may be crosslinked to obtain the octamer, preferably in essentially monodisperse form.

If the formation of a higher order multimer, such as a dodecamer, is desired, the component pseudotetramers, each having a single externally crosslinkable cysteine, are each covalently attached to a reactive site of a polyfunctional crosslinker having a suitable half-life in the bloodstream.

Another way of obtaining a multimeric hemoglobin instead of crosslinking two or more pseudotetramers, to combine their pseudodimeric subunits into a single pseudooligomer that is shared by all of the component pseudotetramers of the multimeric hemoglobin. For example a pseudooctameric polypeptide, comprising eight alpha globin-like domains, joined covalently by peptide bonds (typically with a peptide spacer), may be assembled with eight individual beta globin-like subunits to form a tetratetrameric human hemoglobin-like protein. Higher order multimers may be prepared simply by expressing a suitable pseudooligomer and assembling it with the complementary monomeric subunits.

The preparation of multimeric hemoglobins with a genetically fused pseudooligomeric backbone avoids the disadvantages of chemical crosslinking. The latter is inefficient and often requires deoxygenation of the hemoglobin solution and the presence of another molecule (e.g., inositol hexaphosphate or 2,3-DPG) to prevent competing reactions.

In the embodiments discussed above, an essentially monodisperse multimeric hemoglobin is achieved by limiting the number of externally crosslinkable cysteines to one per tetramer. However, it is possible to have more than one externally crosslinkable cysteine per tetramer, provided that they are so positioned that after one is crosslinked to a foreign tetramer, other foreign tetramers are sterically prevented from crosslinking to the remaining cysteines of the original tetramer.

The multimeric proteins of the present invention, particularly at higher levels of polymerization, may prolong the half-life of recombinant hemoglobin by reducing extravasation and glomerular filtration of dissociated subunits in vivo compared to native human hemoglobin. Studies of halflife as a function of macromolecular size indicate a correlation between increased size and increased circulatory halflife for chemically crosslinked Hb as well as other macromolecules. Preferably, in humans, the half-life exceeds 9 hours at a dose of at least 1 gm/kgm body weight. This would be expected to correspond to a half-life of about 3 hours in rats given a comparable dose.

Intravascular retention may also be enhanced by engineering the tetramer crosslinking sites so that the haptoglobin binding sites of the tetramers are wholly or partially occluded. Independent mutations may also be made to sterically hinder haptoglobin binding, or to electrostatically repel or sterically hinder the approach of agents which otherwise might degrade the crosslink.

The multimeric proteins of the present invention may also increase oncotic pressure because the number of oxygen binding heme groups per polytetramer of order "n" is "n" times the number per tetramer. Independent of size, the oncotic pressure for a given concentration of heme groups in a solution of polytetrameric Hb is expected to be (1/n) times that of an equimolar solution of heme contained in tetrameric Hb. Because of oncotic pressure effects, the maximum concentration of free tetrameric Hb that may be introduced into the blood stream is less on a per volume basis than the concentration of Hb normally carried in intact red blood cells. Reduction of oncotic pressure is therefore useful in increasing the per volume oxygen carrying capacity of a blood substitute.

In a preferred embodiment, one or more globin-like domains contain mutations which reduce the oxygen-binding affinity of the hemoglobin analogue in solution so as to approach the oxygen-binding characteristics of whole blood.

BRIEF DESCRIPTION OF THE DRAWINGS

FIG. 2 Shows the sequence [SEQ ID NO:1] of a preferred synthetic gene for expression of (des-Val)-alpha-(Gly)-alpha and des-Val beta globin. This gene is carried by pSGE1.1E4. A shows the region (EcoRI to PstI) containing Shine-Delgarno ribosomal binding sites (SD#1 and SD#2), the sequence expressing the octapeptide (Met . . . Glu) (SEQ ID NO:25) which serves as a cotranslational coupler, and the sequence encoding the two nearly identical alpha globin-like polypeptides and the interposed Gly-Gly linker. The first alpha globin sequence begins "Met-Leu", that is, it contains an artifactual methionine, omits the valine which is the normal first residue of mature alpha globin, and continues with the second residue, leucine. The residues are numbered 1 to 141 (SEQ ID NO:26). The second alpha globin sequence begins "Val-Leu", immediately after the underlined "Gly-Gly" linker. The residues are numbered 1' to 141' (SEQ ID NO:27). Start and stop codons are underlined. B shows the analogous region (PstI to HindIII) containing the coding sequence for des-Val beta globin. The beta residues are numbered 1 to 146 (SEQ ID NO:28). A and B are connected at the PstI site to form a single polycistronic operon.

When a three letter amino acid code is singly underlined, this indicates that the residue is a potential site for an Xaa→Cys mutation to provide a crosslinkable site. The mutations should be made asymmetrically, i.e., only one region of a di-alpha or di-beta gene, so only one crosslink is added per tetramer. While, in FIG. 2, the sites are marked only on the first copy of the alpha gene, they could instead be in the second copy. For convenience, the appropriate beta globin mutation sites are also marked. However, these mutations should be made in only one beta-globin of a di-beta globin gene.

Doubly underlined amino acid codes identify sites where formation of two disulfide bonds (or per subunit) would be sterically hindered, so use of a di-alpha or di-beta construction is unnecessary.

Residues which are candidate sites for mutations to block haptoglobin binding are boxed.

Figure 3:
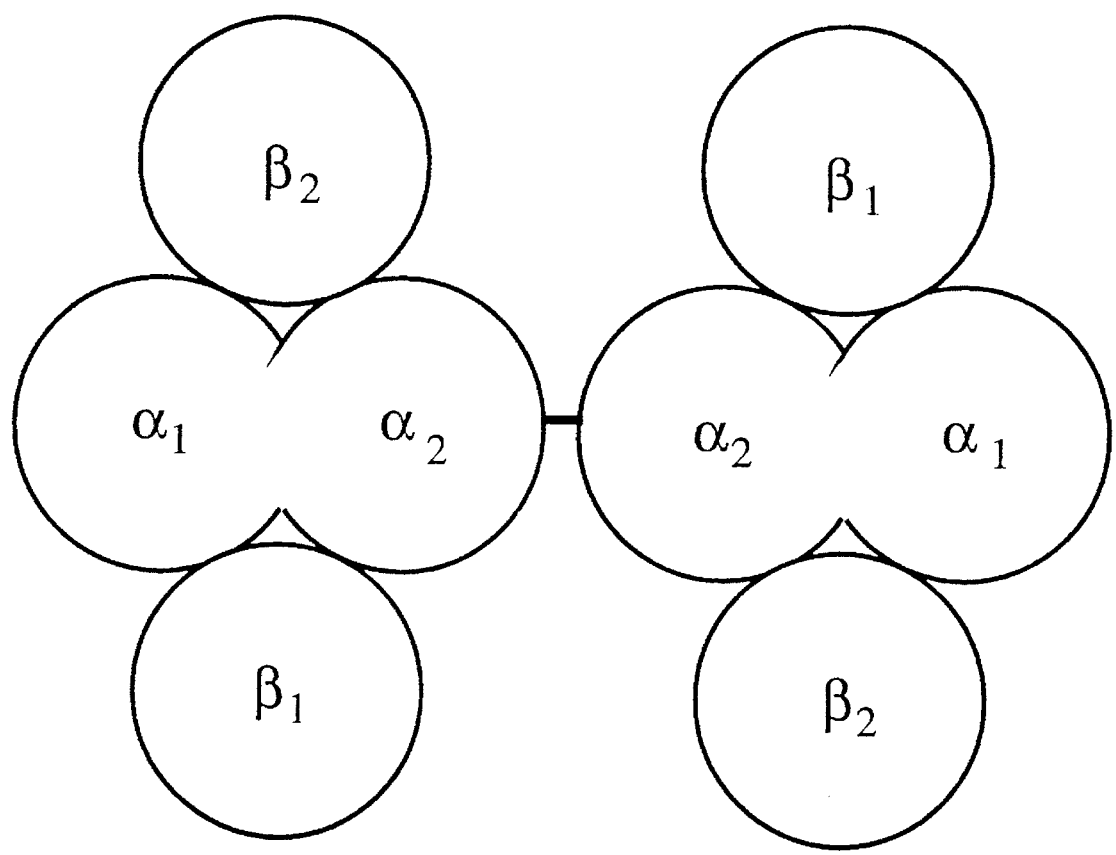

FIG. 3 is a stylized representation of one form of pseudooctameric Hgb, in which the octameric hemoglobin is formed by linking or crosslinking two molecules of an asymmetric di-alpha Hgb.

Figure 4A:
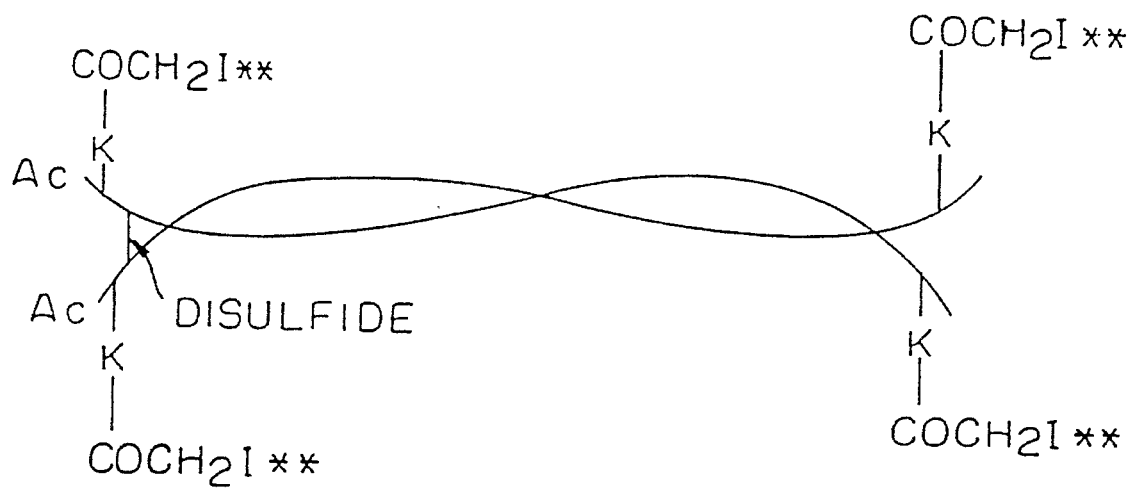
Figure 4B:
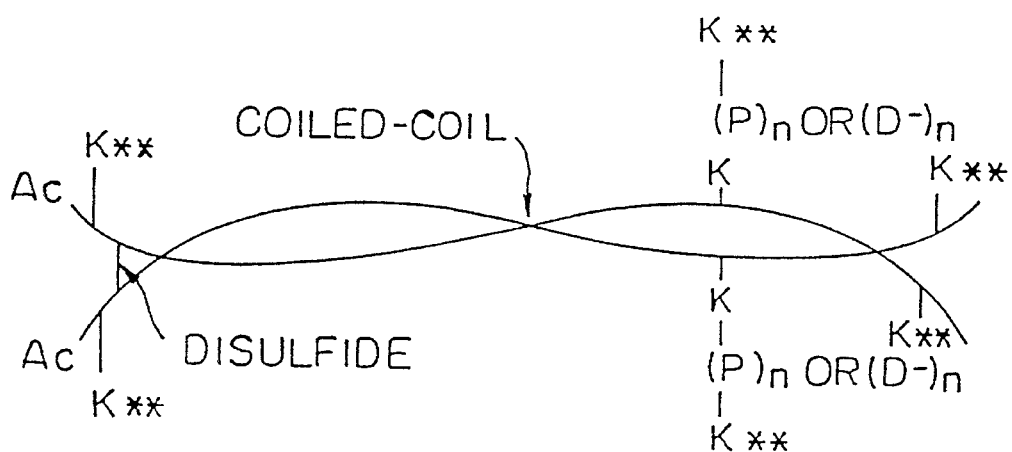
Figure 4C:
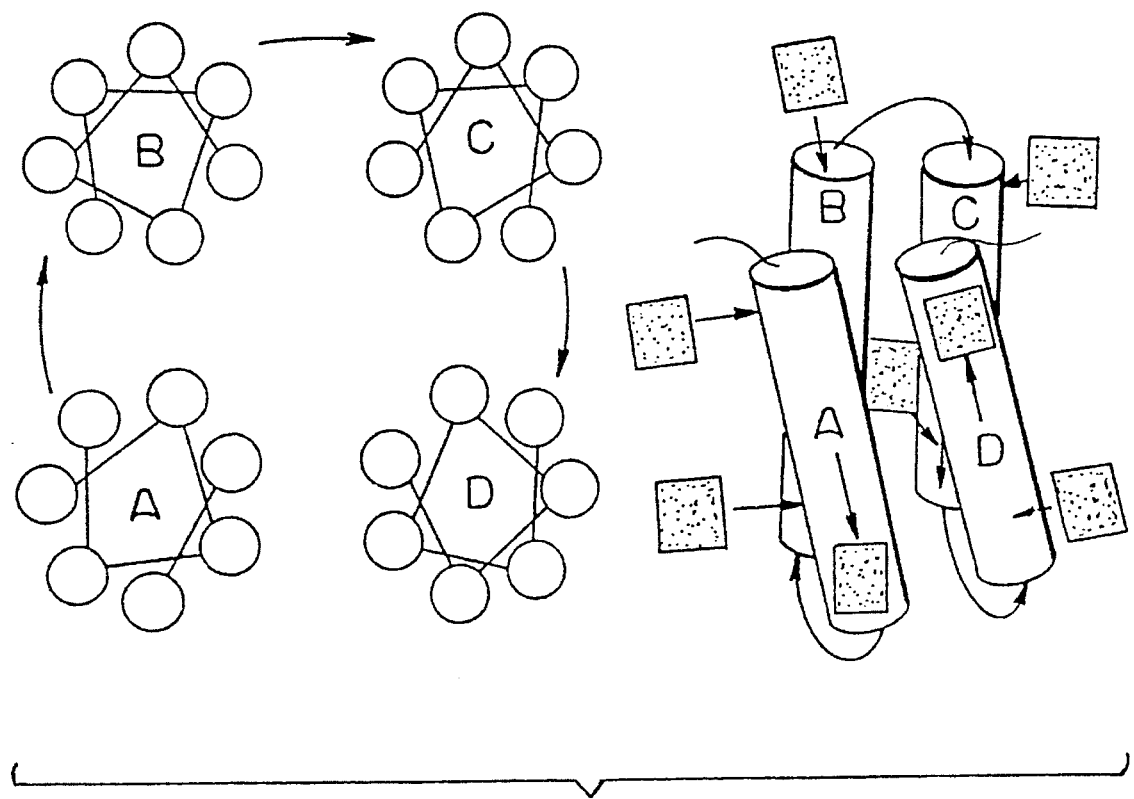

FIGS. 4A–4C depict coiled coil crosslinkers suitable for joining (a) four or (b) six Hgb tetramers. FIG. 4(c) is a top view of a 4-helical bundle, with attachment sites marked.

Figure 5A:
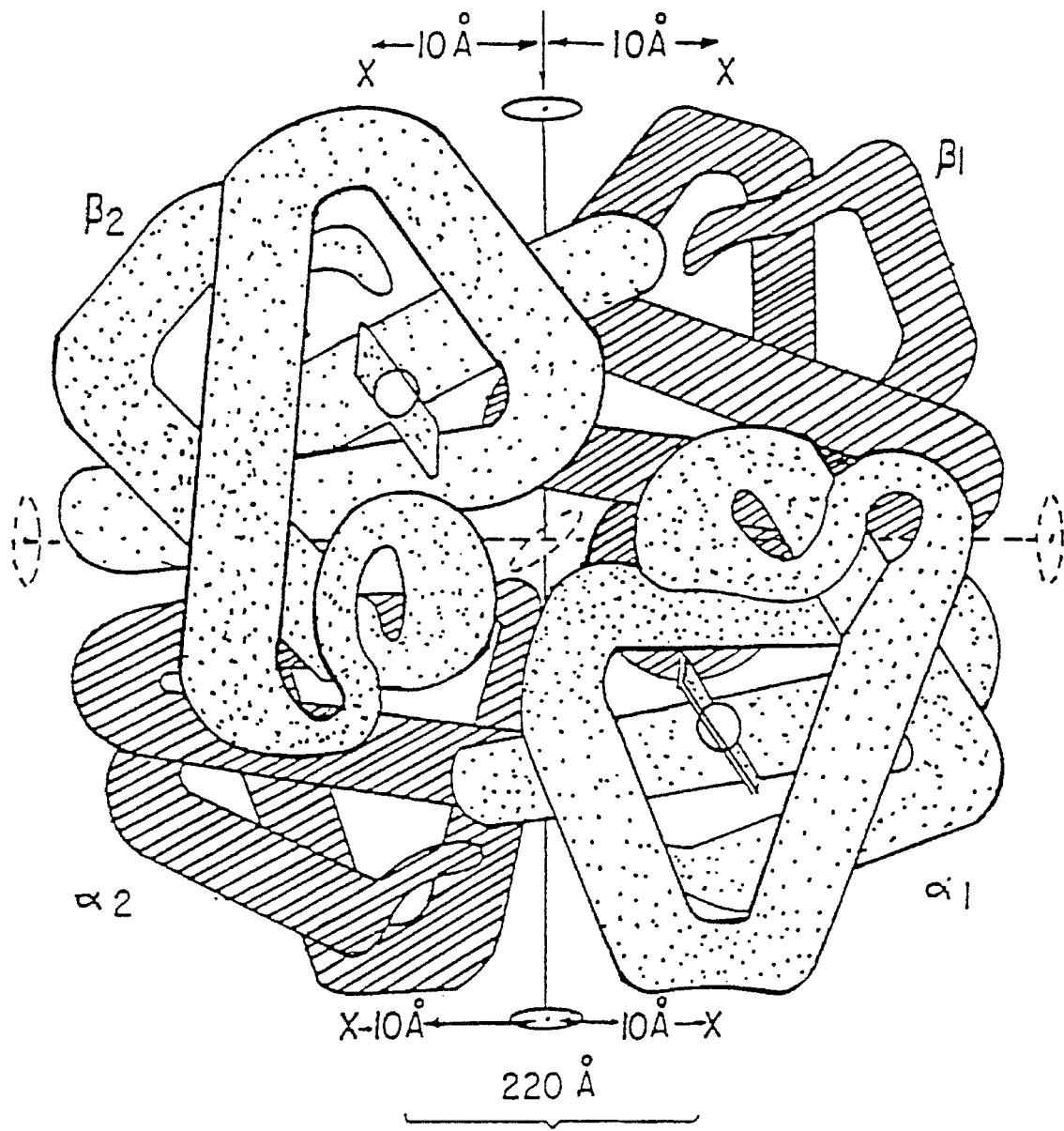
Figure 5B:
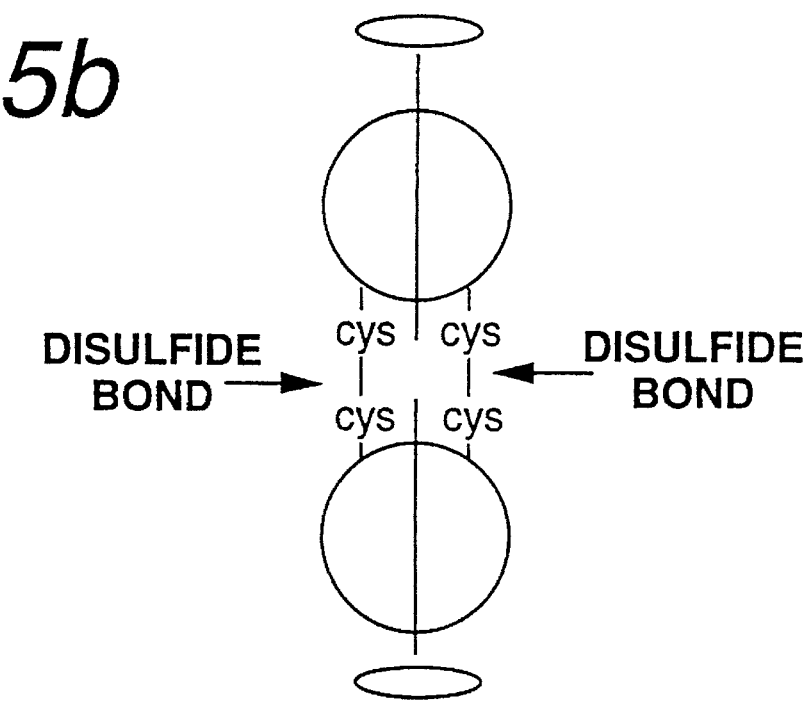
Figure 5C:
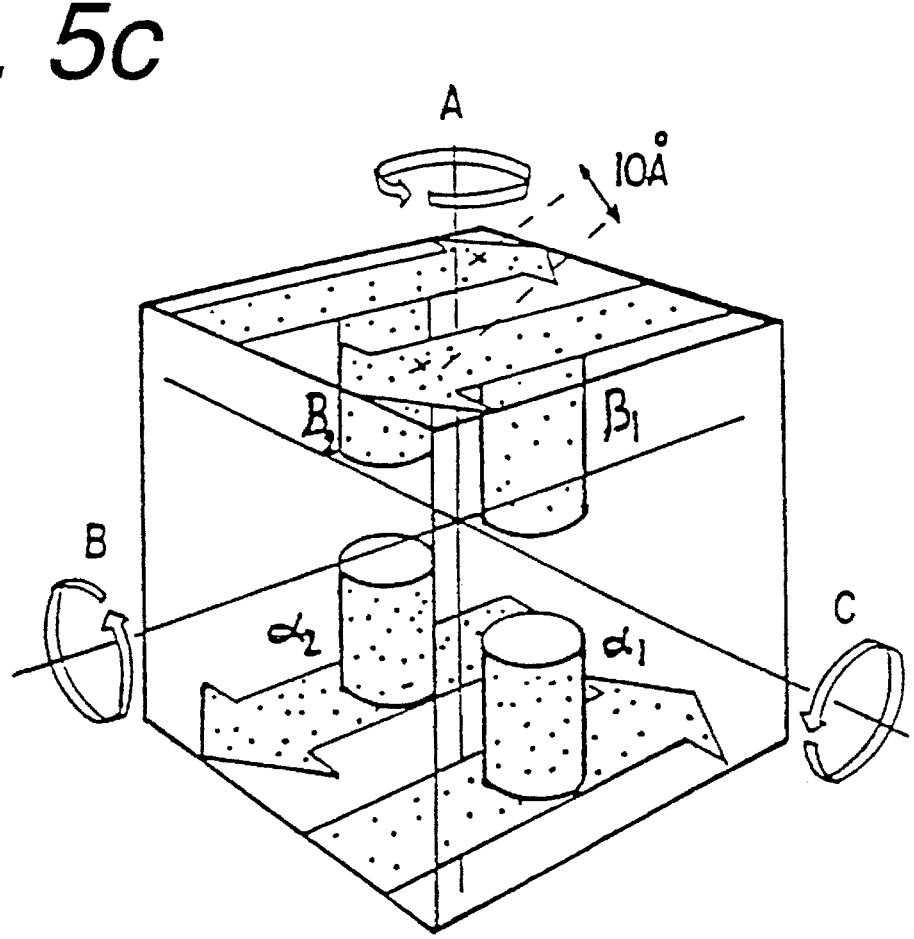

FIG. 5A–5C Schematic showing how cysteine mutations can favor formation of octamer without genetic fusion of subunits.

FIG. 6 Proposed alpha$_1$-beta$_2$ globin pseudodimer.

DETAILED DESCRIPTION OF THE PREFERRED EMBODIMENTS

Definitions

A hemoglobin is a protein which contains heme (ferroprotoporphyrin IX) and that binds oxygen at a respiratory surface (skin, gills, trachea, lung, etc.) and transports the oxygen to inner tissues, where it is released and used for metabolism. In nature, low molecular weight hemoglobins (16–120 kilodaltons) tend to be enclosed in circulating red blood cells while the larger polymeric hemoglobins circulate freely in the blood of hemolymph.

For the purpose of the appended claims, a hemoglobin-like protein is a protein with the following characteristics:

(a) it is sufficiently soluble in blood to be clinically useful as a blood substitute;

(b) it reversibly binds oxygen, under physiological conditions;

(c) each polypeptide chain comprises at least one globin-like domain (as defined below); and (d) each globin-like domain bears (or is capable of incorporating) a heme prosthetic group;

A multimeric hemoglobin-like protein is further characterized as follows:

(e) it is composed of two or more polypeptide chains;

(f) it is composed of two or more tetramers, each tetramer comprising four globin-like domains, and (g) each component tetramer is covalently attached to at least one other component tetramer.

Preferably, the hemoglobin-like proteins of the present invention have a $P_{50}$ of 2 to 45 torr, more preferably 24 to 32 torr, at 37° C., in blood. Preferably, they also exhibit some degree of cooperativity. Also, they desirably have an intravascular retention at least comparable to that of normal human hemoglobin administered as a blood substitute.

Tetrameric hemoglobin-like proteins have four globin-like domains, octameric hemoglobin-like proteins have eight globin-like domains, and so forth. The term "multimeric" covers any hemoglobin-like protein comprising (4×n) globin-like domains, where n>1.

A pseudomeric hemoglobin-like protein is one for which the number of globin-like domains is greater than the number of component polypeptide chains, i.e., at least one chain comprises at least two globin-like domains. The pseudoheterotetrameric hemoglobin-like proteins, for example, may be composed of (a) one di-alpha globin-like and two beta globin-like polypeptides, (b) two alpha globin-like and one di-beta globin-like polypeptides, (c) one di-alpha globin-like and one di-beta globin-like polypeptides, (d) one fused alpha/beta globin-like polypeptide and separate alpha and beta globin-like polypeptides, or (e) two fused alpha/beta globin-like polypeptides. The term "tetramer" includes "pseudotetramers."

A "genetically fused hemoglobin" is a hemoglobin-like protein comprising at least one "genetically fused globin-like polypeptide", (globin pseudooligomer), the litter comprising two or more globin-like domains which may be the same or different and which are connected directly, or through an amino acid or peptide linker. A di-alpha globin-like polypeptide is one which consists essentially of two alpha-globin-like polypeptide sequences (domains) connected by peptide bonds between the normal C-terminus of the first alpha-globin-like polypeptide (domain) and the normal N-terminus of the second alpha-globin-like polypeptide (domain). These two sequences may be directly connected, or connected through a peptide linker of one or more amino acids; the term "peptide bonds" is intended to embrace both possibilities. Alpha globin chains crosslinked at the N- and C-terminals other than by peptide bonds (e.g., by DIDS) are not di-alpha globins. The di-alpha globin-like polypeptide must be capable of folding together with beta globin and incorporating heme to form functional hemoglobin-like protein. The di-beta globin-like polypeptide is analogously defined. A di-alpha or di-beta globin-like polypeptide with a mutation in only one of the component domains is called "asymmetric".

It is also possible to provide an "alpha/beta-globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

Pseudotetramers which bear only a single externally crosslinkable cysteine may be referred, by way of shorthand, as "mono-cys" molecules. However, the use of this term should not be taken as implying that the tetramer may not comprise other cysteines. A "mono-cys" pseudotetramer is merely one which has only a single cysteine which can participate to a significant degree in crosslinking reactions with a cysteine residue of a second pseudotetramer.

A hemoglobin-like protein is said to be heteromeric if at least two of its globin-like domains are different. Since conventional human hemoglobin is composed of two alpha globins and two beta globins, it is a heterotetramer. A multimeric human hemoglobin-like protein is a heteromer wherein each tetramer or pseudotetramer has two human alpha globin-like domains and two human beta globin-like domains.

The Globin-Like Domain

The globin-like domains may be, but need not be, one per polypeptide chain, and they need not correspond exactly in sequence to the alpha and beta globins of normal human hemoglobin. Rather, mutations may be introduced to alter the oxygen affinity (or its cooperativity, or its dependence on pH, salt, temperature, or other environmental parameters) or stability (to heat, acid, alkali, or other denaturing agents) of the hemoglobin, to facilitate genetic fusion or crosslinking, or to increase the ease of expression and assembly of the individual chains. Guidance as to certain types of mutations is provided, e.g., by Hoffman and Nagai, U.S. Pat. No. 5,028,588, and Ser. No. 07/443,950, incorporated by reference herein. The present invention further includes molecules which depart from those taught herein by gratuitous mutations which do not substantially affect biological activity.

A "globin-like domain" is a polypeptide domain which is substantially homologous with a globin subunit of a naturally occurring hemoglobin. A "vertebrate," "mammalian" or "human" globin-like domain is one which is substantially homologous with a globin subunit of, respectively, a naturally occurring vertebrate, mammalian or human hemoglobin.

A human alpha globin-like domain or polypeptide is native human alpha globin or a mutant thereof differing from the native sequence by one or more substitutions, deletions or insertions, while remaining substantially homologous (as hereafter defined) with human alpha globin, and still capable of incorporating heme and associating with beta globin. The term "human alpha globin-like domain" is intended to include but not be limited to naturally occurring human alpha globins, including normal human alpha globin. A beta globin-like domain or polypeptide is analogously defined. Subunits of animal hemoglobins or mutants thereof which are sufficiently homologous with human alpha or beta globin are embraced by the term "human alpha or beta globin-like domain or polypeptide." For example, the subunits of bovine hemoglobin are within the scope of these terms.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. A human alpha-globin-like domain will typically have at least about 75% sequence identity with wild-type human alpha globin, and greater homology with human alpha globin than with human beta globin. However, a polypeptide of lesser sequence identity may still be considered "substantially homologous" with alpha globin if it has a greater sequence identity than would be expected from chance and also has the characteristic higher structure (e.g., the "myoglobin fold") of alpha globin, the ability to incorporate heme, and oxygen-binding activity. (Note that, as elsewhere explained, an alteration in oxygen affinity (P50), intravascular retention, or cooperativity may be desired, and does not render the mutant nonhomologous if it can still contribute to reversible oxygen-binding activity.) By way of comparison, Artemia's heme-binding domains are considered homologous with myoglobin even though the primary sequence similarity is no more than 27%, as alignment of the heme-binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

Over a hundred mutants of human hemoglobin are known, affecting both the alpha and beta chains, and the effect of many of these mutations on oxygen-binding and other characteristics of hemoglobin are known. The human alpha and beta globins themselves differ at 84 positions. In addition, interspecies variations in globin sequence have been extensively studied. Dickerson, *Hemoglobin: Structure, Function, Evolution and Pathology,* ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin-like protein which, in keeping with the definition thereof, will reversibly bind oxygen. The following resources may be used to identify conservative substitutions (and deletions or insertions):

(a) data on functional hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other oxygen-binding proteins, and molecular modelling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer-Verlag: 1979) and FIG. 3–9 of Creighton, *Proteins: Structure and Molecular Properties* (W. H. Freeman: 1983).

While the data from (a)–(d) is most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative:

I small aliphatic, nonpolar or slightly polar residues - Ala, Ser, Thr (Pro, Gly)

II negatively charged residues and their amides - Asn, Asp, Glu, Gln

III positively charged residues - His, Arg, Lys

IV large aliphatic nonpolar residues - Met, Leu, Ile, Val (Cys)

V large aromatic residues - Phe, Tyr, Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schimer would merge I and II above. Note also that Tyr, because of its hydrogen bonding potential, has some kinship with Ser, Thr, etc.

In general, functionality is less likely to be affected by mutations at surface residues, at least those not involved in either the heme crevice or the subunit contacts. In addition, "loops" connecting alpha helices, as well as free amino or carboxy termini, are more tolerant of deletions and insertions.

A "Met FX alpha globin" is an alpha globin-like polypeptide comprising an N-terminal methionine, a oligopeptide which acts as a recognition site for Factor Xa (e.g., Ile-Glu-Gly-Arg)(SEQ ID NO:2), and an alpha globin-like sequence (e.g., Val-His-Leu-Thr-Pro . . . ) (SEQ ID NO:3) which may correspond to wild-type alpha globin or to a mutant thereof as taught herein. The term "Met FX alpha globin" is some-times abbreviated as "FX alpha globin". "FX beta globin" is an analogously defined beta globin-like polypeptide.

"Met-alpha globin" is an alpha globin-like polypeptide with an extra N-terminal methionine. The second amino acid is valine, which is the first amino acid of mature wild-type alpha globin. Met-beta globin is analogously defined. A "Des-FX alpha globin" gene (or "dFX alpha globin") is a Met-alpha globin gene obtained by excising the FX codons from a Met-FX alpha globin gene. Note that, "Met-Hgb" is used to refer to methionyl Hgb formed from methionyl-alpha globin and methionyl-beta globin.

"Des-Val-alpha globin" (or "dVal alpha globin") is an alpha globin-like polypeptide wherein methionine is substituted for the valine which begins the sequence of mature wild-type alpha globin. Des-Val-beta globin is analogously defined. Des-Val-alpha/alpha globin (di-Des-Val-alpha globin) is a "di-alpha globin" in which a "Des-Val-alpha" sequence is linked via an appropriate peptidyl linker to an alpha globin-like sequence which begins with Val.

Low Affinity Mutants

The term "low affinity hemoglobin-like protein" refers to a hemoglobin-like protein having a $P_{50}$ which is at least 10% greater than the $P_{50}$ of cell free normal hemoglobin $A_o$ under the same conditions. Preferably, the protein, if used as a blood substitute, qualifies as a low affinity protein, and more preferably, its $P_{50}$ is closer to the $P_{50}$ of whole blood cells than to that of cell free hemoglobin.

Low affinity mutant hemoglobins, i.e., those with "right shifted" oxygen equilibrium binding curves relative to cell-free normal hemoglobin, have many potential uses. Most notably, mutant hemoglobins that have an oxygen affinity similar to whole red blood cells may be used as an oxygen-carrying transfusion substitute in place of donated red blood cells, eliminating the risk of infection and alleviating problems with supply. Cell-free native human hemoglobin cannot function as a transfusion substitute, among other reasons because oxygen is bound too tightly. In addition, because cell-free hemoglobin solutions do not need to be crossmatched and are expected to have a longer shelf life than whole blood, low affinity hemoglobin solutions may be widely used in situations where whole blood transfusion is not feasible, for example in an ambulance or on a battlefield. Mutant hemoglobins that have an even lower oxygen affinity than red blood cells may in fact delivery oxygen more effectively in many situations. Mutant hemoglobins that have a somewhat higher oxygen affinity than whole blood (but a lower affinity than cell-free native human hemoglobin) will still function as an adequate transfusion substitute and may in fact deliver oxygen more effectively than red blood cells in some situations. This is because oxygen is released directly to plasma form hemoglobin-based solutions, without the need to diffuse through the red cell membrane, and because cell-free hemoglobin may penetrate into regions not accessible to red blood cells. As an example, low affinity mutant hemoglobin is expected to deliver oxygen effectively during coronary artery balloon angioplasty procedures, whereas circulation of red blood cells is obstructed during such procedures. Low affinity mutant hemoglobin may also be useful as a perfusion component in organ preservation prior to transplantation or as a mammalian cell culture additive.

Possible low affinity mutants are discussed in detail, by way of example and not of limitation, in Table 1 (natural low affinity hemoglobin mutants) and Table 2 (candidate non-naturally occurring low affinity hemoglobin mutants) of Hoffman, et al., U.S. Pat. No. 5,028,588. Low affinity mutants of particular interest are the Presbyterian (beta Lys$^{108}$) beta Phe$^{63}$, beta Ile$^{67}$, and Kansas (beta Thr$^{102}$) mutants.

An unexpected and surprising change in oxygen binding characteristics of hemoglobin was observed upon replacement of the N-terminal valine with methionine. Hemoglobin $A_o$ purified from blood has a $P_{50}$ value of 4.03 with N=2.8 when measured at 25° C. DesFX-hgb produced in E. coli, a hemoglobin identical to $A_o$ except for the addition of a methionine at the N-termini of the alpha and beta chains, has essentially the same $P_{50}$ and N values. Thus, the addition of a methionine, without altering the adjacent valine residue, has little or no effect on oxygen binding. On the other hand, a higher $P_{50}$ value, 6.6, was observed for desVal-hgb produced in E. coli, a hemoglobin in which the normal N-terminal valine of each chain was replaced with methionine. Cooperativity, as measured by N, was virtually the same, however, for all three molecules.

A similar comparison was made for two hemoglobins each containing the Presbyterian mutation, one produced in E. coli and one in yeast. The E. coli hemoglobin was constructed with a Des-Val alpha chain, i.e., the N-terminus had the normal valine replaced with methionine. Oxygen binding was characterized by $P_{50}$=19.8, N=2.5 at 25° C. and by $P_{50}$=34.5 and N=2.5 at 37° C. The corresponding yeast coding region begins with an additional methionine codon in front of the normal valine codon. Because this initial methionine is removed post translationally in vivo, the purified hemoglobin has a normal N-terminal valine. For this molecule, $P_{50}$=23 to 25 and N=2.5 when measured at 37° C. Thus, in the above instances, the replacement of an N-terminal valine with an N-terminal methionine increased the $P_{50}$ value. Under physiological conditions, it is expected that the genetically fused Presbyterian hemoglobin produced in E. coli will deliver 20–30% more oxygen than the similar hemoglobin, with its altered N-terminus, produced in yeast.

High Affinity Mutants

The term "high affinity hemoglobin-like protein" refers to a hemoglobin-like protein having a $P_{50}$ which is at least 10% less than the $P_{50}$ of cell free hemoglobin $A_o$ under the same conditions.

High affinity mutant hemoglobin may have utility in certain situations. For example, perfluorocarbon-based blood substitute preparations are under clinical study for enhancement of radiation therapy and certain chemotherapy treatments of solid tumors (Dowling, S., Fischer, J. J., and Rockwell, S. (1991) *Biomat. Art. Cells Immobil. Biotech*, 19, 377; Herman, T. S. and Teicher, B. A. (1991) *Biomat. Art. Cells and Immobil. Biotech*, 19, 395; Holden, S. A., Teicher, B. A. and Herman, T. S. (1991) *Biomat. Art. Cells and Immobil. Biotech*, 19, 399.) The basis of these investigations is the fact that oxygen is a required component of the cell toxicity action of radiation and certain chemotherapy reagents. Solid tumors frequently exhibit extremely low partial oxygen pressure in the interior of the tumor, rendering therapy inefficient. Perfluorocarbon-based oxygen-carrying solutions appear to dramatically enhance certain tumor therapies, and hemoglobin-based blood substitutes are expected to have a similar utility. It is likely that cell-free hemoglobin unlike whole red blood cells, will be able to penetrate the interior region of tumors for delivery of oxygen. Actual percent of oxygen released by a cell-free hemoglobin preparation is not a direct function of $P_{50}$ but rather depends on the shape of the oxygen equilibrium binding curve between the two pressures representing the partial oxygen pressure of the lungs (where oxygen is loaded onto hemoglobin) and the partial pressure of the tissue where oxygen is unloaded. Therefore, it is possible that a high affinity mutant hemoglobin would be preferred as a tumor therapy adjuvant. A high affinity hemoglobin would retain its bound oxygen throughout the normal circulatory system, where partial oxygen pressure remains relatively high, but release its oxygen in the extremely oxygen-depleted tumor interior. Normal or low affinity hemoglobin might have less hemoglobin available for release by the time it reaches the interior of the tumor.

Naturally occurring high affinity hemoglobin mutants are also known, see Bunn and Forget, Table 14-1, and candidate non-naturally occurring high affinity hemoglobin mutants may be proposed in view of the known mutants and hemoglobin structure. Particularly preferred high affinity mutants are set forth in Table 400.

It should be noted that genetic fusion and crosslinking can affect oxygen binding affinity.

Cysteine Mutations and Disulfide Bridge Formation

Cysteine mutations are of value for increasing the stability of the tetramer (See U.S. Pat. No. 5,028,588 and Ser. No. 07/443,950 now abandoned). They also facilitate constructing poly(tetrameric) (n>=2) hemoglobins. This is because the cysteines on adjacent tetramers (including pseudotetramers) can be oxidized to form a disulfide bridge, covalently coupling the tetramers. In addition, the thiol groups of cysteines may be reacted with a variety of crosslinking agents.

A variety of sites are available for introduction of cysteines into a hemoglobin-like protein.

The criteria governing site selection are: (1) the mutation does not affect functionality; (2) the side chain is accessible to water in oxy or deoxy structure; (3) the site should lie on the surface of the folded protein; (4) the sulfhydryl of the side chain should extend away from the surface rather than toward the interior of the molecule; (5) the site should be in a portion of the molecule that is not directly invovled in the R→T transition; (6) the change should be in a portion of the molecule that does not have a tightly fixed position (such regions generally give indistinct X-ray diffraction patterns); (7) the mutations will not destroy the local secondary structure, i.e., avoid pro→cys mutations, which might result in a refolding problem; and (8) if possible, a conservative change should be made such as ser→cys or ala>cys. A mutation does not necessarily have to meet all of the above requirements to be useful. For example, one might envision a site that is involved in the R→T transition (cf. 5 above) but confers a beneficial change in $P_{50}$ (cf. 1 above) because of that involvement. The most important considerations are that the mutation does not abolish $O_2$ binding, before or after crosslink formations, and that the cysteine is accessible for participation in the desired crosslinking reaction.

Candidate sites on the alpha surface include: his72, ash78, asn68, ala71, thr67, lys7, lys11, thr8, ala12, thr118, lys16, ala45, glu116, gly15, his112, thr24, glu23, lys60, lys56, his50, gly51, glu53, ser49, asp47, gln54, his45, lys90, ala82, lys61, ala19, his20, asp85, ser81, asp75, asp74, lys139, asp64, and gly18 (total 40 amino acids).

Candidate sites on the beta surfaces includes: asp79, his2, leu3, thr4, glu6, ser9, thr12, ala13, gly16, lys17, val18, asn19, val20, asp21, glu22, lys65, ser72, ala76, his77, asp79, asn80, gly83, ala86, thr87, glu90, lys95, lys59, glu43, ser44, asp47, ser49, thr50, ala53, asp52, lys61, glu121, lys120, thr123, lys66, asp73, ala62, his116, his117 (total 45 amino acids).

There are a number of naturally occurring mutants which already show mutations at these sites. These are listed below:

| Residues | Region | Mutation |
| --- | --- | --- |
| 19 | AB1 | ALA—>GLU |
|  |  | ALA—>ASP |
| 54 | E3 | GLN—>ARG |
|  |  | GLN—>GLU |
| 71 | E20 | ALA—>GLU |
| 75 | EF4 | ASP—>GLY |
|  |  | ASP—>HIS |
|  |  | ASP—>TYR |
|  |  | ASP—>ASN |
| 81 | F2 | SER—>CYS |
| 47 | CE5 | ASP—>GLY |
|  |  | ASP—>HIS |
|  |  | ASP—>ASN |

If the pseudo-octamer (n=2) is formed by directly linking two pseudo-tetramers via a disulfide bond, the halflife in serum may be influenced by the rate at which endogenous serum small molecule thiols (such as glutathione) reduce the disulfide bond. The mechanism of these reactions involves the thiolate anion as the actual reducing species (Creighton, T. E. (1978) *Prog. Biophys. Molec. Biol.*, 33:259–260; Creighton, T. E. (1975) *J. Mol. Biol.*, 96:767; Creighton, T. E. (1977) *J. Mol. Biol.*, 113:313). Thus the rate of reduction will be a function of the molecular electrostatic environment in the vicinity of the disulfide bond. A slower rate of reduction would be predicted if the disulfide was located in an electrostatically negative environment,, due to the repulsion of the thiolate anion. In the case of glutathione, even the unreactive transient protonated species has a net negative charge and would be repulsed, thus further reducing the rate of disulfide reduction.

A surface or near-surface amino acid residue of di-alpha or di-beta hemoglobin that is located in close proximity to a negatively charged surface residue might therefore be a good choice for location of a single cysteine mutation in the di-alpha or di-beta polypeptide. Although formation of the initial disulfide bond between two such cysteines might also be slower because of repulsion between the negative charges on the two hemoglobin molecules in the vicinity of the cysteines, the reaction could be facilitated by use of high salt or high pH during the in vitro bond formation reaction. If carried out under deoxy conditions in a redox buffer, the reaction might also be facilitated by temperature elevation.

| Preferred sites for cys mutations proximal to negative charged residues | |
| --- | --- |
| alpha ser49 | near asp47; naturally occurring ser49 to arg has normal $O_2$ affinity |
| alpha his20 | near glu23; naturally occurring his20 to tyr, gln, arg have no known undesirable properties |
| alpha lys16 | near glu116; naturally occurring lys to glu has normal $O_2$ affinity |
| alpha his50 | near glu30; naturally occurring his50 to asp has no known undesirable properties |
| beta thr50 | near asp52; naturally occurring thr50 to lys has no known undesirable properties |
| beta lys65 | near asp21 |
| beta asn19 | near asp21 |

Surface or near-surface cysteine mutations in general are not expected to have major effects on the functionality of the hemoglobin pseudotetramer. Cysteine mutations would not be expected to significantly destabilize alpha helices, and surface residues are not directly involved in the oxygen binding properties of hemoglobin. Most surface residues undergo considerable motion and are not tightly constrained. It should also be noted that because of protein breathing motions, the cysteine side chain would not necessarily have to point directly into solution to be accessible for disulfide bond formation.

In addition to the use in construction of a pseudo-octamer, there may be additional uses of surface cysteine mutations. These include: (1) construction of multimeric hemoglobins (n>2) by use of synthetic sulfhydryl reactive peptides with more than two reactive sites; (2) surface cysteine residues could be used to attach chelates that bind radioisotopes for imaging; and (3) surface cysteines could be used to attach bio-active peptides or other therapeutic agents to increase their circulating half-life, or target their delivery. If the attachment of the drug were via a disulfide, the rate of release of the peptide from its carrier could be controlled by neighboring residues. For uses (2) and (3), restriction to one cysteine per di-alpha or di-beta is unnecessary.

It may be desirable to eliminate the cysteine at beta 93 of normal human hemoglobin so that it cannot participate in polymerization reactions. This cysteine may be replaced by serine, alanine or threonine, for example. Other wild-type cysteines may also be replaced, if desired, but it is unlikely that they participate in crosslinking reactions after the tetramer is formed.

Mutations to Reduce Haptoglobin Binding

It is presently believed that haptoglobin binding plays a role in the catabolism of hemoglobin. If so, intravascular retention of hemoglobin might be enhanced by mutations which inhibit haptoglobin binding. Oxyhemoglobin dissociates into alpha-beta dimers, which are then bound by haptoglobin. While much of the binding energy is associated with binding to residues which are buried in the tetramer but exposed in the dimer, it appears that there are also secondary binding sites on the surface of the tetramer. Though the mechanism is not clear, the haptoglobin-bound dimers are transported to Kupffer cells in the liver, where they are catabolized.

It would be most desirable to mutate sites which both are involved in haptoglobin binding and which are suitable for attachment of another tetramer. Candidate mutation sites are in the alpha chain of normal human alpha globin, residues 1, 6, 74, 82, 85, 89, 90, 93, 118, 120–127 and 139–141, and in the beta chain, residues 2, 11–40 and 131–146. It is unlikely that haptoglobin binding can be blocked merely by single substitution mutation of one genetically encoded amino acid to another. However, if the above residues are replaced by a cysteine, and the cysteine is crosslinked to another molecule which is significantly larger than the usual amino acid side chain, the steric effect is magnified considerably and haptoglobin binding may be inhibited. Of course, to retain polymerization control, these mutations should be made asymmetrically in a pseudooligomeric polypeptide so that there is only one crosslink per tetramer.

It is known that even covalently crosslinked hemoglobins can be processed by haptoglobin; this is thought to be the result of the "breathing" of the tetramer in its oxy form sufficiently to allow the haptoglobin access to the normally buried residues of the subunit interfaces in question. This may be prevented by tightly crosslinking the globin subunits so dissociation will not occur within the time span of interest. Unlike the mutations discussed above, these mutations should be made in all of the indicated subunits for maximum efficiency.

beta37→Cys and alpha92→Cys beta40→Cys and alpha92→Cys beta97→Cys and alpha41→Cys The above mutations all lie at the $alpha_1beta_2$ and $beta_1alpha_2$ interfaces and lock these interfaces shut so that "breathing" does not allow haptoglobin access.

"Breathing" may also be inhibited by low oxygen affinity mutations; the tetramer then spends more time in the deoxy state, which is not susceptible to haptoglobin attack.

Pseudomeric Globin-Like Polypeptides and Pseudotetrameric Hemoglobin-Like Proteins Useful as Intermediates in Preparation of Multimeric Hemoglobin-Like Proteins In the liganded form, haemoglobin readily dissociates into αβ dimers which are small enough to pass through the renal glomeruli, and Hb is thereby rapidly removed from the circulatory system. Intravenous administration of haemoglobin in amounts far less than that needed to support oxygen transport can result in long term kidney damage or failure. Ackers, G. K. and Halvorson, H. R., Proc. Nat. Acad. Sci. (USA) 71, 4312–16 (1974); Bunn, H. F., Jandl, J., J. Exp. Med. 129, 925–34 (1969). If dissociation into dimers is prevented, there is an increase in intravascular half life and a substantial reduction off renal toxicity. Lee, R., Atsumi, N., Jackbs, E., Austen, W., Vlahakes, G., J. Surg. Res. 47, 407–11 (1989). The hemoglobin-like proteins of the present invention cannot dissociate into αβ-dimers without the breakage of a peptide bond and should have the advantages of a longer intravascular half life and reduced renal toxicity.

In the crystal structures of both deoxyhaemoglobin and oxyhaemoglobin the N-terminal Val residue for one α subunit and the C-terminal Arg residue of the other α subunit are only between 2 and 6 Å apart, and are bound to one another through a salt bridge in deoxyhaemoglobin. Fermi, G., Perutz, M., Shaanan, B., Fourme, R., J. Mol. Biol., 175, 159–74 (1984); Shaanan, B., J. Mol. Biol. 171, 31–59 (1983). This distance could be spanned by one or two amino acids. One extra amino acid can be added to the C-terminal Arg residue of the α subunits by trypsin catalyzed reverse hydrolysis without significantly altering the oxygen binding properties. Nagai, K., Enoki, Y., Tomita, S. and Teshima, T., J. Biol. Chem., 257, 1622–25 (1982) Preferably the di-alpha linker (if one is used) consists of 1 to 3 amino acids which may be the same or different. A Mono-Gly linker is especially preferred. In designing such a linker, it is important to recognize that it is desirable to use one or more amino acids that will flexibly connect the two subunits, transforming them into domains of a single di-alpha globin polypeptide.

The preparation of "di-beta" mutants is also contemplated. The distance between the N-terminus of one beta subunit and the C-terminus of the other is 18.4 Å in the deoxy configuration and 5.2 Å in the oxy form. Preferably, the di-beta linker consists of 2 to 9, amino acids which may be the same or different. Glycine amino acids are particularly preferred.

The length of the $(\text{-gly-})_n$ genetically fused link between the N-terminus of one beta chain (at $beta_1$, 1 Val) and the C terminus of the second beta chain ($beta_2$, 146 His) in di-beta hemoglobin may range between 1 and approximately 9 glycines. In the oxy and deoxy crystal structures of human hemoglobin $A_o$, the distance between these termini is 5.22 Å and 17.93 Å respectively (from the N-terminal nitrogen to the C terminal carbon of the carboxylate). A single glycine linker, which is a little less than 4 Å in length, may come close to linking the two termini in the oxy structure, however, it is expected that this linker will fall ~14 Å short in the deoxy structure. Significantly more perturbation of the deoxy structure vs the oxy structure might be anticipated with this linker. Some alterations in the oxygen binding properties may be caused by deletion of the positive and negative charges at the two termini and their inclusion in the amide bond. In addition, the linker molecule itself may destabilize the oxy structure less than the deoxy structure, and thus lead to a relative increase in oxygen affinity. Likewise, two glycines inserted as linkers may also differentially stabilize the oxy structure and hence relatively increase the oxygen affinity by the same mechanism described above.

When the number of linking glycines is increased to 5, the linker should just span the cleft between the beta chain termini in the deoxy structure, and, moreover, insert added steric bulk between the termini in the oxy structure, thus leading to a relative stabilization of deoxy (or destabilization of oxy) and perhaps resulting in a concomitant decrease in oxygen affinity. Due to the large space between the beta termini in the deoxy (but not the oxy structure), addition of glycine linkers in the range of 6–9 may further stabilize the oxy structure and, in the same manner, further decrease oxygen affinity.

A third form of globin pseudodimer is one comprising both alpha and beta globin domains. A possible route to fusing alpha1 to beta2 and so stabilizing hemoglobin against $\alpha_1\beta_1/\alpha_2\beta_2$ dimer formation, is to fuse the alpha1 C-terminal residue to the N-terminal residue of beta2 C helix, creating a new C-terminus at the end of the beta2 B helix. The original beta N terminus, Val1, would be fused to the original beta subunit C-terminal residue, His146, by means of an intervening new section of protein, thus creating a continuous polypeptide chain comprising the alpha and beta subunits of different dimers. This chain may be described as follows: $\alpha(1\text{–}14)\text{-}Gly_3\text{-}\beta(35\text{–}146)\text{-}Gly_{1\text{-}3}\text{-}Ala_{13}\text{-}Gly_{1\text{-}3}\beta(1\text{–}34)$; (SEQ ID. NO:29) See FIG. 6.

Inspection of the structure of human deoxyhemoglobin using a molecular graphics computer indicates the following relevant distances. The distance between the Alpha1 Arg141 carboxyl carbon and Beta2 Tyr35 N atoms is approximately 8.6 Angstroms. A fully extended linear triglycine peptide measured approximately 10.1 Angstroms from the N to C terminal residues. This suggests that three glycine residues could be employed to span the distance between the Arg141 and Tyr35 residues with a minimum of unfavorable steric interactions and maximum conformational freedom. The distance requirements could be different in oxyhemoglobin, and if so, the sequence of the fusion peptide could be altered to best accommodate the requirements of both structures.

In human deoxyhemoglobin, the distance between the Beta2 His146 carboxyl carbon and the Beta2 Val1 nitrogen atoms is approximately 25 Angstroms. A right handed 3.6 Alpha helix constructed from a linear sequence of 13 Alanine residues was found to measure 22 Angstroms from N to C terminus. With the addition of one to three glycine residues at each end of this helix (to give $Gly_n(Ala)_{13}Gly_n$ where n=1 to 3) (residues 130–148 of SEQ ID NO:29), it could span the required distance and have sufficient conformational flexibility to avoid serious tertiary packing conflicts. Additionally, the amino acid sequence of the helix could be altered to introduce favorable hydrogen bonds and salt bridges between the new helix and the Beta2 helix against which it would pack in the folded protein. Such interactions could aid stabilization of the engineered protein.

Glycine is the preferred amino acid in the linkers, since it is known to be quite flexible, Cantor and Schimmel, *Biophysical Chemistry*, part 1, pp. 266–9 (1980), and also allows chains into which it is incorporated to assume a more compact structure. However, the residues comprising the linker are not limited to glycines; other residues may be included instead of or in addition to glycine, such as alanine, serine, or threonine. Since these amino acids have a more restricted conformational space in a protein, they will likely result in more rigid linking chains, and hence have a more pronounced effect on the relative stabilization/destabilization of the oxy/deoxy structures.

It should be understood that the minimum and maximum number of amino acids in the linker is a function of the distance to be spanned in both the oxy or deoxy forms, the amino acids chosen, and the propensity of the particular amino acid sequence to form a secondary structure. While a random coil is usually preferred, it is not required, and a linker with a large number of amino acids in a secondary structure may have the same span as a random coil linker with fewer amino acids. A linker may comprise, e.g., 1–3 glycines, followed by a sequence having a secondary structure, followed by 1–3 more glycines. The translation per residue, in angstroms is 1.9 for polyproline I, 3.12 for polyproline II, 3.1 for polyglycine II, 3.4 for an antiparallel β sheet, 3.2 for a parallel β-sheet, 1.5 for a right handed a-helix, 2.0 for a 310 helix, and 1.15 for a π helix. In a fully extended chain, the maximum translation per residue is 3.63 Å if the repeating units are staggered and 3.8 Å if the peptide bond is trans.

The number of amino acids in the linker may be such that a formation of a secondary structure, such as an alpha helix or a beta-sheet, is undesirable, as the span is reduced. Certain amino acids have a greater tendency to participate in such structures. See Chou and Fasman, Biochemistry, 13:222–245 (1974), incorporated by reference. The amino acids are ranked in order of decreasing participation below. The preferred linker amino acids are boldfaced. Glycine is the most suitable amino acid for this purpose. The most preferred di-alpha linkers are Gly or Gly-Gly.

| Alpha Helix Formers | | | Beta Sheet Formers | | |
|---|---|---|---|---|---|
| Glu | (1.53) | | Met | (1.67) | |
| Ala | (1.45) | | Val | (1.65) | |
| Leu | (1.34) | H∝ | Ile | (1.60) | Hβ |
| His | (1.24) | | Cys | (1.30) | |
| Met | (1.20) | | Tyr | (1.29) | |
| Gln | (1.17) | | Phe | (1.28) | |
| Val | (1.14) | | Gln | (1.23) | |
| Trp | (1.14) | | Leu | (1.22) | |
| Phe | (1.12) | h∝ | Thr | (1.20) | |
| Lys | (1.07) | | Try | (1.19) | hβ |
| Ile | (1.00) | | Ala | (0.97) | Iβ |
| Asp | (0.98) | | Arg | (0.90) | |
| Thr | (0.82) | | Gly | (0.81) | |
| Arg | (0.79) | | Asp | (0.80) | iβ |
| Ser | (0.79) | | Lys | (0.74) | |
| Cys | (0.77) | i∝ | Ser | (0.72) | |
| Asn | (0.73) | | His | (0.71) | |
| Tyr | (0.61) | b∝ | Asn | (0.65) | |
| Pro | (0.59) | | Pro | (0.62) | bβ |
| Gly | (0.53) | B∝ | Glu | (0.26) | Bβ |

(The letter symbols are H∝, strong ∝ former; h∝, ∝ former; I∝; weak ∝ former; i∝, ∝ indifferent; b∝, ∝ breaker; and B∝ strong ∝ breaker. The β symbols are analogous. Trp is bβ if near the C-terminal of a β-sheet region.)

The alpha helix of a polypeptide chain comprises an average of 3.6 residues per turn. In globular proteins, the average length is about 17 Å, corresponding to 11 residues or 3 helix turns. In alpha and beta globin, the helices range in length from 7 to 21 amino acids (A.A.). The beta pleated sheet comprises 2.3 residues per turn; the average length is about 20 Å or 6 residues.

Chou and Fasman define an alpha helix nucleus as a hexapeptide containing four helix forming residues and not more than one helix breaker, and a beta sheet nucleus as a pentapeptide containing three beta sheet forming residues and not more than one sheet breaker.

The amino acid sequence in the vicinity of the di-alpha linker is as follows:

| residue # | 138 | 139 | 140 | 141 | | 1 | 2 | 3 | 4 |
|---|---|---|---|---|---|---|---|---|---|
| AA (SEQ ID NO:4) | Ser | Lys | Tyr | Arg | —(XXX)$_n$— | Val (SEQ ID NO:5) | Leu | Ser | Pro |
| Helix Not | H21 | HC1 | HC2 | HC3 | | NA1 | NA2 | A1 | A2 |
| Helix Pot | 079 | 107 | 061 | 079 | | 114 | 134 | 079 | 059 |
| Sheet Pot | 072 | 074 | 129 | 090 | | 165 | 122 | 072 | 062 |

(Note: Helix- and sheet forming potentials have been multiplied by 100 for typographical reasons.)

The di-alpha linker is preferably only 1–3 amino acids. Thus, it can form an alpha helix only in conjunction with the linker "termini". A one or two residue linker, even if composed of amino acids with strong secondary structure propensities, would be unlikely to assume an alpha helix or beta sheet configuration in view of the disruptive effect of, e.g., Arg 141 or Ser 3. If the linker is 3 residues long, it would be preferable that no more than one residue be a strong alpha helix former, unless the linker also included a strong alpha helix breaker.

The amino acid sequence in the vicinity of the di-beta linker may impose more stringent constraints.

| 143 | 144 | 145 | 146 | | 1 | 2 | 3 | 4 |
|---|---|---|---|---|---|---|---|---|
| His (SEQ ID NO:6) | Lys | Tyr | His | —(XXX)$_n$— | Val (SEQ ID NO:7) | His | Leu | Thr |
| H21 | HC1 | HC2 | HC3 | | NA1 | NA2 | NA3 | A1 |
| 124 | 107 | 061 | 124 | | 114 | 124 | 134 | 082 |
| 071 | 074 | 129 | 071 | | 165 | 071 | 122 | 120 |

The di-beta linker is likely to be longer (preferably 1–9 A.A.) and therefore more susceptible to secondary structure formation. If secondary structure formation is not desired, it is desirable that the amino acid adjacent to Val-1 be an alpha helix breaker (e.g., Glycine) in view of alpha-helix propensities of Val-His-Leu. More generally, it is desirable that the linker not contain (or cooperate with the proximately linked amino acids to form) an alpha helix nucleus or beta sheet nucleus.

When secondary structure is not desired, amino acids with a high propensity toward alpha helix formation may be used in the linker if accompanied by "helix breaking" amino acids. Similarly, Beta sheet formation may be prevented by "sheet disrupting" amino acids.

Of course, prediction of secondary structure using Chou and Fasman's approach has its limitations and the ultimate test of the acceptability of a linker is whether or not the di-alpha or di-beta hemoglobin has the desired affinity for oxygen. In particular, a poly-alanine linker, despite its supposed propensity to alpha-helix formation, may well be of value since the alanine group is compact and therefore the linker should be quite flexible if secondary structure does not form.

In an especially preferred embodiment, di-alpha and beta globin genes are combined into a single polycistronic operon. The use of a polycistronic operon is not, however, necessary to practice the present invention, and the alpha (or di-alpha) and beta (or di-beta) globin genes may be expressed from separate promoters which may be the same or different.

While the preferred "genetically fused hemoglobin" of the present invention is one comprising a di-alpha and/or di-beta globin, other globin chains may be genetically fused and used in the production of multimers of hemoglobins of species other than Hgb A1 ($\alpha_2\beta_2$).

Pseudo-Octameric (Ditetrameric) Hemoglobin-like Proteins With Disulfide Bridges The ability to produce pseudotetrameric recombinant hemoglobins consisting of a single dialpha polypeptide and two beta chains (or a dibeta polypeptide and two alpha chains) provides a unique opportunity to create an asymmetric pseudotetramer from the normally symmetric pseudotetramer. Because the two alpha globin domains are expressed as a single polypeptide, it is possible to alter one of the alpha globin domains without altering the other. The result is a protein that, in its final folded state, contains two different alpha globin domains in a strict 1:1 ratio. This type of asymmetric hemoglobin molecule, with its unique chemical properties, cannot be easily constructed by any other method. A preferred embodiment of this invention would involve use of site-directed mutagenesis to substitute a cysteine residue in one of the two alpha globin domains of a di-alpha hemoglobin such as SGE1.1 (a di-alpha hemoglobin with a beta chain Presbyterian mutation) such that the cysteine would be on the surface of the folded recombinant hemoglobin molecule. A homogeneous preparation of pseudooctameric hemoglobin could then be formed through interhemoglobin linkage of two pseudotetramers either directly by simple oxidation of purified pseudotetramers or by reaction with a bridging molecule (FIG. 3).

Although direct formation of a disulfide bond between two "mono cys" tetramers is desirable in order to avoid the need for chemical crosslinking, naturally occurring reducing agents may reduce the disulfide bond in vivo at a significant rate. Preliminary experiments suggest that the rate of reduction of the bond may be influenced by the location of the cysteine mutation on the surface of the hemoglobin.

The surface cysteine mutants (MW=64 kDa) can be oxidized to the disulfide-linked dimer under oxidative conditions. This can be accomplished by stirring a concentrated solution of the expressed protein at pH 8 under pure oxygen at 4° C. or room temperature in the dark. Trace levels of transition metal ions such as $Cu^{+2}$ may be added to level below 1 uM to catalyze the oxidation (1). Formation of the 128 kDa octamer can be monitored by gel filtration. Saturation of the solution with oxygen at elevated pH should minimize autooxidation of recombinant hemoglobin.

An alternative procedure, which may be the preferred method of catalyzing this reaction, involves the use of redox buffers such as reduced and oxidized glutathione, or reduced and oxidized dithiothreitol (2). This catalysis of the reaction through disulfide interchange may be necessary to control trace transition metal catalysis (3). An second, similar approach involves conversion of the surface cysteines in the 65 kDa species to sulfonates before purification (to avoid 128 kDa species formation during purification), followed by conversion to the disulfide-linked 128 kDa species with reduced glutathione (2).

(1) Freedman, R. B. and Hillson, D. A. (1980) "Formation of Disulfide Bonds"IN: The Enzymology of Post Translational Modification of Proteins, Vol. 1, p. 157 ff. (Academic Press).

(2) DiMarchi, R., et al. (1988) Chemical synthesis of human epidermal growth factor (EGF) and human type a transforming growth factor (TGFa) IN: Peptides: Chemistry and Biology (G. R. Marshall, ed.) pp. 202–203 (Leiden:ESCOM).

(3) Creighton, TE (1978) Experimental studies of protein folding and unfolding. Prog. Biophys. Molec. Biol. 33:231–297

Multimeric Hemoglobin-Like Protiens With Other Intercysteine Linkages

It is also possible, of course, to couple two mono cys molecules with a homobifunctional crosslinking reagent resulting in linkage via nonreduceable bonds. The degree of polymerization is still controlled by the use of the mono cys di-alpha or di-beta Hgb starting material.

By using bi-, tri-, tetra-, hexa-, or octa-functional crosslinkers several properties of multimeric hemoglobin which may contribute to longer serum half life can be controlled. The crosslinkers can be designed to give a nonreducible bond between two tetramers, to yield high molecular weight multimers of n>2 psuedo-tetramers (e.g. dodecamers, etc.) and/or to drop the overall isoelectric point of a hemoglobin octamer to further increase its half life.

Correlations of molecular weight with serum half life for proteins such as IL-2, demonstrate that a significantly longer half life may be expected as the molecular weight of a protein increases, particularly above the renal filtration limit of 50–70 kDa. However, a factor potentially limiting the half life of multimeric hemoglobin formed by a disulfide link between tetramers is reduction of the cys-cys disulfide bond by endogenous thiol-reducing agents found in the serum. Estimates of small molecule thiol levels in plasma vary from 17 µM to 5 µM. The major species is reduced glutathione. Other thiol compounds in plasma include cysteine, homocysteine, and gamma-glutamyl cysteine. Thus, small molecule plasma thiols are available for reduction of disulfide bonds. This may be reflected in the diminished half life seen with antibody-ricin A chains conjugates linked by regular disulfides (6.7 hrs) relative to conjugates linked with sterically hindered, and thus less reducible, alpha-methyl disulfides (42.5 hours).

Thus, in one embodiment, the octameric hemoglobin features a nonreducible sulfur-containing crosslink such as a thioether bond or thiol-maleiimide adduct. These may substantially extend the multimer half life. Simple homobifunctional crosslinkers or polyethylene glycol (peg) derivatives would likely be useful for this purpose (see below). The reaction of a bifunctional cysteine-specific crosslinker with a mono-cys di-alpha or di-beta Hgb should limit the products of the reaction to a dumbbell-like octameric hemoglobin and unreacted hemoglobin. The reaction should be stoichiometric when the Hgb and crosslinker are present at high concentrations and the Hgb is present in a slight excess over the crosslinker maleiimides at pH 6.5–7.0. Further, there should not be substantial interference by reaction with globin lysines. The preferential reactivity of the thiols to lysines can be roughly calculated as the product of their molar ratios and the ratio of the intrinsic reactivity of a maleiimide to thiols versus amines. This product is ca. [1 cys/40 lys]×[1000]=25 at pH 7. The side products would still be octamers, with one attachment site being a secondary amine and thus might well be functionally equivalent to the S-crosslinked octamers. Hydrolysis of the maleiimide adduct at pH 7 would be slow, and the ring opening would leave the crosslink intact. The reaction of the thioether RC(=O)CH$_2$I with the sulfhydryl-bearing protein (R'SH) results in the crosslink RC(=O)CH$_2$—S—R'. The reaction of the maleiimide with the protein results in the addition of the R'SH across the double bond of the five-membered maleiimide ring, yielding a thiomaleiimide adduct.

The following are examples of homobifunctional crosslinkers that may form metabolically stable crosslinks between monocysteine pseudo tetramers:

1) 1,2-bis-(2-iodoethoxy)ethane
2) 4,4'-dimaleiimidylbenzene or N,N'-p-phenylenedimaleiimide
3) N,N'-bis-(3-maleiimido-propionyl)-2-hydroxy-1,3-propane diamine.

Longer half lives may also be obtained by increasing the apparent solution molecular weight by simply lengthening the distance between the two linked tetramers using a long crosslinking agent. The use of some potentially novel polyethylene glycol derivatives as homobifunctional crosslinkers, reacting with SGE1.1 mono-cys, may provide one mechanism for significantly increasing the molecular weight of octameric hemoglobin by virtue of the length of the crosslinker alone.

A suitable crosslinker for this purpose is

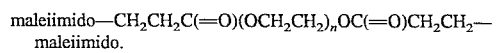
maleiimido—CH$_2$CH$_2$C(=O)(OCH$_2$CH$_2$)$_n$OC(=O)CH$_2$CH$_2$—maleiimido.

The length may be adjusted by variation of n. A few examples are given below.

| Structure | Max Length | Source |
| --- | --- | --- |
| n = 22 | ~49Å | peg –1000 |
| n = 76 | ~166Å | peg –3350 |
| n = 227 | ~499Å | peg –10000 |

Homobifunctional N-hydroxysuccinimide-activated peg has been used previously to derivatize hemoglobin. Yabuki, et al., Transfusion, 30:516 (1990). This reaction resulted in a polydisperse mixture of monomeric, dimeric, and trimeric species with an average stiochiometry of peg/hemoglobin of 6.2. However, 83% of the hemoglobin derivatized by peg was not crosslinked to another hemoglobin molecule. Control of the peg-derivitization of wild-type hemoglobin was not possible because there is no site-directed labeling of the hemoglobin starting material.

In contrast, the combination of SGE 1.1 mono-cys starting material and a peg crosslinker should yield a substantially monodisperse dumbbell (pseudo-octameric) product. The site-direction of the crosslinker attachment site should result in precise control of the apparent molecular weight, which will depend on the size of the crosslinker. Moreover, careful control of the site of the cys mutation on the surface of the recombinant hemoglobin should ensure that the functionality of the derivatized hemoglobin is maintained.

Higher Multimeric Hemoglobins

The above crosslinkers all involve the attachment of one tetramer at each end of a crosslinker. It may be advantageous to attach more than two tetramers to a single crosslinker to yield more oxygen-carrying capacity and to further increase the molecular weight.

A multimeric hemoglobin may be assembled with the aid of one or more linker peptides, each having a controlled number of reactive sites to which a cysteine residue of a hemoglobin tetramer or pseudotetramer may be attached, directly or indirectly.

With a peptide linker of considerable length, there is the concern that it will be degraded by serum proteases, thus degrading the multimeric hemoglobin into its component tetramers. This problem, if significant, may be remedied by use of a peptide linker which is less susceptible to proteolysis. A non-exhaustive list of such linkers would include peptides composed of D-amino acids, peptides with stable, extended, secondary structures, and branched peptides.

In the case of peptides composed of D-amino acids, use of D-Glu or D-Asp is particularly preferred.

A number of stable, extended, secondary structures are known. The simplest is possibly polyproline. Another example is the 2-stranded coiled coil, in which two peptide chains intertwine. A 4-helical or a 4-stranded coiled coil are also possiblities.

Branched structures, such as those obtained by derivation of the secondary amino group of lysine, are typically resistant to protease.

If desired, several of these approaches may be combined. For example, several coiled coils may lead off a branched structure, or D-amino acids may be incorporated into a coiled coil.

A hypothetical 4-tetramer coiled-coil linker complex is shown in FIG. 4(a). Design and synthesis of these coiled coil peptides has already been explored (for an example see Cohen and Parry, Proteins, 7:1–15 (1990)). The rationale for a coiled coil is that two intertwined alpha helices will be less sensitive to proteolytic cleavage than a single naked secondary structure like an extended peptide (rapidly cleaved by proteases), an alpha helix or a beta sheet.

Using molecular modeling, an internal disulfide may be designed in the center of a bi-functional coiled coil linker such that the strands are covalently attached. This should stabilize formation of the correct coiled coil crosslinker before mono-cys di-alpha or di-beta Hgb (e.g., sge1.1 cys) is attached. Additionally, a tri-functional crosslinker can be stabilized by use of a orthogonally-protected lysine (lys-FMOC) rather than a disulfide in the center of a proteolytically inert secondary structure. A polyproline helix can be used as the linker, and can be stabilized by branching the synthesis at the lys-FMOC after removal of the side chain. The three remaining lysines in the branched peptide would then be iodoacetylated to site-specifically attach a thiol-reactive group using either iodoacetic anhydride or N-succinimidyliodo-acetate and subsequently reacted with sge1.1-cys. An analogous tetra-functional crosslinker could be synthesized by inserting 1–2 prolines between two internal branching lysines to rotate them such that the two internal branching chains growing off the orthogonally protected lysines head in (nearly) opposite directions. Analogous structures could be made using D-glutamate(E) or D-aspartate(D) to provide protease resistance, and these would form an extended polyanionic chain at pH 7.

The sequence of a hypothetical alpha-helical coiled coil is modified from that given in Semchuck, et al., in Peptides: Chemistry, Structure and Biology; 566 (Rivier and Marshall, eds:1990), to leave only two lysines (K) at each end: Ac-Lys-Cys-Ala-Glu- Leu-Glu-Gly-Arg-Leu-Glu-Ala-Leu-Glu-Gly-Arg-Leu-Glu-Ala-Leu-Glu- Gly-Arg-Leu-Glu-Ala-Leu-Glu-Gly-Arg-Leu-Glu-Ala-Leu-Glu-Gly-Lys-Leu-Amide (SEQ ID NO:8)

This coiled coil should have about 10 turns of a helix and thus will be ca. 54 Å long, allowing two tetramers to attach on each side without steric interference. The exact sequence and length to allow appropriate placement of 4 tetramers would depend on the results of molecular modeling.

Suggested trifunctional and tetrafunctional crosslinkers are diagrammed below.

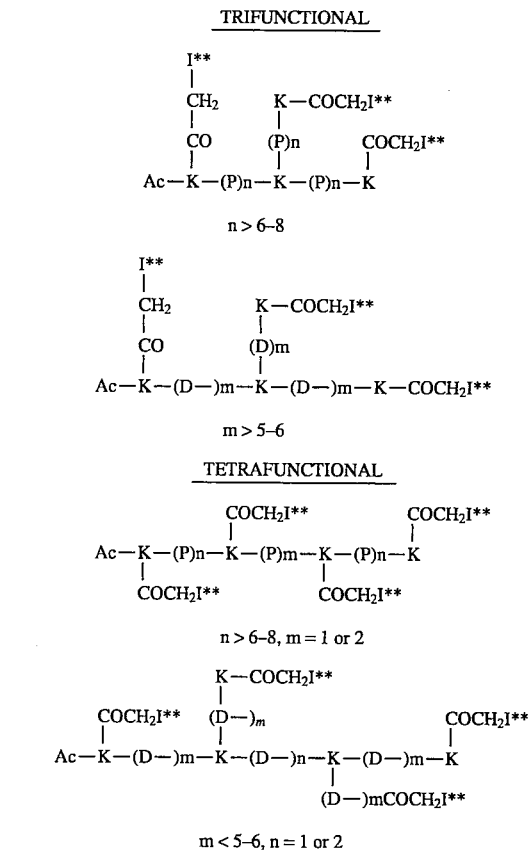

(D could be a D-amino acid for greater protease resistance)
(** indicates a reactive site; K is a lysine; P is Proline, Ac is acetyl; I is iodine; D is D- or L-aspartate; K's are on opposite faces so the pseudotetramers attach on opposite faces of the coiled coil.)

See also FIG. 4(a).

Another possibility is an 8-hemoglobin complex (FIG. 4(b)). The rationale for considering this sort of complex is that it may be the way to obtain a very long halflife, due to the extreme stability of the "crosslinker" and the substantially higher molecular weight of the complex. The crosslinker might take the form of a doubly branched coiled coil, with a Lys(FMOC) replacing an Arg in the middle of the chain to allow the branching, and with a polyproline helix or other protease resistant secondary structure comprising the branching moiety. This structure could allow attachment of 6 SGE1.1's per crosslinker. Alternatively, a 4-helical bundle protein (See FIG. 4(*c*)) or 4-stranded coiled-coil such as those synthesized by DeGrado, Science, 243:622 (1989), with each helix in the 4-helical bundle containing the consensus sequence Gly-Glu-Leu-Glu-Glu-Leu-Leu-Lys-Lys-Leu-Lys-Glu-Leu-Leu-Lys-Gly (SEQ ID NO:9) the helices being linked by three PRR or RPR loops, could be utilized as a suitable core for the linker. This is one of the most stable proteins known, with a G=−22 kcal/mole separating the folded from the unfolded state. Each helix would be 4+ turns or ca. 22 Å long. Since this may not be enough room to fit two hemoglobins with one anchored at each end of the helix, they might have to be attached to different faces of the same helix, to lysines placed at each end of the polar face of each helix. Each helix is amphipathic; this should allow relative freedom to have a total of 8 lysines (and no more) and to change the remaining lysines to arginines. At least two of the i, i+4 salt bridges per helix would be retained for stability of the protein. Attachment of an externally crosslinkable cysteine-bearing tetramer could be via iodoacetylation of the lysine epsilon amino groups and then reaction with the thiol group of the cysteine.

An example of a modification that might allow more room between tetramers would be addition of one turn of the helix to the N-terminus of the A and C helices and the C-terminus of the B and D helices. This and similar modifications would be subject to modeling and experimental constraints.

Analogous core proteins could be made as mutants of known 4-helical bundle proteins such as myohemerythrin or apoferritin, with the surface residues changed so that 8 (or more if topologically possible) lysines (2 per helix) exist on the surface for subsequent modification and attachment of the tetramer.

Poly(tetrameric) Hemoglobins with Reduced Isoelectric Points

If the isoelectric point of the whole crosslinked conjugate also affects the serum half life, via electrostatic exclusion from the renal filter's "pore", additional negative charges could be included in the crosslink itself (rather than in the hemoglobin, which could change the function of the molecule) to drop the isoelectric point of the overall crosslinked particle. An additional benefit of this might be reduced uptake by the reticuloendothelial system, this uptake being a function of pI for cationized albumin.

We have preliminary evidence from succinylation of SGE1.1 which correlates the number of modified lysines with isoelectric point. This gives a rough estimate of the number of lys to glu and/or lys to asp mutations which may be necessary to reach a pI of 5 or less, the pI range which we expect we need to significantly extend half life. We believe that as many as 8 lysines may have to be modified (a total shift in charge of 16 units) to drop the pI roughly 2 units. It should be less disruptive of the functional properties of hemoglobin to do this via a eptide crosslinker rather than by mutation of the alpha and beta globin subunits proper. However, some mutations could be made in the crosslinker and the remainder in the subunits. As before, the SGE1.1-cys would be attached to iodoacetylated lysine epsilon amino groups by reaction at pH 6.5–7.0.

For human serum albumin in the rat, the half life varied roughly linearly with the pI of the protein, from ca. 4.6 hours for native albumin (pI=4) to 0.8 hrs at a pI above 9.5. Clearance was probably by multiple mechanisms, including potentially increased uptake into the reticuloendothelial system with increased pI. For rat trypsinogens, the difference in serum half life between versions with a pI of 5.-0 ($t_{1/2}$ of 4 min) was even larger. Thus a lower pI clearly appears to be an important variable in the serum half life of these proteins.

The following table gives examples of crosslinkers between mono-cys tetramers which should diminish the isoelectric point of the overall complex.

| Source | Sequence | |
|---|---|---|
| polyasp or polyglu | 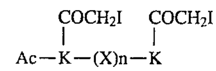  | n probably ≧ 10–12, X = D or E− |
| " | 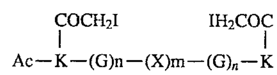  | n > 2 to provide flexibility at each terminus, m ≧ 10–12, X = $D^-$ or $E^-$ |
| " | 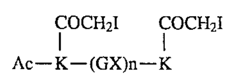  | n ≧ 5–6, m ≧ 10–12, X = D− or E− |

A number of the proposed crosslinkers could combine at least two, or possibly three of these attributes for potential additive effects.

It is possible that the unique amine groups in the peptide crosslinkers could be directly iodoacetylated during the peptide synthesis by treating iodoacetic acid as the last amino acid to be added, after deprotecting the lysine amine groups on the resin. In this case, the lysines would be orthogonally protected with N-FMOC or N-nitropyridinesulfenyl groups, or with BNPEOC. This could greatly simplify their synthesis.

Alternate methodologies to iodoacetylation as part of the synthesis could include the reaction of either sgel.1SH or the peptide crosslinker with a heterobifunctional crosslinker specific for sulfhydryls and amines, such as sulfo-SMCC or similar reagents available from Pierce Chemical Co. (Rockford, Ill.).

Genetically Fused Poly(tetrameric) Hemoglobins

Another approach to the preparation of multimeric (e.g., polytetrameric) hemoglobin involves the genetic fusing of individual tetramers utilizing other linkers. Two or more tetramers may be linked, depending on the desired molecular weight and the efficiency of folding of the final molecule. The dialpha (or dibeta) subunits from different tetramers of a di-alpha or di-beta Hgb might be genetically fused together into an extended polypeptide which would link the individual pseudotetrameric domains.

Proteolytically stable extended polypeptide linkages can be envisioned. Desirable linker features might include 1) a number of glycines at each end to allow flexibility in entering the dialpha (or beta) terminal domains, and to decouple the linker secondary structure from that of the dialpha (or beta) terminal domains; 2) stiffness to separate tetramers, obtainable by an extended structure such as a polyproline helix or by polyglutamate or polyaspartate; and 3) inertness to proteases (vide supra or as in a collagen sequence). Several examples of such sequences are listed below. Obviously any other of the peptide linkers mentioned in this specification could be tried after first sterically modeling the fused-dialpha (or dibeta) termini environment. The links would go from the C-terminus of one dialpha to the N-terminus of the next and would be synthesized as a single gene. Besides modeling segments of protease-resistant or negatively charged secondary structure, one or more of the Artemia linkers should be modeled between tetramers. The beta chains could also be joined in this fashion, although the results of this on protein function would be unknown. It might be feasible to make an intermolecular di-beta (sge1.1) with or without additional intrachain crosslinkages.

| Source | Sequence |
|---|---|
| polyproline helix | di ∝ or β C term-(G)n-(P)n-(G)n-di ∝ or β N terminus n probably ≧ 3, m probably ≧ 10–12 |
| polyaspartate or glutamate | —(G)n—(D)n—(G)n— (should drop pI of complex) |
| Artemia linker (example) | —(G)n—Leu—Arg—Arg—Gln—Ile—Asp—Leu—Glu—Val—Thr—Gly—Leu—(G)n-; n ≧ 0 [SEQ ID NO:30] |
| a helical coiled coil | —(G)n-Lys—Cys—Ala—Glu—Leu—Glu—Gly—Lys—Leu—Glu—Ala—Leu—Glu—Gly—Lys—Leu—Glu—Ala—Leu—Glu—Gly—Lys—Leu—Glu—Ala—Leu—Glu—Gly—Lys—Leu—Glu—Ala—Leu—Glu—Gly— ← not used to terminus (should form octamer with coiled-coil crosslink) [SEQ ID NO:31] |

We have determined the minimum of the intertetramer linker as follows. Two structures of human hemoglobin $A_o$ (either both in the oxy form or both in the deoxy form) taken or assembled from the Brookhaven Protein Data Bank were docked as close together as possible without van der Waals overlap between any residues, using the program Insight (Biosym. Inc., San Diego, Calif.). The distance from the alpha chain C terminal residue arg 141 to the amino terminal nitrogen of the alpha chain N terminal residue val 1 (in one structure) was then measured. This distance was ca. 22 Å when both molecules had the oxy structure and ca. 18 Å when both were in the deoxy structure. In the oxy and deoxy structures, the valine at the alpha chain N terminus is exposed at the side of a cleft in the structure, while the arg carboxylate is at the bottom of the cleft. Thus it is possible to genetically fuse these two termini without suffering a large structural displacement of residues around either terminal amino acid. A suitable intertetramer linker will be at least 18–22 angstroms long, preferably longer in order to give the structure additional flexibility. There is no fixed upper limit on the length of the linker, however, the longer the linker, the more susceptible it is to protease, and, if the molecule appears large enough, it may be phagocytosed by macrophage of the reticuloendothelial system. A few examples of suitable linkers are listed below.

An alternative fusion may be envisioned between a truncated alpha chain in one hemoglobin and the N terminal alpha val 1 in the second hemoglobin. The first molecule could be truncated at ser 138, which intermolecular N terminal to C terminal distance is about 17 Å (deoxy) and 22 Å (oxy), and examples of genetically inserted linkers spanning this distance are listed below.

Thus two hemoglobin molecules could be linked (by fusing two intermolecular alpha domains) to generate a fusion protein approximately twice the size of normal human hemoglobin. An additional intramolecular crosslink, as introduced into rHb1.1 to prevent dissociation of hemoglobin into dimers, could be included as well, giving a fusion of four alpha domains.

We expect that the genetically inserted links will be stable in the presence of proteases, due to the steric occlusion by the two hemoglobins surrounding the linkage. This resistance may be further enhanced by the use of glycines, bonds between which may be less susceptible to proteases, since most proteases have side chain specificity for residues other than glycine (which has only a hydrogen as a sidechain, and thus may result in a poor Km of this substrate for a protease). A polyproline helix may also be used as a linker to enhance stability to proteases. Fusion of a polyglutamate or polyaspartate as a linker might allow a much lower isoelectric point for the complex, and thus a longer serum half life.

| | Intertetrameric Linkers for Inclusion in Pseudooligomeric Polypeptides | | |
|---|---|---|---|
| Linker | end-to-end Distance | conformation | Comments |
| -(gly)$_7$-(SEQ ID NO: 32) | 25Å | extended | minimal length for gly linker to span termini in both oxy and deoxy structures. Longer linkers (up to 20–50 residues) may also work favorably. |
| -(gly)$_{1-3}$(ala)$_{12}$ -(gly)$_{1-3}$-(SEQ ID NO:33) helix | 20Å–40Å | Ala in right handed alpha helix | the Gly are added for flexibility and minimal disturbance of Hb structure around their fusion with the N and C termni. Length is dependent on the number of glycines and the degree of extension |
| -(gly)$_{1-3}$(pro)$_{12-16}$ -(gly)$_{1-3}$(SEQ ID NO: 34) proline helix | 21–48Å | pro in a left handed poly-proline helix | 12, 14, 16 prolines. Length dependent on number of prolines and glycines |
| (gly)$_{1-3}$- (asp)$_{1-30}$- (gly$_{1-3}$)-(SEQ ID NO: 35) | 26–49Å | | Asp residues add negative charges |

Other residues could be substituted into these linkers while leaving their length essentially the same, including complete linkers taken from the sequence of other known human proteins such as hemoglobin, to prevent any recognition of the multimer as a foreign protein.

Use of linkers with a maximal length more than 18 Å and less than 22 Å may differentially stabilize the deoxy structure, and may result in a lowered oxygen affinity for the multimer.

Octameric Hemoglobins Formed Without Use of an Pseudooligomeric Globin

It is possible to produce an octameric hemoglobin, without substantial production of higher multimers, by suitable cysteine mutation of either the alpha or beta chain (see FIG. 5).

Hemoglobin mutants containing one X to cys mutation in the beta chain gene (giving two per tetramer) or in the alpha chain gene (also giving two per tetramer), in which the residues mutated to cysteine are both on or very close to the surface of the subunit add are as close to the dyad axis separating the subunits, may form octamers (two hemoglobins) linked by two disulfides. Polymerization of such mutants should be retarded by the proximity of the two disulfides to each other, such that after one disulfide is formed, a third incoming hemoglobin will be *sterically hindered from reacting with either free cysteine on the two original hemoglobins.

Because it is possible that this mutant may form higher order polymers (rather than simply the octamer), a diluted solution may be used in vitro for formation of disulfide bonds. The kinetics of polymerization of hemoglobin should be at least second order (or a higher order) in hemoglobin concentration, while after one disulfide is formed, the formation of the second disulfide between two tetramers should be zero order in hemoglobin. Thus the ratio of polymerized product to octamer should diminish as the hemoglobin concentration is decreased. If formation of octamers is done under oxygenated conditions, the yield of octamers vs. polymers may increase further, since the distance between the two cys mutations is less in every case in the oxy hemoglobin structure than in the deoxy structure.

A list of preferred mutation sites in both the beta chain and the alpha chain is provided below:
Beta and alpha chain mutation sites for x to cys mutations to form disulfide-bond linked octameric hemoglobin.

| Chain/ Mutation | Old Distance (Å) | New Distance (Å) | Comment |
| --- | --- | --- | --- |
| beta Asn 80 to cys | 22 | 18 | no listed deleterious mutations, asn 80 is on surface |
| beta Asp 70 to cys | 24 | 22 | Hb Tampa[a] (asp to tyr) has no major abnormal property listed; Hb G-His-Tsou (asp to gly) has increased $O_2$ affinity; is on surface |
| alpha Asn 78 to cys | 24 | 20 | on surface; no major[a] abnormal properties of known mutations of asn 78 |
| alpha Asp 75 to cys | 22A | 18 | on surface; no major abnormal properties of known mutations of asp 75 |
| alpha Asp 74 to cys | 26 | 20 | on surface; no major[a] abnormal properties of known mutations of asp 74 |

[a]R. N. Wrightstone. Policies of the International Hemoglobin Information Center (IHIC), Comprehensive Sickle Cell Center, Medical College of Georgia. 1988.

Gene Construction and Expression

The DNA sequences encoding the individual polypeptide chains may be of genomic, cDNA and synthetic origin, or a combination thereof. Since the genomic globin genes contains introns, genomic DNA must either be expressed in a host which can properly splice the premessenger RNA or modified by excising the introns. Use of an at least partially synthetic gene is preferable for several reasons. First, the codons encoding the desired amino acids may be selected with a view to providing unique or nearly unique restriction sites at convenient points in the sequence, thus facilitating rapid alteration of the sequence by cassette mutagenesis. Second, the codon selection may be made to optimize expression in a selected host. For codon preferences in *E. coli*, see Konigsberg, et al., PNAS, 80:687–91 (1983). Finally, secondary structures formed by the messenger RNA transcript may interfere with transcription or translation. If so, these secondary structures may be eliminated by altering the codon selections.

Of course, if a linker is used to genetically crosslink subunits, the linker will normally be encoded by a synthetic DNA.

The present invention is not limited to the use of any particular host cell, vector, or promoter. The host cell may be prokaryotic or eukaryotic, and, in the latter case, may be a plant, insect or mammalian (including human) cell. The cell may also be of any suitable tissue type, including, inter alia, an erythrocyte. However, the preferred host cells are bacterial (especially, *E. coli*) and yeast (especially *S. cerevisiae*) cells. The promoter selected must be functional in the desired host cells. It preferably is an inducible promoter which, upon induction, provides a high rate of transcription. A preferred bacterial promoter is the Tac promoter, a trp/lac hybrid described fully in DeBoer, U.S. Pat. No. 4,551,433 and commercially available from Pharmacia-LKB. Other promoters which might be used include the temperature sensitive lambda $P_L$ and $P_R$ promoters, as well as the lac, trp, trc, pIN (lipoprotein promoter and lac operator hybrid), gal and heat shock promoters. The promoter used need not be identical to any naturally-occurring promoter. Guidance for the design of promoters is provided by studies of promoter structure such as that of Harley and Reynolds, Nucleic Acids Res., 15:2343–61 (1987) and papers cited therein. The location of the promoter relative to the first structural gene may be optimized. See Roberts, et al., PNAS (USA), 76:760–4 (1979). The use of a single promoter is favored. Suitable yeast expression systems are described in detail elsewhere in this specification.

The vector used must be one having an origin of replication which is functional in the host cell. It desirably also has unique restriction sites for insertion of the globin genes and the desired regulatory elements and a conventional selectable marker. A vector may be modified to introduce or eliminate restriction sites to make it more suitable for futher manipulations.

The component polypeptide chains of the multimeric hemoglobin may be expressed either directly or as part of fusion proteins. When expressed as fusion proteins, the latter may include a site at which they may be cleaved to release the globin-related moiety free of extraneous polypeptide. If so, a site sensitive to the enzyme Factor Xa may be provided, as taught in Nagai and Thorgenson, EP Appl 161,937, incorporated by references herein. Alternatively, the fusion proteins may be synthesized, folded and heme incorporated to yield a hemoglobin analogue. The direct expression of the component polypeptides is desirable.

In bacterial mRNA, the site at which the ribosome binds to the messenger is a polypurine stretch which lies 4–7 bases upstream of the start (AUG) codon. The consensus sequence of this stretch is 5' . . . AGGAGG . . . 3', and is frequently referred to as the Shine-Dalgarno sequence. Shine and Dalgarno, Nature, 254: 34 (1975). The exact distance between the SD sequence and the translational start codon, and the base sequence of this "spacer" region, affect the efficiency of translation and may be optimized empirically. Shepard, et al., DNA 1: 125 (1985); DeBoer, et al., DNA 2: 231 (1983); Hui, et al., EMBO J., 3: 623 (1984).

In addition, the SD sequence may itself be modified to alter expression. Hui and DeBoer, PNAS (USA), 84:4762–66 (1987). Comparative studies of ribosomal binding sites, such as the study of Scherer, et al., Nucleic Acids Res., 8:3895–3907 (1980), may provide guidance as to suitable base changes. If the hemoglobin is to be expressed in a host other than *E. coli*, a ribosomal-binding site preferred by that host should be provided. Zaghloul and Doi, J. Bacteriol., 168:1033–35 (1986).

Any host may be used which recognizes the selected promoter and ribosomal binding site and which has the capability of synthesizing and incorporating heme. Bacterial and yeast hosts are preferred.

The intracellularly assembled hemoglobin may be recovered from the producing cells and purified by any art-recognized technique.

Polycistronic Expression in Bacteria

While not required, it is desirable that the subunits, when expressed in bacteria, be co-expressed in the same cell, and it is still more preferable that they be co-expressed polycistronically. A polycistronic operon encodes a single messenger RNA transcript having one promoter sequence, but two or more pairs of start and stop codons that define distinctly translatable sequences. Each such sequence is known as a "cistron," and the polypeptides corresponding to the cistrons are thus co-expressed under the control of the single promoter.

The majority of bacterial operons are polycistronic, that is, several different genes are transcribed as a single message from their operons. Examples include the lactose operon with three linked genes (lacZ, lacY and lacA) and the tryptophan operon with five associated genes (trpE, trpD, trpC, trpB, and trpA). In these operons, the synthesis of messenger RNA is initiated at the promoter and, within the transcript, coding regions are separated by intercistronic regions of various lengths. (An operon is a cluster of genes that is controlled as a single transcriptional genetic unit). Translational efficiency varies from cistron to cistron. Kastelein, et al., Gene, 23:245–54 (1983).

When intercistronic regions are longer than the span of the ribosome (about 35 bases), dissociation at the stop codon of one cistron is followed by independent initiation at the next cistron. With shorter intercistronic regions, or with overlapping cistrons, the 30S subunit of a terminating ribosome may fail to dissociate from the polycistronic mRNA, being instantly attracted to the next translational initiation site. Lewin, Genes, 143–162 (John Wiley & Sons: 1977).

Unlike bacterial mRNAs, eukaroyotic mRNAs are generally monocistronic in nature. Lewin, *Gene Expression*, 157.

In one embodiment, expression of the genes encoding two or more component polypeptides are driven by a single promoter, and the genes are arranged so that a polycistronic messenger RNA transcript is transcribed, from which separate globin-like polypeptides are subsequently translated. However, the present invention includes the co-expression of the different polypeptides from separate promoters, i.e., the host transcribes separate alpha and beta globin mRNAs.

Ideally, alpha and beta globin-like domains are expressed in stoichiometrically equal amounts. While use of a single promoter does not guarantee equality, it eliminates one unbalancing influence—differences in transcription owing to differences in promoter strength and accessibility. If differences in promoter strength were minimized by use of two identical promoters on the same plasmid, plasmid stability would be reduced as there would be a propensity toward recombination of the homologous regions.

Preferably, the alpha and beta globin-like domain-encoding genes are arranged so that the ribosome will translate the alpha globin cistrons first. The rationale is that there is some basis for believing that alpha globin affects the folding of beta globin. Nonetheless, the position of the genes may be switched so that a beta globin-like domain is synthesized first.

The stability of the polycistronic mRNA transcript, the efficacy of its translation into alpha and beta globin-like polypeptides, and the folding of the globin chains into tetrameric hemoglobin may be modified by varying the length and base sequence of the intercistronic regions (the region lying between the stop codon of one cistron and the start codon of the next cistron), the phasing of a second cistron relative to a first cistron, and the position and sequence of the ribosomal binding site for the one cistron relative to the preceding cistron.

In a preferred embodiment, the alpha and beta globin-like polypeptides genes are each preceded by a short "introductory" cistron or "ribosomal loader" which facilities the subsequent translation of the globin cistron. In FIG. 2, region A contains two cistrons and a Shine-Delgarno sequence preceeding each cistron. The first Shine-Delgarno sequence (SD#1) is bound by the ribosome, which then translates the first cistron, a short, cistron encoding an octapeptide. (This cistron is referred to as an "introductory" cistron or ribosomal loader.) The second cistron is a globin gene, in this case, an FX alpha-globin gene. The Shine-Delgarno sequence (SD#2) for facilitating translation of the second cistron actually lies within the first cistron. For this reason, the two are said to be "translationally coupled". Region B is identical in structure, except that the second cistron encodes FX-beta globin. Between regions A and B is a 43-base intercistronic region. The introductory cistrons of regions A and B correspond to the first cistron of the two-cistron expression system denoted pCZ144 in Schoner, et al., Meth. Enzymol., 153: 401–16 (1987). The present invention is not, however, limited to the particular "starter" cistron taught by Schoner, et al.; other introductory cistrons that allow for restart of high level translation of a following cistron may be used.

Guidance as to the design of intercistronic sequences and as to the location of SD sequences may be obtained by comparing the translational efficiency of spontaneous or controlled mutants of the same polycistronic operon, as exemplified by Schoner, et al., PNAS, 83:8506–10 (1980). It is also possible to look for consensus features in the intercistronic regions of different operons. McCarthy, et al., EMBO J., 4: 519–26 (1985) have identified a translation-enhancing intercistronic sequence in the *E. coli* atp operon.

The present invention is intended to reduce or avoid the localization of the hemoglobin or its component polypeptides into inclusion bodies. Consequently, a further feature of the invention is that the functional hemoglobin is substantially found (preferably over 80%) in the soluble fraction of the cell. It appears that with this invention, over 90% of the functional hemoglobin can be so directed when alpha$_2$ beta$_2$ hemoglobin is assembled from alpha- and beta-globin chains co-expressed from a tetracistronic operon as described herein. With di-alpha, beta$_2$ hemoglobin, nearly 100% is soluble when expression is induced at 25° C. and less at higher induction temperatures. These percentages reflect the percent of all di-alpha and beta chains found in the soluble fraction of the cell and not actual recovery of protein from the cell.

Expression in Yeast

In another embodiment the present invention relates to the production of hemoglobin-like molecules in yeast. Our preferred host for expression in yeast is *Saccharomyces cerevisiae*. However, other fungi or yeast may be used for the purpose, such as strains of Aspergillus or Pichia. For yeast to be a suitable host it must be capable of being transformed with recombinant vectors, either replicating or integrating types. This allows the insertion of the desired DNA sequence for the gene of interest. It must also be capable of high density cell growth, in appropriate volume to provide sufficient cell mass to isolate the desired gene product from the desired reaction vessels, where ideally the growth would be easily controlled by several parameters including nutrient formulation, agitation and oxygen transfer and temperature. It is also desirable to be able to induce the expression of protein synthesis with the manipulation of the media, temperature, or by the addition or consumption of certain chemicals. Finally, to be a suitable host, the yeast must be capable of producing recombinant proteins, preferably in excess of 1% of the total cell protein. This allows more facile isolation of the desired recombinant protein.

Either a haploid or a diploid strain of *S. cerevisiae* may be used. For example, the following diploid strains are preferred:

BJY3505 x RSY330
BJY3505 x BJY 1991

Other matings may likewise be used in practicing the present invention.

The use of protease-deficient strains may also be advantageous.

Yeast expression systems can be divided into two main categories: (1) Systems designed to secrete protein and (2) system designed for the cytoplasmic expression of proteins. At present, cytoplasmic expression is preferred since the yeast cells fold together the globin chains and incorporate heme to produce hemoglobin in vivo. However, it is possible to separately express and secrete the alpha and beta globin chains and assemble hemoglobin in vitro.

The globin genes must be placed under the control of a suitable promoter. The commonly used yeast promoters generally fall into two broad categories: regulated and constitutive. Constitutive promoters that are in wide use include GAP, PGK (phosphoglycerate kinase) and the α-factor promoter. Regulated promoters have also been used and these include the yeast metallothionein promoter (regulated by copper), the Gal1-10 promoter, GAL7 promoter (regulated by galactose and glucose) the ADHII promoter (regulated by ethanol and glucose) the PH05 promoter (phosphate regulation) and several hybrid promoters such as PH05-GAP, GAL-PGK, ADHII-GAP, and GAL-CYC1.

The use of a GAL-GAP hybrid promoter is preferred. Both elements (the GAL$_{UAS}$ and the GAP transcriptional initiation site) are well understood. Studies on the mechanisms of transcriptional regulation of the GAL regulon have been fairly extensive. The galactose regulon includes five genes that encode enzymes required for the utilization of galactose. Four of these genes (GAL1, GAL7, GAL10, and GAL2) are expressed only in the presence of galactose. Galactose induction does not occur in the presence of glucose unless the yeast strain bears a mutation in the REG1 gene. The GAL1, 7, 10 and 2 genes are regulated by at least two other genes, GAL80 and GAL4. The GAL4 gene is a transcriptional activator protein that activates mRNA synthesis from the GAL1, 7, 10 and 2 upstream activator sequences (UAS$_{GAL}$). Although GAL4 is constitutively expressed, it is functionally silent in the absence of galactose. Repression of GAL4 activity, in the absence of galactose is maintained by the product of the GAL80 gene. The GAL80 protein apparently interacts physically with GAL4 to prevent transcriptional activation. Presumably galactose or a galactose derivative prevents this interaction to allow GAL4 mediated induction.

Haploid strains of *S. cerevisiae* have three different genes encoding the enzyme glyceraldehyde-3-phosphate dehydrogenase (GAP). These genes have been designated TDH1, TDH2 and TDH3 and each is present as a single copy per haploid genome. The TDH3 gene produces approximately 60% of the cell's GAP enzyme and TDH1 and 2 produce about 12% and 28%, respectively (McAllister, L and M. J. Holland, 1985. J. Biol Chem, 260: 15019–15027). Holland's group (Holland et al. 1981. J. Biol Chem, 256:1385–1395; and Holland et al. 1983. J Biol Chem 258:5291–5299) has cloned and characterized the three GAP genes of *S. cerevisiae*. The clones have been designated pGAP11, pGAP63, and pGAP491. pGAP491 corresponds to the TDH3 gene and is therefore, the most highly expressed.

This promoter is commonly used as a 600–850 bp fragment and is essentially un-regulated. In its long form this is a very powerful promoter. The form we are using consists of only −200 bp 5' of the translational initiation site. This form, with no added enhancer sequences is substantially less active than the longer form of the promoter (Edens, L. et al. Cell, 37:629 (1984)). Our addition of the GAL enhancer region confers both regulation and high levels of expression. With only the GAP491 promoter, alpha and beta globin were produced at a level of less than 0.2% total cell protein; with the GALGAP491 hybrid promoter, expression jumped to 7–10% total cell protein.

Several other hybrid promoters are of particular interest: GAL-SIGMA; SIGMA-GAP; GAL-EF III; SIGMA-EF III.

One could easily conceive of other promoter systems that would also work. This would include, but not be limited to, a variety of constitutive promoters. For example, the yeast mating factor∝ (MF∝) promoter or the mating factor a promoter MF(a), the phosphoglycerate kinase promoter (PGK), hexokinase1, hexokinase2, glucokinase, pyruvate kinase, triose phosphate isomerase, phosphoglycerate isomerase, phosphoglycerate mutase, phosphofructose kinase or aldolase promoters may all be used. In short, any well expressed yeast promoter may work for expression of hemoglobin in yeast. A wide variety of naturally occurring, regulated promoters could also be used, for example: GAL1-10, GAL7, PHO5, ADHII have all been used to produce heterologous proteins in yeast. A variety of synthetic or semi-synthetic yeast promoters could also be employed such as GAL-PGK, GAL-MF∝-1, GAL-MFa1, GAL-SIGMA. ADHII regulatory sequences could also be coupled to strong transcriptional initiation sites derived from a variety of promoters. The PHO5 regulatory sequence or the sigma element regulatory sequences could also be used to construct powerful hybrid promoters. In addition to yeast promoters, it is conceivable that one could use a powerful prokaryotic promoter like the T7 promoter. In this case, one could place the T7 polymerase under the control of a tightly regulated yeast promoter. Induction of the phage polymerase in yeast cells bearing hemoglobin genes under T7 promoter regulation would allow transcription of the genes by this very efficient phage polymerase.

Because most of the yeast regulatory sequences described above serve as targets for proteins that are positive regulators of transcription, it is conceivable that these proteins may limit transcription in situations where the target sequence is present in many copies. Such a situation may obtain with vectors such as pC1B, pCIT, pC1U or pC1N which may be present in excess of 200 copies per cell. Over-expression of the positive regulator (for example GAL4) may result in enhanced expression. It is possible to construct a strain in which the GAL4 gene is altered to remove its promoter and the promoter replaced with the GAL7 or GAL1-10 promoters, both of which are transcribed more efficiently than the GAL4 promoter. In this situation, the positive transcriptional activator protein GAL4 would be expressed at elevated level at the time hemoglobin expression was induced.

The consensus sequence for higher eukaryotic ribosome binding sites has been defined by Koyak (Cell, 44:283–292 (1986)) to be: $G^{AA}{}_G$CCAUGG (SEQ ID NO:10). Deviations from this sequences, particularly at the −3 position (A or G), have a large effect on translation of a particular mRNA. Virtually all highly expressed mammalian genes use this sequence. Highly expressed yeast mRNAs, on the other hand, differ from this sequence and instead use the sequence AAAAAUGU (Cigan and Donahue, Gene, 59:1–18 (1987)). The ribosome binding site that we use for expression of the $\propto$ and β-globins corresponds to the higher eukaryotic ribosome binding site. It is within the contemplation of this invention to systematically alter this RBS to test the effects of changes that make it more closely resemble the RBS of yeast. It should be pointed out, however, that alterations at the −2, −1 and +3 positions, in general, have been found to only slightly affect translational efficiency in yeast and in mammals.

Intracellular expression of genes in S. cerevisiae is primarily affected by the strength of the promoter associated with the gene, the plasmid copy number (for plasmid-borne genes), the transcription terminator, the host strain, and the codon preference pattern of the gene. When secretion of the gene product is desired, the secretion leader sequence becomes significant. It should be noted that with multicopy plasmids, secretion efficiency may be reduced by strong promoter constructions. Ernst, DNA 5:483–491 (1986).

A variety of extrachromosomally replicating vectors (plasmids) are available for transforming yeast cells. The most useful multicopy extrachromosomal yeast vectors are shuttle vectors that use a full length 2μ-circle combined with an E. coli plasmid. These vectors carry genes that allows one to maintain the plasmid in appropriate yeast mutants and antibiotic resistance markers that allow selection in E. coli. Use of the full-length 2μ-circle, in contrast to vectors containing only a partial 2μ sequence, generally results in much higher plasmid stability, particularly in yeast strains that have been cured of endogenous 2μ plasmid. The pC series of vectors described herein are vectors of this type.

Strains could also be constructed in such a way that the GALGAP hemoglobin expression cassettes were integrated into chromosomes by using yeast integrating vectors. Although the copy number of the hemoglobin genes would be lower than for plasmid vectors, they would be quite stable and perhaps; not require selection to be maintained in the host cell. Yeast integrating vectors include Yip5 (Struhl, et al, PNAS, 76:1035–39, 1979), Yip1 (Id.), and pGT6 (Tschumper and Carbon, Gene, 10:157–166, 1980). For information on these and other yeast vectors, see Pouwels, et al., *Cloning Vectors, A Laboratory Manual* (Elsevier, 1985).

The genes encoding the desired globin-like domains may be introduced by separate plasmids, or both upon the same plasmid.

Highly expressed yeast genes show a very high codon bias. The genes encoding glyceraldehyde-3-phosphate dehydrogenase and ADH-I, for example, show a 90% bias for a set of 25 codons. Highly expressed yeast genes (>1% of the total mRNA) have yeast codon bias indices of >0.90. Moderately expressed genes (0.1–0.05% of the total mRNA) have bias indices of 0.6–0.8, and genes expressed at low levels (>0.05% of the total cell protein) have a codon bias of 0.10–0.50 (Bennetzen and Hall, J. Biol. Chem., 257:3026–3031 (1982)). The calculated value for the codons of the human $\propto$-globin cDNA is 0.23. A similar value can be calculated for the β-globin cDNA. Because there is a very high correlation between the most commonly used codons, it is possible that hemoglobin expression from the human cDNA in yeast may be limited by the availability of the appropriate tRNA molecules. If this is so, a complete synthesis of the gene using the most highly favored yeast codons could improve the expression levels. It is quite possible that the greatest negative effect of adverse codon use would be if there was an abundance of codons used in the cDNA that are represented by low abundance tRNAs. In such a case, high level expression of hemoglobin could completely drain that pool of tRNA molecules, reducing translation not only of hemoglobin but of yeast proteins that happen to use that codon as well. In the case of the $\propto$-globin human cDNA, the most commonly used leucine codon is CTG (14 of 21), this codon is never used in highly expressed yeast genes (Guthrie and Abelson, *The Molecular Biology of the Yeast Saccharomyces,* Eds. Stratern, Jones and Broach, 1982. Cold Spring Harbor, N.Y.). The low codon bias index and the presence of rare yeast codons in the globin cDNAs have been sufficient incentive for us to synthesize a modified form of the alpha- and beta-globin genes using the preferred yeast codons.

Miscellaneous

The appended claims are hereby incorporated by reference as a further enumeration of the preferred embodiments. All cited references are incorporated by reference to the extent necessary to enable the practice of the invention as now or hereafter claimed.

Preparation of expression vectors suitable for use in production of the claimed multimeric hemoglobins may be facilitated by the Budapest Treaty deposit of the following vectors, all made with American Type Culture Collection, Rockville, Md. USA on May 10, 1990:

ATCC 68323 pDL III-14c

This is a derivative of pKK223-3 (Parmacia LKB, Piscataway, N.J., UDA) and pGEM1 (PromeguCorp., Madison, Wis., USA) which carries synthetic genes for des-Val alpha globin and des-Val beta globin as part of a polycistronic operon driven by a single Tac promoter.

ATCC 68324 pDL IV-8a

This is a derivative of PDL III-14c which contains a fused gene encoding an alpha globin moiety, a glycine, and a second alpha globin moiety, as well as a second gene encoding des-Val beta globin.

ATCC 20992 pGS 389

This is a yeast vector which expresses alpha and beta globin under control of GALGAP promoters.

The deposit of these vectors should not be construed as a license to make, use or sell them.

EXAMPLE 1

Construction of di-α globin mono-cysteine (A71C, D75C, or S81C) mutant expression vector The following plasmids, whose preparation is fully described in Hoffman, et al., WO88/09179, were manipulated in this Example.

Plasmid pDL II-83a

A gene encoding a Met initiation codon, a Factor X site (Ile-Glu-Gly-Arg)(SEQ ID NO:11), and human alpha globin, collectively referred to as FX-A, was synthesized and cloned into the XmaI/PstI sites of M13mp19. The EcoRI-PstI fragment bearing the FX-A gene was excised and recloned into pKK 223-3, placing it under control of the Tac promoter. This derivative was called pDLII-62m. The FX-A gene was removed from pDLII-62m and ligated with EcoRI/PstI linearized pGEM1, forming pGEM-FX-A. This was digested with NdeI and EaqI, removing the Factor Xa coding sequence (and part of the α globin coding sequence). The excised fragment was replaced by a synthetic oligonucleotide which restored the missing α globin codons; the resulting plasmid was named pDLII-83a. The protein expressed was "Met-Val-Leu- . . . ."

Plasmid pDLII-91f, in which the gene encodes "Met Leu . . . " instead of "Met-Val-Leu", was likewise constructed from pGEM-FX-A, but with a different synthetic replacement oligonucleotide, missing the Val codon.

Plasmid pSGE 1.1 E4

Figure 1:
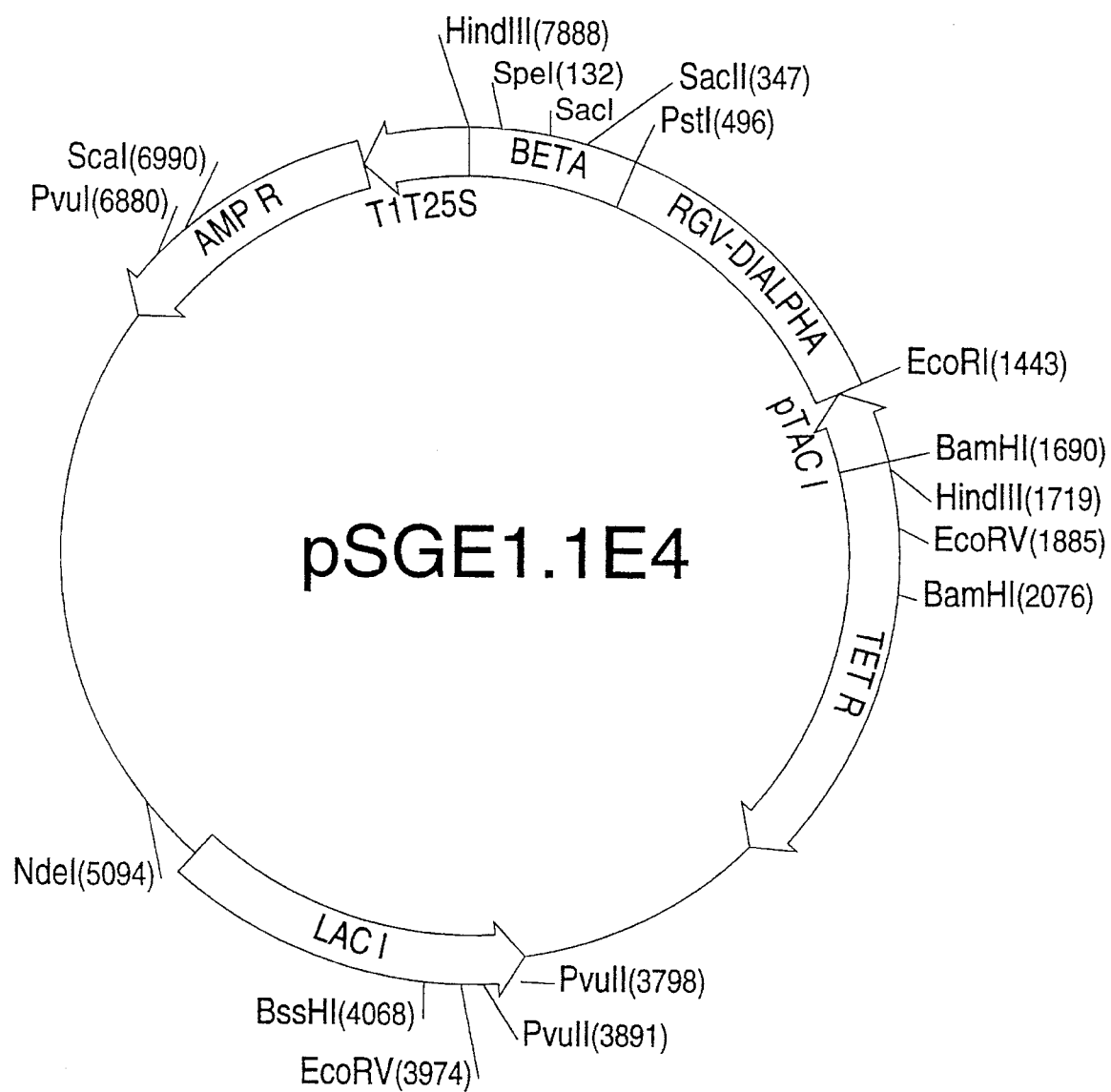
FIG. 1 Plamid pSGE1.1E4. This plasmid bears a polycistronic operon which comprises the pTAC promoter and genes encoding a di-alpha globin and a beta globin. It also carries tetracycline and ampicillin resistance genes, and the lacI gene.

This plasmid (also known as SGE1.1) is depicted in FIG. 1. Plasmid pDLIV-8A may be converted to SGE1.1E4 by the following protocol.

The expression plasmid pDLIV-8a contains the dialpha coding sequences, in which the alpha globins are linked by a single glycine codon, and the des-val beta globin genes, under the control of a single Ptac promoter. The plasmid encodes ampicillin resistance, does not have a functional tetracycline resistance gene, and is Rop+ and Lac. Oligonucleotide directed site specific mutagenesis using a commercially available kit such as DoubleTake™ (Stratagene, Inc.) can be used to insert the Presbyterian mutation into the beta globin sequence.

| AAC | | AAA |
|---|---|---|
| TTG | →→ | TTT |
| asn[108] | | lys |

The final expression plasmid, SGE 1.1E4 (amp R, tet R, Rop–, Lac+) is then constructed by insertion of both a functional tetracycline resistance gene and the lacI gene which encodes the lac repressor protein that inhibits the Ptac promoter until induction with an inducing agent. These modifications are described below.

The initial modification to the plasmid is the insertion of the lacI gene. This gene can be synthesized by polymerase chain reaction (PCR) amplification, according to the manufacturer's protocol (Perkin Elmer Cetus, Norwalk, Conn.) using the F episome of *E. coli* strain JM109 (FtraD36, proAB, lacIπΔM15)as a substrate. The following oligonucleotides can be used as primers:

Forward:

5' GCGGCCGCGGAAGAGTCAATTCAGGAGGGTG 3' (SEQ ID NO:12)

Reverse:

5' GCGGCCGTCACTGCCCGCTTTCCAGTCGGGAA 3' (SEQ ID NO:13)

The primers contain, at their 5' ends, sequences which encode for NotI restriction enzyme sites. The product of the PCR amplification reaction can be blunt ended and cloned into the PuvII site of the expression plasmid. The PuvII site is not reconstructed during this cloning step, so digestion with PuvII following ligation will linearize plasmids which do not incorporate the lacI sequence. Linearized plasmids will not transform *E. coli*. Because the primers are complementary only to the translated portion of the lacI gene, this fragment does not contain its own promoter. Note that inducibility or expression of hemoglobin is dependent on the orientation of the lacI gene, thus orientation should be checked after insertion of the lacI gene. The correct orientation has a smaller EcoR5 fragment than the incorrect orientation. Moreover, insertion of the lacI repressor gene into the PuvII restriction site inactivates the rop gene product and results in increased plasmid copy number.

The final modification to the plasmid is restoration of a functional tetracycline resistance gene. This can be accomplished by digestion of commercially available pBR322 with EcoRI followed by insertion via ligation of a synthetic DNA linker containing the 5' and 3' ends complementary to the EcoRI overhangs and na internal BamHI site. The BamHI fragment from this modified pBR322 vector containing the 5' coding sequence of the tetracycline resistance gene is purified by agarose gel electrophoresis, then inserted into the BamHI site of the modified pDL IV-8a plasmid. Only one orientation of the tet[R] fragment results in tetracycline resistance; strains can be screened for the proper orientation by growth on the appropriate medium. Insertion of the ter[R] fragment into the modified vector restores tetracycline resistance and produces SGE1.1E4.

Plasmid pGEM di-alpha.

The di-alpha gene-bearing SmaI/PstI fragment of SGE 1.1 E4 was ligated with SmaI/PstI-cut pGEM 1 to form pGEM di-alpha.

1.1 Subcloning of the α gene into phagescript

The desfxα pGem (pDLII-83a) vector was cut with EcoR1 and Pst1 endonucleases and ligated into EcoR1/Pst1 digested phagescript (obtained from Stratagene). *E. coli* strain DH5α was transformed with the ligation mixture and cells were plated on 2xYT plates overlaid with 3 ml top agar containing 10 μl 100 mM IPTG, 25 μl 2% X-Gal in DMSO and 150 μl XL-1 cells (Stratagene). Clear plaques were picked and grown at 37° C. in 2xYT containing XL-1 cells. Double stranded DNA was isolated from the cultures and checked for the presence of the 500 bp α gene by restriction analysis and agarose gel electrophoresis. Single stranded DNA was isolated from one of the desfxα phagescript transformants (named f191). The single stranded DNA was sequenced to confirm the presence of the desfxα gene in the phagescript.

1.2 Mutagenic oligonucleotides

Three mutagenic oligonucleotides were used in three separate mutagenic reactions. The sequences of the oligonucleotides were as follows (mutant codon is underlined):

Nigeria mutation: αS81C

5' CCG AAC GCG TTG TGC GCT CTG TCT GAT 3' [SEQ ID

NO:14]

αD75C

5' GGT GCT CAC GTT GAT TGC ATG CCG AAC GCG 3'
[SEQ ID NO:15]

αA71C]

5' CTG ACC AAC GCT GTT TGC CAC GTT GAT GAT 3' [SEQ ID NO:16]

1.3 Kinase reaction Conditions for mutagenic oligonucleotides A71C, D75C and S81C.

1 μl oligonucleotide (approx. 300 pmol)

2 μl 10× kinase buffer containing 10 mM ATP 0.5 μl T4 polynucleotide kinase (10 U/μl, New England Biolabs)

15.5 μl H$_2$O

1 μl 10 mM spermidine

Reactions were incubated for 1 hr. at 37° C., then 80 μl H$_2$O was added and the reaction was terminated by heat inactivation at 65° C. for 10 min.

1.4 Mutagenesis Reaction

1 μl fw 191 ss DNA (0.5 pmol)

3 μl kinased oligonucleotide (either A71C, D75C or S81C approx. 45 pmol)

2 μl 10× annealing buffer (Promega)

14 μl H$_2$O

The no primer control contained:

1 μl fw 191 ss DNA

2 μl 10× annealing buffer

17 μl H$_2$O

Reactions were heated to 65° C., cooled slowly to 35° C. (approx. 70 min), and put on ice for 5 min. The following reagents were added and the reactions were incubated at 37° C. for 90 min.

3 μl 10× synthesis buffer (Promega)

1 μl T4 gene 32 protein (0.5 μg/μl, Biorad)

1 μl T4 DNA polymerase (3 U/μl, NEB)

0.5 μl T4 DNA ligase (10 U/μl, NEB)

5 μl H$_2$O

200 μl 71–18 mut S competent cells (made according to Promega Altered Sites procedure) were transformed with 10 μl of each mutagenesis reaction, put on ice for 30 min and heat shocked for 2 min at 42° C. The transformation mixture was added to 3 ml 2xYT media and grown at 37° C. (with shaking) for 5.5 hr. After incubation, 1 ml of each of the three cultures was removed, centrifuged and 800 μl was stored in a fresh tube at 4° C. as the stock solution of mutant phage.

1.5 Screening for mutants of D75C

100 μl of a 10$^{-5}$ dilution of the D75C mutant phage stock was plated on 153 mm 2xYT plates overlain with top agar containing 0.5 ml XL-1 cells. Plates were incubated at 37° C. for approx. 5 hrs. Duplicate nitrocellulose filters were lifted off each plate and the plaques were lysed in 6 ml 0.5 M NaOH/1.5 M NaCl, neutralized in 10 ml 1 M Tris-HCl pH 8.0/1.5 M NaCl and washed in 500 ml 6xSSC. The filters were air dried and baked at 75° C. for 45 min. The filters were then boiled briefly in 1% SDS prior to prehybridization. Filters were prehybridized in 20 ml solution for 4 hr at 68° C. The prehybridization solution was as follows:

5xSSC (20x SSC prepared according to recipe in Maniatis).

–0.1% (w/v) N-lauroylsarcosine 0.02% (w/v) SDS 0.5% blocking reagent (Genius Kit, Boehringer Mannheim)

The D75C oligonucleotide was labelled with $\pi^{[32]}$ ATP as follows:

1 μl oligonucleotide (80 pmol)

10 μl 10× kinase buffer

1 μl $\pi^{[32]}$P ATP (10 μC/μl. Specific activity>3000 Ci/mmol).

87 μl H$_2$O

1 μl kinase (10 U/μl, NEB)

The reaction was incubated for 5 hrs. at 37° C. Unincorporated ATP was removed by centrifugation through a Biospin 30 column (Biorad). The entire probe (17,000 cpm/μl) was added to the prehybridization mixture and the filters were hybridized overnight at 46° C. along with a no primer control filter. The following day, filters were washed for 10 min. at room temperature (RT) in 6xSSC and exposed overnight at –70° C. on Kodak X-Omat film. Filters were washed in 6xSSC at 57° C. for 10 min, dried and exposed overnight, then washed in 6xSSC/0.1% SDS at 67° C. for 10 min, and dried and re-exposed overnight. The final was was in 6xSSC/0.1% SDS at 70° C. for 10 min and the filters were again dried and exposed overnight.

Ten plaques were picked which hybridized differentially to the mutant oligonucleotide (compared to the no primer control plaques). The plaques were placed in 5 ml 2xYT media containing 0.25 ml XL-1 cells. The cultures were incubated with shaking at 37° C. for 7.5 hr. 1 ml of each culture was removed, centrifuged 5 min, placed in a fresh tube and stored at 4° C. for subsequent sequencing and plaque purification.

1.6 Screening for mutants of A71C and S81C

1 μl of a 10$^{-3}$ dilution of the A71C stock phage mutagenesis reaction and 20 μl of a 10$^{-5}$ dilution of the S81C mutagenesis reaction were plated on four separate 82 mm 2xYT/tet(10 mg/ml) plates overlaid with 3 ml top agar and 100 μl XL-1 cells. A no primer control was also plated as above. The plates were incubated at 37° C. for 5 hr; plaques were lifted from each plate onto nitrocellulose filters and the filters dried overnight at room temperature. The following day, the plaques were lysed with 0.5 M NaOH/1.5 M NaCl for 3 min, neutralized in 1 M Tris-HCl pH 7.0/1.5 M NaCl for 3 min and washed in 6xSSC for 5 min. Filters were air dried then baked at 75° C. for 1 hr. The filters were boiled briefly in 1.5% SDS prior to prehybridization at 60° C. for 6 hr. in 10 ml prehybridization solution as described above.

1.7 Labelling of A71C and S81C oligonucleotides using digoxigenin (All reagents supplied by Boehringer Mannheim)

2 μl A71C (100 pmol) or 1 μl S81C (110 pmol)

10 μl terminal transferase buffer

5 μl 25 mM CoCl$_2$

1 μl 1 mM dUTP-digoxigenin

30 μl 04 31 μl H$_2$O (A71C and S81C reactions respectively)

1 μl terminal transferase (25 U/μl)

Reactions were incubated at 37° C. for 3 hr. followed by 6 hr. at RT. Digoxigenin-labelled A71C and S81C probes (20 μl) were added to the appropriate filters in 10 ml prehybridization solution along with a no primer control filter. The filters were hybridized overnight at 47° C.

1.8 Filter Washes and Development

All filters were initially washed in 6xSSC/0.1% SDS for 15 min at 30° C., then for 15 min at 42° C. Each of the four filters which had been probed with either the labelled A71C or S81C oligonucleotides were then separated and washed at increasingly higher temperatures along with a no primer control filter. One each of the A71C and S81C filters were placed in plastic bags containing 10 ml of 6×SSC/0.1% SDS and washed for 10 min at one of four temperatures, i.e., 50° C., 60° C. or 65° C. After the high temperature washes, each set of filters were developed according to the Genius Kit protocol.

Initially, bags containing the filters were filled with 10 ml of 100 mM Tris-HCl, pH 7.5/150 mM NaCl (buffer A) and incubated for 15 min. The buffer was removed and replaced with 10 ml buffer A containing 0.5% blocking reagent and incubated a further 15 min at RT without shaking. Anti-digoxigenin antibody (2 μl) was added directly to each bag and incubated with for 30 min at RT. The filters were then removed from their respective bags and washed altogether in 100 ml buffer A/0.05% blocking reagent for 15 min at RT, followed by a 15 min wash in buffer A alone at RT. The final wash was 100 ml 100 mM Tris-HCl, pH 9.5/100 mM NaCl/50 mM $MgCl_2$ (buffer B) for 5 min at RT. Each set of filters from a given temperature was placed in a separate bag along with 5 ml of color development solution (5 ml buffer B containing 22.5 μl 75 mg/ml NBT/15 μl 50 mg/ml X-phosphate). The filters were incubated for 30 min in the dark at RT. After 30 min, the filters were removed from the development solution, washed for 5 min in 100 ml 10×TE and 5 min in 100 ml 1× TE, both at RT. Filters were dried at RT.

Using the results from the Genius Kit screening procedure, 10 plaques which differentially hybridized to the labelled oligonucleotides A71C or S81C were picked and placed in 3 ml 2×YT media containing 0.25 ml XL-1 cells and incubated for 7.5 hr. at 37° C. with shaking. 1 ml of each culture was removed, centrifuged 5 min, placed in a fresh tube and stored at 4° C. for subsequent sequencing and plaque purification.

1.9 Confirmation of mutations by sequencing

Single stranded DNA was isolated from 800 μl mutant phage stock supernatant and sequenced using the Sequenase kit (USB) with the ∝ 179 oligonucleotide as the primer. The ∝ 179 aligonucleotide is an 18-mer hemolog cys to a region about 100 bps upstream of the mutation site.) Sequencing confirmed the presence of the ∝A71C, ∝D75C and ∝ S81C mutations.

Phage stock was plaque purified by plating 10 μl of −8 and $10^{-10}$ dilutions on 2×YT/tet (10 mg/ml) plates overlaid with 3 ml top agar containing 200 μl XL-1 cells. After 7 hrs incubation at 37° C., a single isolated plaque from each mutant plate was picked and used to inoculate 90 ml 2×YT/tet (10 mg/ml) media containing 10 ml XL-1 cells. Cultures were grown overnight at 37° C. with shaking. 1 ml of each mutant phage culture was removed, centrifuged and the supernatant was frozen at −80° C. as the respective purified mutant phage stock. Double stranded DNA was prepared from the remaining culture for use in the subsequent subcloning steps into the final expression vector 1.1E4.

1.10 Subcloning of the ∝ cys mutants into 1.1E4

Construction of the di-∝ gene with each of the three cysteine mutations in either the N-terminal or C-terminal domain of the di-∝ protein required three subcloning steps:

1) Transfer of the cys mutant ∝ gene from phagescript as an Eagl-Pstl fragment into the Eagl-Pstl digested desval ∝ pGem vector (pDL II-91f). This step provided the mutant ∝ gene with the correct 5' terminus.

2) A mutant di-∝ gene with each of the cys mutations in the 3' ∝ gene was constructed by inserting the Eagl DNA fragment from di-∝ pGem (pGem di-alpha) into the Eag1 site of the relevant cys mutant desval ∝ pGem plasmid. The mutant di∝ gene with the cys mutation in the 5' gene was constructed by inserting the BstB1 DNA fragment from di∝ pGem into the BstB1 site of the cys mutant desval ∝ pGem plasmid.

3) Finally each of the mutant di∝ genes were cloned into the 1.1E4 expression vector as a Smal-Pstl fragment. Transformations into DH5∝ at each step in the subcloning procedure were carried out as described in the methods of subcloning of the β G83C mutation into 1.1E4 (see below). The presence of the relevant cys mutation in the correct ∝ gene was confirmed by sequencing at each stage in the subcloning procedure. Each of the di∝ cys mutants in 1.1E4 were transformed into *E. coli* strain 127, grown in TB complete media and induced with IPTG. Expression of the di∝ and β proteins was confirmed by SDS-PAGE and Western blot analysis.

EXAMPLE 2

Protocol for the Oxidation of Two SGE1.1 Mono-Cys's to Form a Pseudo-Octamer

The hemoglobin mutants of interest were expressed in *E. coli* grown in standard fermentation broth, after induction with IPTG. The cells were pelleted, resuspended in 3 mols of 40 mM Tris-base, 2 mM benzamidine/gm cell paste, lysed by two passes through a Microfluidizer™ (Microfluidics, Inc.). The lysate was centrifuged to remove cell debris, and the supernatant was collected. The tetrameric hemoglobin was purified from the supernatant using the methodology described in Mathews, et al. (Methods in Enzymology, in press). Briefly, the supernatant is diluted with 5 mM Tris, pH 7.0 until the conductivity reaches 200 μmhos. The solution is then passed through a flow-through bed of Q Sepharose equilibrated with 20 mM Tris, pH 7.0. The flow through is collected, the pH of the solution is brought up to 8.0 using concentrated NaOH, and then loaded onto a second Q Sepharose column equilibrated in 20 mM Tris, pH 8.0. The hemoglobin captured on the column is washed with 2 column volumes of 20 mM Tris, pH 8.0, and eluted with 20 mM Tris, pH 7.0. Fractions are collected and pooled on the basis of absorbance ratios ($A_{575}/A_{540}$>1.03). The solution is then buffer exchanged using a Minitan™ (Millipore Corp.) into 14 mM sodium phosphate, pH 8–8.5/150 mM approximately 100 mg/ml. Note that at this point in the purification, some of the mutant hemoglobin tetramers have already formed significant levels of octamer (>20%) by simple air oxidation of the cysteines engineered into the molecules. However, to drive oxidation of the remaining cysteine thiols to disulfides, the solution is incubated under air or oxygen for approximately 48 hours at 4° C.

After incubation, the octamers are separated from any unreacted monomer and any higher order polymers using Sepharcryl S-200 equilibrated in 14 mM sodium phosphate, pH 8–8.5/150 mM NaCl at a linear flow rate of 60 cm/hr. Fractions are collected and poolings are verified using an analytical grade Superose 12 column.

For those hemoglobin mutants where a cysteine replacement is located in close proximity to a negative charge, or for which disulfide formation is otherwise incomplete, the above procedure is preferably modified to enhance disulfide formation. After concentration to 50 mg/ml using the procedure described above, the hemoglobin solution is converted to carbon monoxy hemoglobin by gentle bubbling with CO. Five $Cu^{++}$/heme are added to the solution using 100 mM CuCl$_2$, and the hemoglobin is incubated for 5 minutes on ice, under CO. The reaction is quenched by the addition of a five-fold molar excess (with respect to copper) of Na-EDTA. The resulting octamers are then purified as above.

EXAMPLE 3

Hypothetical Protocol for the Construction of Hemoglobin Molecules Stabilized Against Dimer Formation By Fusion Across the Alpha 1- Beta 2 or Alpha 2- Beta 1 Dimer Interface Region The currently employed inter-dimer di-alpha fusion between the C terminus of one alpha subunit and the N terminus of the adjacent alpha subunit, represents a successful protein engineering approach to stabilizing hemoglobin against dimer formation. In this case, use was made of the fortunate juxtaposition of the two termini which originate from different dimers. One might also make a di-beta polypeptide, as has been described, or a hemoglobin with both di-alpha and di-beta polypeptide, as has been described, or a hemoglobin with both di-alpha and di-beta linked subunits. Alternatively, one can envision other types of fusion in which the alpha subunit of one alpha/beta dimer is fused to the beta subunit of the other dimer (FIG. 6). In this, two individual, linked polypeptides would dimerize to form the psuedo-tetrameric hemoglobin. This approach is based on the fact that dimerization involves specific, identical pairs of subunits, generally referred to as $\propto 1\beta 1$ and $\propto 2\beta 2$.

As an example of this alternative fusion approach, the alpha subunit C terminal residue (Arg 141) of dimer 1 could be fused, either directly or with an intervening fusion sequence, to the N-terminal amino acid of the beta subunit C helix (Tyr 35) of dimer 2. This would create a new C terminal residue at the end of the beta B helix (Val 34) and would leave a "free" piece of polypeptide comprised of the beta A and B helices (residues 1 to 34 inclusive). These alterations would give rise to a protein comprised of alpha subunit helices A through H fused to beta subunit helices C through H. The polypeptide composed of the beta subunit A and B helices would be covalently attached to the protein by introducing a new helix into the molecule. The helix would be designed to span the distance between the beta C terminus (His 146) and the original beta N terminus of helix A (Val 1). Following these changes, the sequence of helices from the N to C terminus of the new protein would be (alpha) A-B-C-E-F'-F-G-H-(beta)-C-D-E-F'-F-G-H-NEW-A-B. The actual arrangement of the fusion regions would require careful design so that new regions of structure did not extend into the dimer-dimer interface region which is critical to cooperativity. Introduction of amino acids containing basic or acidic residues into the molecule at certain positions cold allow some restoration of functionally important salt bridges and hydrogen bonds which could be lost as a result of manipulating the normal N and C termini. The above approach could also extend to the production of the entire hemoglobin molecule or individual dimers as single polypeptide chains, although in the latter case this would not be expected to offer stabilization against dimer formation.

For the purpose of providing the potential for disulfide bond formation, a cysteine may be introduced into either the $\propto$ or $\beta$ globin domain of the $\propto_1\beta_2$ pseudodimer.

REFERENCE EXAMPLE A

Reconstitution of Recombinant Alpha-Globin and Recombinant Beta-Globin with Heme and Chemical Reduction to Yield Artificial Hemoglobin Conventional methods of preparing artificial hemoglobin are exemplified by the following procedure.

The lyophilized recombinant alpha and beta-globins (100 mg each) were individually dissolved in 8M urea/50 mM Tris- Cl, pH 8.01/1 mM EDTA/1 mM DTT, diluted to a concentration of 5 mg/ml and incubated at room temperature for 3–4 hours. The alpha-globin was then diluted to 0.3 mg/ml with chilled 20 mM K$_2$HPO$_4$, pH 5.7/1 mM EDTA/1 mM DTT. Hemin (25 mg) was dissolved in 2.4 mg 0.1M KOH, diluted with an equal volume of 1M KCN; this solution was then made 0.1 mg/ml in hemin and 20 mM K$_2$HPO$_4$, pH 6.7 with stock phosphate buffer. Hemin from this solution was added at a 2.8 molar excess to the chilled alpha-globin; and equal molar amount of beta-globin was added and the solution was dialyzed at 4° C. overnight against 0.1M K$_2$HPO$_4$, pH 7.6/1 mM EDTA/1 mM KCN. The artificial Hb solution was concentrated by ultra-filtration using a PM-10 membrane (Amicon) and transferred into a 200 ml screw-top test tube with a rubber septum. The hemoglobin solution was deoxygenated by evacuation and flushing with N$_2$, and then the solution was saturated with CO. 100 mM sodium dithionite solution was prepared anaerobically in a 20 ml screw-top test tube with rubber septum. 4.5 equivalents of dithionite were added to the Hb solution with a syringe, and the mixture incubated on ice for 15 min. The Hb solution was gel-filtered against 10 mM Na phosphate buffer pH 6.0 on a 4×40 cm Sephadex G-25 (fine) column. The colored solution was then applied to a 2×10 cm-52 (Whatman) column equilibrated with the same buffer and the chromatography was developed with a linear gradient of 500 ml 10 mM Na phosphate buffer pH 6.0 and 500 ml of 70 mM sodium phosphate buffer pH 6.9. CO was removed from Hb by photolysis under a stream of oxygen. Artificial Hgb prepared this way is isolated in only about 25% yield from the fusion peptides but shows native oxygen binding properties.

REFERENCE EXAMPLE B

P$_{50}$ Determination

Our preferred method of measuring P50 of purified hemoglobin solutions for the purpose of the appended claims is as follows:

Hemoglobin-oxygen equilibrium curves are measured using a Hemox Analyzer™ (TCS Medical Products, Southampton, Pa.) at either 25° C. or 37° C.+0.1° C. in 50 mM HEPES buffer/0.1 M NaCl, pH 7.4. Oxygen equilibrium curves are measured by N2 deoxygenation of an oxyhemoglobin solution that has been previously equilibrated with water-saturated O$_2$ (for samples iwth a P50>10 torr) or with water-saturated compressed air. Absorbance readings at 568 and 558 nm are measured throughout the run for determination of percent oxyhemoglobin in the sample. Precent oxyhemoglobin is directly proportional to log A$\neq$558/log A$\neq$568 and is independent of path length. Both the absorbances and the oxygen pressure are sampled by a programmable-gain 12-bit analog-to-digital converter (Labmaster PGH, Scientific Solutions, Solon, Ohio) under computer control. The oxygen equilibrium curve is subjected to a low-apss digital filter. P$_{50}$ values (partial pressure of O$_2$ required for 50% saturation of oxygen binding sites) and Hill coefficients ("max) are calculated from the digitally filtered data by using software developed in our laboratory. The Hill coefficients are determined as the maximum slope of the functions dlog[y/(1-y)]/dlog p, where y is % O$_2$ saturation and p is partial pressure of O$_2$.

P$_{50}$ may also be measured under other conditions, but it should be noted that many environmental factors affect hemoglobin's oxygen affinity. The effect of Ph, CO$_2$ inorganic unions, organic phosphates and temperature on P$_{50}$ are discussed in Bunn and Forget, HEMOGLOBIN: MOLECU- LAR, GENETIC AND CLINICAL ASPECTS 37–47, 95–98 (W. B. Saunders Co., 1986).

Since many determinations of whole blood oxygen binding curves are made under standard physiologic conditions (37° C., pH, 7.4, $PCO_2$ 40 mm Hg), it may be necessary to adjust literature figures. In this context, it should be noted that a 10° C. increase results in nearly a two-fold increase in $P_{50}$, while the dependence of $P_{50}$, while the dependence of $P_{50}$ on pH is approximately given as delta log $P_{50}$/delta pH=−0.5.

Comparing $P_{50}$ values of purified Hb preparations to $P_{50}$ values of whole blood can be problematic. Whole blood, or isolated RBC's contain many components that naturally modulate the shape of the hemoglobin-oxygen binding curve. The RBC encapsulates Hgb in the presence of a high concentration of the effector molecule 2.3-DPG; a molecule that causes Hgb to have a markedly lower affinity for $O_2$. Other intra-erythrocyte components also affect the shape of the binding curve: ATP, Cl- $CO_2$, H+, orthophosphate, methemoglobin and carboxyhemoglobin. The levels of these substances may vary with age, sex and condition. These substances are not normally present in purified HgB solutions and thus, the $P_{50}$ value of purified Hgb is lower than that found in whole blood. One very important modulator of Hgb-oxygen affinity is Cl- ion. Cl ion is found outside the erythrocyte in the blood serum at a physiologic concentration of approximately 0.15M. Since Cl- causes a lower $O_2$ affinity, a Hgb solution with a $P_{50}$ measured in vitro may well have much lower $O_2$ affinity if infused into the blood stream. Another problem with measuring $O_2$ binding of whole blood is that RBCs are quite fragile and in the process of manipulating the erythrocyte into the instrument used to measure the $O_2$ binding it is inevitable that at least a small percentage of the RBCs will lyse. Lysed RBCs leak Hgb into the surrounding media away from 2,3-DPG; hence, since free Hgb has a higher affinity than intraerythrocyte Hgb, lysed RBCs will have a higher $O_2$ affinity and can cause a falsely low P50 value for whole blood P50 determinations. It is widely accepted that under physiologic conditions while blood has a P50 value of 26–28 mm Hg. When Hgb is isolated from whole blood, however, the measured P50 is on the order of 1–10 mm Hg depending on the investigator's experimental conditions. For these reasons it is most accurate to measure Hgb-oxygen equilibria with purified Hgb molecules under strict conditions of buffer, pH and salt concentrations. Unfortunately, there are no accepted "standards" for all investigators to measure Hgb oxygen binding for in vitro systems.

Still, as many mutant hemoglobins are first identified in patient's whole blood, one would like to be able to compare the relative affinities of native and mutant Hgb for O2, between whole blood and purified Hgb preparations. An example of this is Hgb Chico (beta $lys^{66}$-thr). If one examined only the $P_{50}$ value of the purified mutant Hgb (10.1 mmHg) one would note that Hgb has a $P_{50}$ value less than that for normal whole blood (27.2 mmHg). Still, when that hemoglobin is measured in RBCs under physiologic conditions it is apparent that it does have a higher $P_{50}$ than normal whole blood (38 mmHg). One cannot predict the degree that the $P_{50}$ value will change going from whole blood Chico to a purified Hgb Chico if it were infused into the bloodstream as a blood substitute. One can conclude however, that the $P_{50}$ will be higher than it is in pure form, and that by reacting the mutant Hgb with organic phosphates that $P_{50}$ will be even higher.

TABLE 1

PRIMARY STRUCTURE OF HUMAN GLOBIN SUBUNITS

| Helix | α | Zeta | Helix* | β | δ | Gamma | ε |
|---|---|---|---|---|---|---|---|
| NA1 | 1 Val | Ser | NA1 | 1 Val | Val | Gly | Val |
|  |  |  | NA2 | 2 His | His | His | His |
| NA2 | 2 Leu | Leu | NA3 | 3 Leu | Leu | Phe | Phe |
| A1 | 3 Ser | Thr | A1 | 4 Thr | Thr | Thr | Thr |
| A2 | 4 Pro | Lys | A2 | 5 Pro | Pro | Glu | Ala |
| A3 | 5 Ala | Thr | A3 | 6 Glu | Glu | Glu | Glu |
| A4 | 6 Asp | Glu | A4 | 7 Glu | Glu | Asp | Glu |
| A5 | 7 Lys | Arg | A5 | 8 Lys | Lys | Lys | Lys |
| A6 | 8 Thr | Thr | A6 | 9 Ser | Thr | Ala | Ala |
| A7 | 9 Asn | Ile | A7 | 10 Ala | Ala | Thr | Ala |
| A8 | 10 Val | Ile | A8 | 11 Val | Val | Ile | Val |
| A9 | 11 Lys | Val | A9 | 12 Thr | Asn | Thr | Thr |
| A10 | 12 Ala | Ser | A10 | 13 Ala | Ala | Ser | Ser |
| A11 | 13 Ala | Met | A11 | 14 Leu | Leu | Leu | Leu |
| A12 | 14 Trp | Trp | A12 | 15 Trp | Trp | Trp | Trp |
| A13 | 15 Gly | Ala | A13 | 16 Gly | Gly | Gly | Ser |
| A14 | 16 Lys | Lys | A14 | 17 Lys | Lys | Lys | Lys |
| A15 | 17 Val | Ile | A15 | 18 Val | Val | Val | Met |
| A16 | 18 Gly | Ser |  |  |  |  |  |
| AB1 | 19 Ala | Thr |  |  |  |  |  |
| B1 | 20 His | Gln | B1 | 19 Asn | Asn | Asn | Asn |
| B2 | 21 Ala | Ala | B2 | 20 Val | Val | Val | Val |
| B3 | 22 Gly | Asp | B3 | 21 Asp | Asp | Glu | Glu |
| B4 | 23 Glu | Thr | B4 | 22 Glu | Ala | Asp | Glu |
| B5 | 24 Tyr | Ile | B5 | 23 Val | Val | Ala | Ala |
| B6 | 25 Gly | Gly | B6 | 24 Gly | Gly | Gly | Gly |
| B7 | 26 Ala | Thr | B7 | 25 Gly | Gly | Gly | Gly |
| B8 | 27 Glu | Glu | B0 | 26 Glu | Glu | Glu | Glu |
| B9 | 28 Ala | Thr | B9 | 27 Ala | Ala | Thr | Ala |
| B10 | 29 Leu | Leu | B10 | 28 Leu | Leu | Leu | Leu |
| B11 | 30 Glu | Glu | B11 | 29 Gly | Gly | Gly | Gly |
| B12 | 31 Arg | Arg | B12 | 30 Arg | Arg | Arg | Arg |
| B13 | 32 Met | Leu | B13 | 31 Leu | Leu | Leu | Leu |
| B14 | 33 Phe | Phe | B14 | 32 Leu | Leu | Leu | Leu |
| B15 | 34 Leu | Leu | B15 | 33 Val | Val | Val | Val |

TABLE 1-continued

PRIMARY STRUCTURE OF HUMAN GLOBIN SUBUNITS

| Helix | α | Zeta | Helix* | β | δ | Gamma | ε |
|---|---|---|---|---|---|---|---|
| B16 | 35 Ser | Ser | B16 | 34 Val | Val | Val | Val |
| C1 | 36 Phe | His | C1 | 35 Tyr | Tyr | Tyr | Tyr |
| C2 | 37 Pro | Pro | C2 | 36 Pro | Pro | Pro | Pro |
| C3 | 38 Thr | Gln | C3 | 37 Trp | Trp | Trp | Trp |
| C4 | 39 Thr | Thr | C4 | 38 Thr | Thr | Thr | Thr |
| C5 | 40 Lys | Lys | C5 | 39 Gln | Gln | Gln | Gln |
| C6 | 41 Thr | Thr | C6 | 40 Arg | Arg | Arg | Arg |
| C7 | 42 Tyr | Tyr | C7 | 41 Phe | Phe | Ile | Phe |
| CE1 | 43 Phe | Phe | CD1 | 42 Phe | Phe | Phe | Phe |
| CE2 | 44 Pro | Pro | CD2 | 43 Glu | Glu | Asp | Asp |
| CE3 | 45 His | His | CD3 | 44 Ser | Ser | Ser | Ser |
| CE4 | 46 Phe | Phe | CD4 | 45 Phe | Phe | Phe | Phe |
|  |  |  | CD5 | 46 Gly | Gly | Gly | Gly |
| CE5 | 47 Asp | Asp | CD6 | 47 Asp | Asp | Asn | Asn |
| CE6 | 48 Leu | Leu | CD7 | 48 Leu | Leu | Leu | Leu |
| CE7 | 40 Ser | His | CD8 | 49 Ser | Ser | Ser | Ser |
| CE8 | 50 His | Pro | D1 | 50 Thr | Ser | Ser | Ser |
|  |  |  | D2 | 51 Pro | Pro | Ala | Pro |
|  |  |  | D3 | 52 Asp | Asp | Ser | Ser |
|  |  |  | D4 | 53 Ala | Ala | Ala | Ala |
|  |  |  | D5 | 54 Val | Val | Ile | Ile |
|  |  |  | D6 | 55 Met | Met | Met | Leu |
| CE9 | 51 Gly | Gly | D7 | 56 Gly | Gly | Gly | Gly |
| E1 | 52 Ser | Ser | E1 | 57 Asn | Asn | Asn | Asn |
| E2 | 53 Ala | Ala | E2 | 58 Pro | Pro | Pro | Pro |
| E3 | 54 Gln | Gln | E3 | 59 Lys | Lys | Lys | Lys |
| E4 | 55 Val | Leu | E4 | 60 Val | Val | Val | Val |
| E5 | 56 Lys | Arg | E5 | 61 Lys | Lys | Lys | Lys |
| E6 | 57 Gly | Ala | E6 | 62 Ala | Ala | Ala | Ala |
| E7 | 58 His | His | E7 | 63 His | His | His | His |
| E8 | 59 Gly | Gly | E8 | 64 Gly | Gly | Gly | Gly |
| E9 | 60 Lys | Ser | E9 | 65 Lys | Lys | Lys | Lys |
| E10 | 61 Lys | Lys | E10 | 66 Lys | Lys | Lys | Lys |
| E11 | 62 Val | Val | E11 | 67 Val | Val | Val | Val |
| E12 | 63 Ala | Val | E12 | 68 Leu | Leu | Leu | Leu |
| E13 | 64 Asp | Ala | E13 | 69 Gly | Gly | Thr | Thr |
| E14 | 65 Ala | Ala | E14 | 70 Ala | Ala | Ser | Ser |
| E15 | 66 Leu | Val | E15 | 71 Phe | Phe | Leu | Phe |
| E16 | 66 Thr | Gly | E16 | 72 Ser | Ser | Gly | Gly |
| E17 | 68 Asn | Asp | E17 | 73 Asp | Asp | Asp | Asp |
| E18 | 69 Ala | Ala | E18 | 74 Gly | Gly | Ala | Ala |
| E19 | 70 Val | Val | E19 | 75 Leu | Leu | Ile, Thr | Ile |
| E20 | 71 Ala | Lys | E20 | 76 Ala | Ala | Lys | Lys |
| EF1 | 72 His | Ser | EF1 | 77 His | His | His | Asn |
| EF2 | 73 Val | Ile | EF2 | 78 Leu | Leu | Leu | Met |
| EF3 | 74 Asp | Asp | EF3 | 79 Asp | Asp | Asp | Asp |
| EF4 | 75 Asp | Asp | EF4 | 80 Asn | Asn | Asp | Asn |
| EF5 | 76 Met | Ile | EF5 | 81 Leu | Leu | Leu | Leu |
| EF6 | 77 Pro | Gly | EF6 | 82 Lys | Lys | Lys | Lys |
| EF7 | 78 Asn | Gly | EF7 | 83 Gly | Gly | Gly | Pro |
| EF8 | 79 Ala | Ala | EF8 | 84 Thr | Thr | Thr | Ala |
| F1 | 80 Leu | Leu | F1 | 85 Phe | Phe | Phe | Phe |
| F2 | 81 Ser | Ser | F2 | 86 Ala | Ser | Ala | Ala |
| F3 | 82 Ala | Lys | F3 | 87 Thr | Gln | Gln | Lys |
| F4 | 83 Leu | Leu | F4 | 88 Leu | Leu | Leu | Leu |
| F5 | 84 Ser | Ser | F5 | 89 Ser | Ser | Ser | Ser |
| F6 | 85 Asp | Glu | F6 | 90 Glu | Glu | Glu | Glu |
| F7 | 86 Leu | Leu | F7 | 91 Leu | Leu | Leu | Leu |
| F8 | 87 His | His | F8 | 92 His | His | His | His |
| F9 | 88 Ala | Ala | F9 | 93 Cys | Cys | Cys | Cys |
| FG1 | 89 His | Tyr | FG1 | 94 Asp | Asp | Asp | Asp |
| FG2 | 90 Lys | Ile | FG2 | 95 Lys | Lys | Lys | Lys |
| FG3 | 91 Leu | Leu | FG3 | 96 Leu | Leu | Leu | Leu |
| FG4 | 92 Arg | Arg | FG4 | 97 His | His | His | His |
| FG5 | 93 Val | Val | FG5 | 98 Val | Val | Val |  |
| G1 | 94 Asp | Asp | G1 | 99 Asp | Asp | Asp | Asp |
| G2 | 95 Pro | Pro | G2 | 100 Pro | Pro | Pro | Pro |
| G3 | 96 Val | Val | G3 | 101 Glu | Glu | Glu | Glu |
| G4 | 97 Asn | Asn | G4 | 102 Asn | Asn | Asn | Asn |
| G5 | 98 Phe | Phe | G5 | 103 Phe | Phe | Phe | Phe |
| G6 | 99 Lys | Lys | G6 | 104 Arg | Arg | Lys | Lys |
| G7 | 100 Leu | Leu | G7 | 105 Leu | Leu | Leu | Leu |
| G8 | 101 Leu | Leu | G8 | 106 Leu | Leu | Leu | Leu |
| G9 | 102 Ser | Ser | G9 | 107 Gly | Gly | Gly | Gly |
| G10 | 103 His | His | G10 | 108 Asn | Asn | Asn | Asn |

TABLE 1-continued

PRIMARY STRUCTURE OF HUMAN GLOBIN SUBUNITS

| Helix | α | Zeta | Helix* | β | δ | Gamma | ε |
|---|---|---|---|---|---|---|---|
| G11 | 104 Cys | Cys | G11 | 109 Val | Val | Val | Val |
| G12 | 105 Leu | Leu | G12 | 110 Leu | Leu | Leu | Met |
| G13 | 106 Leu | Leu | G13 | 111 Val | Val | Val | Val |
| G14 | 107 Val | Val | G14 | 112 Cys | Cys | Thr | Ile |
| G15 | 198 Thr | Thr | G15 | 113 Val | Val | Val | Ile |
| G16 | 109 Leu | Leu | G16 | 114 Leu | Leu | Leu | Leu |
| G17 | 110 Ala | Ala | G17 | 115 Ala | Ala | Ala | Ala |
| G18 | 111 Ala | Ala | G18 | 116 His | Arg | Ile | Thr |
| G19 | 112 His | Arg | G19 | 117 His | Asn | His | His |
| GH1 | 113 Leu | Phe | GH1 | 118 Phe | Phe | Phe | Phe |
| GH2 | 114 Pro | Pro | GH2 | 119 Gly | Gly | Gly | Gly |
| GH3 | 115 Ala | Ala | GH3 | 120 Lys | Lys | Lys | Lys |
| GH4 | 116 Glu | Asp | GH4 | 121 Glu | Glu | Glu | Glu |
| GH5 | 117 Phe | Phe | GH5 | 122 Phe | Phe | Phe | Phe |
| H1 | 118 Thr | Thr | H1 | 123 Thr | Thr | Thr | Thr |
| H2 | 119 Pro | Ala | H2 | 124 Pro | Pro | Pro | Pro |
| H3 | 120 Ala | Glu | H3 | 125 Pro | Gln | Glu | Glu |
| H4 | 121 Val | Ala | H4 | 126 Val | Met | Val | Val |
| H5 | 122 His | His | H5 | 127 Gln | Gln | Gln | Gln |
| H6 | 123 Ala | Ala | H6 | 128 Ala | Ala | Ala | Ala |
| H7 | 124 Ser | Ala | H7 | 129 Ala | Ala | Ser | Ala |
| H8 | 125 Leu | Trp | H8 | 130 Tyr | Tyr | Trp | Trp |
| H9 | 126 Asp | Asp | H10 | 131 Gln | Gln | Gln | Gln |
| 10 | 127 Lys | Lys | H10 | 132 Lys | Lys | Lys | Lys |
| H11 | 128 Phe | Phe | H11 | 133 Val | Val | Met | Leu |
| H12 | 129 Leu | Leu | H12 | 134 Val | Val | Val | Val |
| H13 | 130 Ala | Ser | H13 | 135 Ala | Ala | Thr | Ser |
| H14 | 131 Ser | Val | H14 | 136 Gly | Gly | Gly, Ala | Ala |
| H15 | 132 Val | Val | H15 | 137 Val | Val | Val | Val |
| H16 | 133 Ser | Ser | H16 | 138 Ala | Ala | Ala | Ala |
| H17 | 134 Thr | Ser | H17 | 139 Asn | Asn | Ser | Ile |
| H18 | 135 Val | Val | H18 | 140 Ala | Ala | Ala | Ala |
| H19 | 136 Leu | Leu | H19 | 141 Leu | Leu | Leu | Leu |
| H20 | 137 Thr | Thr | H20 | 142 Ala | Ala | Ser | Ala |
| H21 | 138 Ser | Glu | H21 | 143 His | His | Ser | His |
| HC1 | 139 Lys | Lys | HC1 | 144 Lys | Lys | Arg | Lys |
| HC2 | 140 Tyr | Tyr | HC2 | 145 Tyr | Tyr | Tyr | Tyr |
| HC3 | 141 Arg | Arg | HC3 | 146 His | His | His | His |
| | -(SEQ ID NO:17) | (SEQ ID NO:18) | | (SEQ ID NO:19) | | (SEQ ID NO:20) | |
| | | (SEQ ID NO:21–23) | | (SEQ ID NO:24) | | | |

TABLE 2

NATURAL LOW AFFINITY HEMOGLOBIN MUTANTS

| | | $P_{50}$* | | | |
|---|---|---|---|---|---|
| Hemoglobin | Alpha Mutant | RBC-Free Hgb | Whole Blood (nl) | Area of Mutant | Reference |
| Hirosaki | 43 (CD1) | phe—>leu | n/a | | heme | 1, 2 |
| Torino | 43 (CD1) | phe—>val | n/a | | heme | 1, 3 |
| Moabit | 86 (F7) | leu—>arg | | 30.6 (26.4–29.2) | heme | 4 |
| Titusville | 94 (G1) | asp—>asn | 15.8 (4.7) | | $\alpha_1\beta_2$ | 5 |

| | | $P_{50}$ (mmHg) | | | |
|---|---|---|---|---|---|
| Hemoglobin | Beta Mutant | Hgb (nl) | Whole Blood (nl) | Area of Mutant | Reference |
| Raleigh | 1 val—>acetyl ala | 4.0 (2.2) | | DPG site | 6 |
| Connecticut | 21 (B3) asp—>gly | 5.0 (2.2) | | B-E helices | 7 |
| Moscva | 24 (B6) gly—>asp | 14.8 (12.6) | | B-E helices | 8 |
| Rothschild | 37 (C3) trp—>arg | 3.5 (2.0) | | $\alpha_1\beta_2$ | 9 |
| Hazebrouck | 38 (C4) thr—>pro | | 36 (27–29) | $\alpha_1\beta_2$ | 10 |
| Hammersmith | 42 (CD1) phe—>ser | n/a | | heme/$\alpha_1\beta_2$ | 1, 11 |
| Louisville | 42 (CD1) phe—>leu | 24 (21) | | heme/$\alpha_1\beta_2$ | 12, 13 |
| Sendagi | 42 (CD1) phe—>val | 3.75 (3.05) | | heme/$\alpha_1\beta_2$ | 14 |
| Cheverley | 45 (CD4) phe—>ser | | 38.7 (28.7) | heme | 15 |
| Okaloosa | 48 (CD7) leu—>arg | 0.95 (0.7) | 30 (26) | C-D helices | 16 |
| Bologna | 61 (E5) lys—>met | | 37.6 (27.0) | B-E helices | 17 |
| Cairo | 65 (E9) lys—>gln | | 41 (31) | heme | 18 |
| Chico | 66 (E10) lys—>thr | 10.1 (5.0) | 38.0 (27.2) | heme | 19 |
| Bristol | 67 (E11) val—>asp | | 25.0 (19.0) | heme | 20 |
| Seattle | 70 (E14) ala—>asp | | 43.5 (28.1) | heme | 21, 22 |

TABLE 2-continued

NATURAL LOW AFFINITY HEMOGLOBIN MUTANTS

| Name | Position | Mutation | P50 | | Site | Ref |
|---|---|---|---|---|---|---|
| Vancouver | 73 (E17) | asp—>tyr | n/a | | | 1, 23 |
| Korle-Bu | 73 (E17) | asp—>asn | n/a | | | 1, 24 |
| Mobile | 73 (E17) | asp—>val | n/a | | | |
| Rahere | 82 (EF6) | lys—>thr | 15.5 (11.0) | | DPG site | 26 |
| Pyrgos | 83 (EF7) | gly—>asp | | | External | 27 |
| Roseau-Pointe | 90 (F6) | glu—>gly | | 38 (28) | $\alpha_1\beta_2$ | 28 |
| Agenogi | 90 (F6) | glu—>lys | 9.0 (6.8) | | $\alpha_1\beta_2$ | 29 |
| Caribbean | 91 (F7) | leu—>arg | 28.0 (21.0) | | heme | 30 |
| Kansas | 102 (G4) | asn—>thr | 28.0 (9.0) | | $\alpha_1\beta_2$ | 31 |
| Beth Israel | 102 (G4) | asn—>ser | | 88.0 (26.0) | $\alpha_1\beta_2$ | 32 |
| Saint Mande | 102 (G4) | asn—>tyr | | 52 (28) | $\alpha_1\beta_2$ | 33 |
| Richmond | 102 (G4) | asn—>lys | n/a | | $\alpha_1\beta_2$ | 1, 34 |
| Burke | 107 (G9) | gly—>arg | 9.3 (7.7) | | heme | 35 |
| Yoshizuka | 108 (G10) | asn—>asp | 12.9 (9.0) | | $\alpha_1\beta_2$ | 36 |
| Presbyterian | 108 (G10) | asn—>lys | 6.3 (2.5) | | $\alpha_1\beta_2$ | 37 |
| Peterborough | 111 (G13) | val—>phe | 14.0 (9.0) | | $\alpha_1\beta_2$ | 38 |
| New York | 113 (G15) | val—>glu | n/a | | G-helix | 1, 39 |
| Hope | 136 (H14) | gly—>asp | n/a | | heme | 1, 40 |
| Himeji | 140 (H18) | ala—>asp | 5.8 (4.5) | | | |

*Parenthetical values are that investigator's measured $P_{50}$ for conventional Hgb A in RBC-free or RBC-bound state, as indicated References for Table 2

1) Wrightstone, R. N. *Hemoglobin* 1987 11, 241–308.
2) Ohba, Y.; Miyaji, T.; Matsuoka, M.; Yokoyama, M.; Numakura, H.; Nagata, K.; Takebe, Y.; Izumu, Y.; Shibata, S. *Biochemi. Biophys. Acta* 1975, 405, 155–160.
3) Beretta, A.; Prato, V.; Gallo, E.; Lehmann, H. *Nature* 1968, 217, 1016–1018.
4) Knuth, A.; Pribilla, W.; Marti, H. R.; Winterhalter, K. H. *Acta Haematol* 1979, 61, 121–124.
5) Schneider, R. G.; Arkins, R. J.; Hosty, T. S.; Tomlin, G.; Casey, R.; Lehmann, H.; Lorkin, P. A.; Nagei, K. *Biochem Biophys. Acta* 1975, 400, 365–373.
6) Moo-Penn, W. F.; Bechtel, K. C.; Schmidt, R. M.; Johnson, M. H.; Jue, D. L.; Schmidt, D. E.; Dunlap, W. M.; Opella, S. J.; Boneventura, J.; Boneventura, C. *Biochemistry* 1977, 16, 4872–4879.
7) Moo-Penn, W. F.; McPhedran, P.; Bobrow, S.; Johnson, M. H.; Jue, D. L.; Olsen, K. W. *Amer. J. Hematol* 1981, 11, 137–145.
8) Idelson, L. I.; Didkowsky, N. A.; Casey, R.; Lorkin, P. A.; Lehmann, H. *Nature* 1974, 249, 768–770.
9) Gacon, G.; Belkhodja, O.; Wajcman, H.; Labie, D. *Febs Lett* 1977, 82, 243–246.
10) Blouquit.; Delanoe, -Garin, J.; Lacombe, C.; Arous, N.; Cayre, Y.; Peduzzi, J.; Braconnier, F.; Galacteros, F.; *Febs Lett.* 1984, 172, 155–158.
11) Dacie, J. V.; Shinton, N. K.; Gaffney, P. J.; Carrell, R. W.; Lehmann, H. *Nature* 1967, 216, 663–665.
12) Keeling, M. M.; Ogden, L. L.; Wrightstone, R. N.; Wilson, J. B.; Reynolds, C. A.; Kitchens, J. L.; Huisman, T. H. *J. Clin. Invest.* 1971, 50, 2395–2402.
13) Bratu, V.; Larkin, P. A.; Lehmann, H.; Predescu, C. *Biochem. Biophys. Acta.* 1971, 251, 1–6.
14) Ogata, K.; Ho, T.; Okazaki, T.; Dan, K.; Nomura, T.; Nozawa, Y.; Kajita, A. *Hemoglobin* 1986, 10, 469–481.
15) Yeager, A. M.; Zinkham, W. H.; Jue, D. L.; Winslow, R. M.; Johnson, M. H.; McGuffey, J. E.; Moo-Penn, W. F. *Ped. Res.* 1983, 17, 503–507.
16) Charache, S.; Brimhall, B.; Milner, P.; Cobb, L. *J. Clin. Invest.* 1973, 52, 2858–2864.
17) Marinucci, M.; Giuliani, A.; Maffi, D.; Massa, A.; Giampolo, A.; Mavilio, F.; Zannotti, M.; Tantori, L. *Biochem. Biophys. Acta.* 1981, 668, 209–215.
18) Garel, M. C.; Hasson, W.; Coquelet, M. T.; Goosens, M.; Rosa, J.; Arous, N. *Biochem. Biophys. Acta.* 1976, 420, 97–104.
19) Shih, D. T.; Jones, R. T.; Shih, M. F. C.; Jones, M. B.; Koler, R. D.; *Hemoglobin* 1987, 11, 453–464.
20) Steadman, J. H.; Yates, A.; Huehns, E. R.; Brit., *J. Haematol* 1970, 18, 435–446.
21) Stamatoyannopoulos, G.; Parer, J. T.; Finch, C. *New Eng. J. Med.* 1969, 281, 915–919.
22) Anderson, N. L.; Perutz, M. F.; Stamatoyannopoulos, G. *Nature New Biol.* 1973, 243, 275–276.
23) Jones, R. T.; Brimhall, B.; Pootrakul, S.; Gray, G. *J. Mol. Evol.* 1976, 9, 37–44.
24) Konotey-Ahulu, F. I. D.; Gallo, E.; Lehmann, H.; Ringelhann, B. *J. Med. Genet.* 1968, 5, 107–111.
25) Schneider, R. G.; Hosty, T. S.; Tomlin, G.; Atkins, R.; Brimhall, B.; Jones, R. T. *Biochem Genet.* 1975, 13, 411–415.
26) Sugihara, J.; Imamura, T.; Nagafuchi, S.; Boneventura, J.; Boneventura, C.; Cashon, R. *J. Clin. Invest.* 1985, 76, 1169–1173.
27) Tatsis, B.; Sofroniadou, K.; Stergiopoulas, C. I. *Blood* 1976, 47, 827–832.
28) Merault, G.; Keclard, L.; Saint-Martin, C.; Jasmin, K.; Campier, A.; Delanoe Garin, J.; Arous, N.; Fortune, R.; Theodore, M.; Seytor, S.; Rosa, J.; Blouquit, Y.; Galacteros, F. *Febs Lett.* 1985, 184, 10–13.
29) Inai, K.; Morimoto, H.; Kotani, M.; Shibata, S.; Miyaji, T.l Matsutomo, K. *Biochem. Biophys. Acta.* 1970, 200, 197–202.
30) Ahern, E.; Ahern, V.; Hilton, T.; Serjeant, G. D.; Serjeant, B. E.; Seakins, M.; Lang, A.; Middleton, A.; Lehmann, H. *Febs Lett.* 1976, 69, 99–102.
31) Bonaventura, J.; Riggs, A.; *J. Biol. Chem.* 1968, 243, 980–991.
32) Nagel, R. L.; Lynfield, J.; Johnson, J.; Landeau, L.; Bookchin, R. M.; Harris, M. B. *N. Eng. J. Med.* 1976, 295, 125–130.
33) Arous, N.; Braconnier, F.; Thillet, J.; Blouquit, Y.; Galacteros, F.; Chevrier, M.; Bordahandy, C.; Rosa, J. *Febs Lett.* 1981, 126, 114–116.
34) Efremov, G. D.; Huisman, T. H. J.; Smith, L. L.; Wilson, J. B.; Kitchens, J. L.; Wrightston, R. N.; Adams, H. R.; *J. Biol. Chem.* 1969, 244, 6105–6116.
35) Turner, J. W.; Jones, R. T.; Brimhall, B.; DuVal, M. C.; Koler, R. D. *Biochem. Genet.* 1976, 14, 577–585.
36) Imamura, T.; Fujita, S.; Ohta, Y-; Hanada, M.; Yanase, T. *J. Clin. Invest.* 1969, 48, 2341–2348.
37) Moo-Penn, W. F.; Wolff, J. A.; Simon, G.; Vacek, M.; Jue, D. L.; Johnson, M. H. *Febs Lett.* 1978, 92, 53–56.

38) King, M. A. R.; Willshire, B. G.; Lehmann, H.; Marimoto, H. *Br. J. Haem.* 1972, 22, 125–134.
39) Ranney, H. M.; Jacobs, A. S.; Nagel, R. L. *Nature* 1967, 213, 876–878.
40) Minnich, V.; Hill, R. J.; Khuri, P. D.; Anderson M. E. *Blood* 1965, 25, 830–838.
41) Ohba, Y.; Miyaji, T.; Murakami, M.; Kadowaki, S.; Fujita, T.; Oimoni, M.; Hatanaka, H.; Ishikawa, K.; Baba, S.; Hitaka, K.; Imai, K. *Hemoglobin* 1986, 10, 109–126.

TABLE 3

Candidate Non-Naturally Occurring Low Affinity Hemoglobin Mutants alpha chain 46 phe—>thr
46 phe—>ser
46 phe—>ala
58 his—>phe
58 his—>trp
61 lys—>thr
61 lys—>ser
61 lys—>met
61 lys—>asn
62 val—>leu
62 val—>ile
62 val—>phe
62 val—>trp
65 ala—>asp
94 asp—>gln
94 asp—>thr
94 asp—>ser
94 asp—>lys
94 asp—>gly
94 asp—>arg beta chain 21 asp—>ala
21 asp—>ser
45 phe—>ala
45 phe—>thr
45 phe—>val
63 his—>phe
63 his—>trp
66 lys—>ser
66 lys—>asn
67 val—>phe
67 val—>trp
67 val—>ile
70 ala—>glu
70 ala—>ser
70 ala—>thr
96 leu—>phe
96 leu—>his
96 leu—>lys
98 val—>trp
98 val—>phe
102 asn—>asp
102 asn—>glu
102 asn—>arg
102 asn—>his
102 asn—>gly
108 asn—>arg
108 asn—>glu

TABLE 400

HIGH OXYGEN AFFINITY, NATURALLY OCCURRING HEMOGLOBIN MUTANTS

| Structure | | Name |
|---|---|---|
| A. Alpha Chain Mutants | | |
| 6 (A4) | Asp—>Ala | Sawara |
| | Asp—>Asn | Dunn |
| | Asp—>Val | Ferndown |
| | Asp—>Tyr | Woodville |
| | Lys—>Asn | Albany-Suma |
| 40 (C5) | Lys—>Glu | Kariya |
| 44 (CE2) | Pro—>Leu | Milledgeville |
| | Pro—>Arg | Kawachi |
| 45 (CE3) | His—>Arg | Fort de France |
| 85 (F6) | Asp—>Asn | G-Norfolk |
| 92 (FG4) | Arg—>Gln | J-Cape Town |
| | Arg—>Leu | Chesapeake |
| 95 (G2) | Pro—>Leu | G-Georgia |
| | Pro—>Ser | Rampa |
| | Pro—>Ala | Denmark Hill |
| | Pro—>Arg | St. Luke's |
| 97 (G4) | Asn—>Lys | Dallas |
| 126 (H9) | Asp—>Asn | Tarrant |
| 141 (HC3) | Arg—>His | Suresnes |
| | Arg—>Ser | J-Cubujuqui |
| | Arg—>Leu | Legnano |
| B. Beta Chain Mutants | | |
| 2 (NA2) | His—>Arg | Deer Lodge |
| | His—>Gln | Okayama |
| 20 (B2) | Val—>Met | Olympia |
| 23 (B5) | Val—>Asp | Strasbourg |
| | Val—>Phe | Palmerston North |
| 34 (B16) | Val—>Phe | Pitie-Salpetriere |
| 36 (C2) | Pro—>Thr | Linkoping |
| 37 (C3) | Trp—>Ser | Hirose |
| 40 (C6) | Arg—>Lys | Athens-Ga |
| | Arg—>Ser | Austin |
| 51 (D2) | Pro—>Arg | Willamette |
| | Leu—>His | Brisbane |
| 79 (EF3) | Asp—>Gly | G-Hsi-Tsou |
| | Lys—>Thr | Rahere |
| | Lys—>Met | Helsinki |
| 89 (F5) | Ser—>Asn | Creteil |
| | Ser—>Arg | Vanderbilt |
| 94 (FG1) | Asp—>His | Barcelona |
| | Asp—>Asn | Bunbury |
| 96 (FG3) | Leu—>Val | Regina |
| 97 (FG4) | His—>Gln | Malmo |
| | His—>Leu | Wood |
| 99 (G1) | Asp—>Asn | Kempsey |
| | Asp—>His | Yakima |
| | Asp—>Ala | Radcliffe |
| | Asp—>Tyr | Ypsilanti |
| | Asp—>Gly | Hotel-Dieu |
| | Asp—>Val | Chemilly |
| 100 (G2) | Pro—>Leu | Brigham |
| 101 (G3) | Glu—>Lys | British Columbia |
| | Glu—>Gly | Alberta |
| | Glu—>Asp | Potomac |
| 103 (G5) | Phe—>Leu | Heathrow |
| 109 (G11) | Val—>Met | San Diego |
| 121 (GH4) | Glu—>Gln | D-Los Angeles |
| | Pro—>Gln | Tu Gard |
| | Ala—>Pro | Crete |
| 140 (H18) | Ala—>Thr | St.-Jacques |
| 142 (H20) | Ala—>Asp | Ohio |
| 143 (H21) | His—>Arg | Abruzzo |
| | His—>Gln | Little Rock |
| | His—>Pro | Syracuse |
| 144 (HC1) | Lys—>Asn | Andrew-Minneapolis |
| 145 (HC2) | Tyr—>His | Bethesda |
| | Tyr—>Cys | Rainier |
| | Tyr—>Asp | Fort Gordon |
| | Tyr—>Term | McKees Rocks |
| 146 (HC3) | His—>Asp | Hiroshima |
| | His—>Pro | York |
| | His—>Leu | Cowtown |

We claim:

1. A non-naturally occuring pseudotetrameric hemoglobin-like protein which is a pseudotetramer comprising four globin-like domains, said pseudotetramer comprising a pseudodimeric polypeptide having two substantially homologous globin-like domains, one of which is mutated to provide an asymmetric crosslinkable cysteine residue, the corresponding residue in the other globin-like domain of said pseudodimeric polypeptide being an amino acid other than cysteine, said pseudotetramer further comprising at least one other globin-like domain-bearing polypeptide.

2. A non-naturally occuring multimeric hemoglobin-like protein composed of two or more pseudotetrameric hemoglobin-like proteins according to claim 1, the asymmetric crosslinkable cysteine residue of a first pseudotetramer being crosslinked to the asymmetric crosslinkable cysteine residue of a second pseudotetramer.

3. A method of supplementing the oxygen carrying capacity of blood which comprises administering to a patient a composition comprising the protein of claim 2, wherein each of the globin-like domains is a mammalian globin-like domain.

4. The protein of claim 2 in which the protein is composed of two pseudotetramers.

5. A method of supplementing the oxygen carrying capacity of blood which comprises administering to a patient a composition comprising the protein of claim 4, wherein each of the globin-like domains is a mammalian globin-like domain.

6. The protein of claim 2 wherein the crosslink comprises a disulfide bond.

7. A method of supplementing the oxygen carrying capacity of blood which comprises administering to a patient a composition comprising the protein of claim 6, wherein each of the globin-like domains is a mammalian globin-like domain.

8. The protein of claim 2 wherein the crosslink is formed by reaction of the pseudotetramers with a multi-functional, thiol-specific crosslinking reagent.

9. The protein of claim 8 wherein the crosslinking reagent forms a crosslink which is substantially less reducible by reducing agents endogenous to plasma than would be a disulfide bond between the same two cysteine residues.

10. The protein of claim 8 wherein the crosslink is a thioether or a thio-maleiimide crosslink.

11. The protein of claim 8 in which the crosslinking reagent is a polyethylene glycol derivative with thiol-specific reactive moieties.

12. A method of supplementing the oxygen carrying capacity of blood which comprises administering to a patient a composition comprising the protein of claim 8, wherein each of the globin-like domains is a mammalian globin-like domain.

13. The protein of claim 8, in which the protein is composed of more than two pseudotetramers.

14. A method of supplementing the oxygen carrying capacity of blood which comprises administering to a patient a composition comprising the protein of claim 13, wherein each of the globin-like domains is a mammalian globin-like domain.

15. The protein of claim 8 in which the crosslinking agent comprises a peptide moiety.

16. The protein of claim 15 in which the crosslinking agent comprises one or more D-amino acids.

17. The protein of claim 15 in which the peptide moiety comprises a stable, extended, secondary structure.

18. The protein of claim 17 in which the peptide moiety comprises a polyproline helix.

19. The protein of claim 17 in which the crosslinking agent comprises a two-stranded coiled coil.

20. The protein of claim 19 in which the two strands of the coiled coil are disulfide cross-linked.

21. The protein of claim 17 in which the crosslinking agent comprises a 4-helical or a 4-stranded coiled coil.

22. The protein of claim 17 in which the peptide moiety comprises a branched chain.

23. The protein of claim 8 wherein the crosslink comprises a negatively charged moiety, whereby the isoelectric point of the protein is reduced.

24. The protein of claim 23 wherein the negatively charged moiety comprises a plurality of Asp and/or Glu residues.

25. The protein of claim 1 wherein the cysteine residue lies in an alpha globin-like domain.

26. The protein of claim 1 wherein the cysteine residue lies in a beta globin-like domain.

27. The protein of claim 1, wherein the hemoglobin-like protein is mutated, relative to human hemoglobin, to inhibit haptoglobin binding.

28. The protein of claim 27 wherein said crosslinking inhibits haptoglobin binding.

29. The protein of claim 1 wherein the globin-like domains of the pseudodimeric polypeptide are joined by a linker moiety consisting essentially of one or more glycines.

30. The protein of claim 29 wherein the domains are alpha globin-like domains and the linker moiety is 1–3 glycines.

31. The protein of claim 29 wherein the domains are beta globin-like domains and the linker moiety is 2–9 glycines.

32. The protein of claim 1, which protein has a $P_{50}$ at least 10% greater than does human hemoglobin Ao under the same conditions.

33. A method of supplementing the oxygen carrying capacity of blood which comprises administering to a patient a composition comprising the protein of claim 32, wherein each of the globin-like domains is a mammalian globin-like domain.

34. The protein of claim 1, which protein has a $P_{50}$ at least 10% lower than does human hemoglobin Ao under the same conditions.

35. A method of supplementing the oxygen carrying capacity of blood which comprises administering to a patient a composition comprising the protein of claim 34, wherein each of the globin-like domains is a mammalian globin-like domain.

36. The protein of claim 1, wherein said protein has a $P_{50}$ of 24–32 torr.

37. The protein of claim 1, wherein said protein has substantially longer intravascular retention than normal hemoglobin free in plasma.

38. A method of supplementing the oxygen carrying capacity of blood which comprises administering to a patient a composition comprising the protein of claim 37, wherein each of the globin-like domains is a mammalian globin-like domain.

39. The protein of claim 1 wherein each of the globin-like domains is a vertebrate globin-like domain.

40. The protein of claim 1 wherein each of the globin-like domains is a mammalian globin-like domain.

41. The protein of claim 1 wherein each of the globin-like domains is a human globin-like domain.

42. A method of supplementing the oxygen carrying capacity of blood which comprises administering to a patient a composition comprising the protein of claim 1, wherein each of the globin-like domains is a vertebrate globin-like domain.

43. The method of claim 42 wherein each of the globin-like domains is a human globin-like domain.

44. The method of claim 42 in which the globin-like domains are mammalian globin-like domains.

45. A non-naturally occuring pseudooligomeric polypeptide comprising four or more globin-like domains.

46. The polypeptide of claim 45, said polypeptide comprising, as an interdomain spacer, a polyproline helix.

47. The polypeptide of claim 45, said polypeptide comprising as an interdomain spacer, a polyaspartate or polyglutamate helix.

48. The polypeptide of claim 45, said polypeptide comprising, as an interdomain spacer, an Artemia linker.

49. The polypeptide of claim 45, said polypeptide comprising, as an interdomain spacers, a helical coiled coil.

50. The polypeptide of claim 45 wherein the globin-like domains are human alpha globin-like domains and the interdomain spacer is about 20–50 Å.

51. The polypeptide of claim 50 wherein the interdomain spacer is -(Gly)$_7$ (SEQ ID NO:32), -(Gly)$_{1-3}$(Ala)$_{12}$-(Gly)$_{1-3}$ (SEQ ID NO:33) -(Gly)$_{1-3}$(Pro$_{12-16}$-(Gly)$_{1-3}$(SEQ ID NO:34)- or -(Gly)$_{1-3}$(ASP)$_{1-30}$-(Gly)$_{1-3}$(SEQ ID NO:35).

52. A non-naturally occuring multimeric hemoglobin-like protein which comprises the polypeptide of claim 45 and one or more additional globin-like domain-bearing polypeptide chains.

53. The protein of claim 52, wherein the crosslinked cysteine is at a mutation site marked on FIG. 2.

54. A method of supplementing the oxygen carrying capacity of blood which comprises administering to a patient a composition comprising the protein of claim 52, wherein each of the globin-like domains is a mammalian globin-like domain.

55. A recombinant DNA molecule comprising a DNA sequence encoding the polypeptide of claim 45.

56. A cell transformed with the molecule of claim 55, said molecule further comprising a promoter, functional in said cell, which is operably linked to said DNA sequence whereby said cell may be caused to express said polypeptide.

57. A method of producing a multimeric hemoglobin-like protein which comprises cultivating the cell of claim 56, said cell further comprising expressible DNA sequences encoding the globin subunits of said protein other than the globin-like domains of said polypeptide, and expressing said polypeptide and said subunits.

58. The polypeptide of claim 45 in which the polypeptide has exactly four globin-like domains.

59. The polypeptide of claim 45, in which the globin-like domains are vertebrate globin-like domains.

60. The polypeptide of claim 45 in which the globin-like domains are mammalian globin-like domains.

61. The polypeptide of claim 45 in which the globin-like domains are human globin-like domains.

62. A non-naturally occuring octameric hemoglobin-like protein which comprises two tetramers, each tetramer comprising two human alpha globin-like domains and two human beta globin-like domains, a cysteine in one tetramer being disulfide bonded to a corresponding cysteine in the second tetramer, the crosslinking of a third tetramer being essentially sterically prevented, with the proviso that the crosslinked cysteine is not at beta 83 (Hemoglobin Ta Li).

63. A method of supplementing the oxygen carrying capacity of blood which comprises administering to a patient a composition comprising the protein of claim 62, wherein each of the globin-like domains is a mammalian globin-like domain.

64. A non-naturally occuring pseudodimeric globin-like polypeptide having two substantially homologous globin-like domains, one of which is mutated to provide an asymmetric crosslinkable cysteine residue, the corresponding residue in the other globin-like domain of said pseudodimeric polypeptide being an amino acid other than cysteine.

65. The polypeptide of claim 64 in which the cysteine residue lies in an alpha globin-like domain.

66. The polypeptide of claim 64 in which the cysteine residue lies in a beta globin-like domain.

67. The polypeptide of claim 64 wherein each of the globin-like domains is a vertebrate globin-like domain.

68. The polypeptide of claim 64 wherein each of the globin-like domains is a mammalian globin-like domain.

69. The polypeptide of claim 64 in which each of the globin-like domains is a human globin-like domain.

70. A recombinant DNA molecule which comprises a DNA sequence encoding the pseudodimeric globin-like polypeptide of claim 64.

71. A cell transformed with the molecule of claim 70, said molecule further comprising a promoter, functional in said cell, which is operably linked to said DNA sequence, whereby said cell may be caused to express said polypeptide.

72. A method of producing a pseudodimeric globin-like polypeptide which comprises cultivating the cell of claim 71 under conditions conducive to expression of said polypeptide.

73. A method of producing a pseudotetrameric hemoglobin-like protein which comprises cultivating the cell of claim 71, said cell further comprising expressible DNA sequences encoding the globin subunits of said protein other than the globin-like domains of said polypeptide, and expressing said polypeptide and said subunits.

74. A method of producing a multimeric hemoglobin-like protein which comprises producing pseudotetrameric hemoglobin-like proteins by the method of claim 73 and then crosslinking the pseudotetrameric proteins.

* * * * *